United States Patent
Ramakrishnan

(10) Patent No.: US 12,163,816 B2
(45) Date of Patent: Dec. 10, 2024

(54) MULTIPHASE FLUID FLOW CHARACTERIZATION

(71) Applicant: Saudi Arabian Oil Company, Dhahran (SA)

(72) Inventor: Vijay Ramakrishnan, Houston, TX (US)

(73) Assignee: Saudi Arabian Oil Company, Dhahran (SA)

(*) Notice: Subject to any disclaimer, the term of this patent is extended or adjusted under 35 U.S.C. 154(b) by 150 days.

(21) Appl. No.: 17/813,541

(22) Filed: Jul. 19, 2022

(65) Prior Publication Data
US 2024/0027243 A1    Jan. 25, 2024

(51) Int. Cl.
G01F 1/37 (2006.01)
G01F 1/74 (2006.01)
G01N 9/26 (2006.01)
G01N 33/28 (2006.01)

(52) U.S. Cl.
CPC ............ G01F 1/372 (2013.01); G01F 1/74 (2013.01); G01N 9/26 (2013.01); G01N 33/2847 (2013.01)

(58) Field of Classification Search
CPC .............. G01F 1/372; G01F 1/74; G01N 9/26; G01N 33/2847
See application file for complete search history.

(56) References Cited

U.S. PATENT DOCUMENTS

| | | | |
|---|---|---|---|
| 3,175,403 A | 3/1965 | Nelson | |
| 7,281,415 B2 | 10/2007 | Johansen | |
| 8,621,937 B2 * | 1/2014 | Henry | G01F 1/8486 73/861.354 |
| 9,927,270 B2 | 3/2018 | Xie | |
| 2011/0296911 A1 * | 12/2011 | Moore | G01N 9/26 73/32 R |
| 2014/0012507 A1 * | 1/2014 | Trehan | G01V 11/002 702/12 |
| 2016/0341585 A1 * | 11/2016 | Liu | G01F 1/74 |

FOREIGN PATENT DOCUMENTS

| | | |
|---|---|---|
| CA | 2264225 | 8/2000 |
| CN | 108759951 | 11/2018 |

(Continued)

OTHER PUBLICATIONS

PCT International Search Report and Written Opinion in International Appln. No. PCT/US2023/028128, dated Oct. 20, 2023, 15 pages.

(Continued)

*Primary Examiner* — Kristina M Deherrera
*Assistant Examiner* — Jean F Morello
(74) *Attorney, Agent, or Firm* — Fish & Richardson P.C.

(57) ABSTRACT

A multiphase fluid is flowed from a flow pipe to a U-bend. Several differential pressures of the multiphase fluid flowing through the flow pipe and U-bend are measured. A mixture density of the multiphase fluid is determined at least based on the measured differential pressures. A total flow rate of the multiphase fluid is determined at least based on the measured differential pressures. In some cases, flow rates of each of the phases of the multiphase fluid can be determined at least based on the measured differential pressures.

19 Claims, 27 Drawing Sheets

(56) References Cited

FOREIGN PATENT DOCUMENTS

| CN | 108760569 | 11/2018 |
|---|---|---|
| WO | WO 1995033980 | 12/1995 |

OTHER PUBLICATIONS

U.S. Appl. No. 17/813,540, filed Jul. 19, 2022, Ramakrishnan.
U.S. Appl. No. 17/868,545, filed Jul. 19, 2022, Ramakrishnan.
Alleyne et al., "A 2-dimensional Fourier transform method for the quantitative measurement of Lamb modes," IEEE Symposium on Ultrasonics, Dec. 1990, 4 pages.
Alleyne et al., "A two-dimensional Fourier transform method for the measurement of propagating multimode signals," The Journal of the Acoustical Society of America, 1991, 89, 1159, 10 pages.
Almabrok, "Gas-Liquid Two-Phase Flow in up and Down Vertical Pipes," Thesis for the Degree of Doctor of Philosophy, Cranfield University, School of Engineering, Department of Offshore, Process and Energy Engineering, Oct. 2013, 116 pages.
Farestvedt, "The Use of Innovative Multi-Phase Flow Meters to Achieve Superior Measurement Accuracy and Reliability, While Lowering Overall Cost of Facility," 5th Annual Cost-Effective Well Site Facilities Onshore, 2018, retrieved from URL <https://www.lbcg.com/media/downloads/events/693/day-2-lars-farestvedt-general-manager-mpm-western-region-technipfmc.13297.pdf>, 15 pages.
Haldun Unalmis et al., "Subsea Multiphase Flowmeter: Performance Tests in Multiphase Flow Loop," SPE Asia Pacific Oil & Gas Conference and Exhibition, Oct. 2016 https://doi.org/10.2118/182378-MS.
Hall, "Use of Venturi Meters in Multiphase Flow Measurement," Flow Measurement Centre National Engineering Laboratory, Glasgow, UK, 1999, 21 pages.
Ma et al., "Flow pattern identification for two-phase flow in a U-bend and its contiguous straight tubes," Experimental Thermal and Fluid Science, May 2018, 93:218:234, 17 pages.
mccrometer.com [online], "V-Cone Flow Meter," 2022, retrieved on May 12, 2022, retrieved from URL <https://www.mccrometer.com/v-cone-flow-meter/product?id=52003823651/>, 2 pages.
Meribout et al., "A Multisensor Intelligent Device for Real-Time Multiphase Flow Metering in Oil Fields," IEEE Transactions on Instrumentation and Measurement, Jun. 2010, 59(6), 13 pages.
omega.com [online], "An introduction to Venturi Flow meters, flow nozzles, and segmental wedge elements," Apr. 2019, retrieved on May 12, 2022, retrieved from URL <https://www.omega.com/en-us/resources/venturi-meter/>, 10 pages https://www.omega.com/en-us/resources/venturi-meter/.
omega.com [online], "What is an orifice plate flow meter?," Apr. 2019, retrieved on May 12, 2022, retrieved from URL <https://www.omega.com/en-us/resources/orifice-plate-flow-meter/>, 10 pages.
Reader-Harris et al., "Best practice guide: Impulse Lines for Differential-Pressure Flow meters," TUV Nel Ltd., Sep. 2005, retrieved from URL <https://instrumentationforum.com/uploads/db4532/original/2X/6/62b92b8203c35c5ca8d16a5b2e7178b54a647d7b.pdf>, 22 pages.
slb.com [online], "Vx Spectra Surface multiphase flowmeter," 2017, retrieved on May 12, 2022, retrieved from URL <https://www.slb.com/-/media/files/testing-services/product-sheet/vx-spectra-surface-multiphase-flowmeter-ps.ashx>, 2 pages.
Stauffer et al., "Multiple tap sets to improve Venturi flowmeters performance characteristics with disturbed flow," AWWA Water Science, May, 1(3):e1134 2019.
Tan et al., "Mass Flow Rate Measurement of Oil-Water Two-Phase Flow by a Long-Waist Cone Meter," IEEE Transactions on Instrumentation and Measurement, 62(10), Oct. 2013, 10 pages.
Zardin et al., "Pressure Losses in Multiple-Elbow Paths and in V-Bends of Hydraulic Manifolds," Energies, Jun. 2017, 10(6):788.

\* cited by examiner

MULTIPHASE FLUID FLOW CHARACTERIZATION

TECHNICAL FIELD

This disclosure relates to characterization of the flow of multiphase fluids.

BACKGROUND

A multiphase fluid is a mixture of multiple phases of matter. Multiphase fluids can be non-homogenous and can thus exhibit complex flow characteristics. The characteristics of the flow of multiphase fluids in a conduit, for example, can depend on various factors, such as operating conditions (pressure and temperature), composition (and in turn, physical properties such as density and viscosity) of each of the phases, flow rate of each of the phases, and physical characteristics of the conduit (such as diameter and orientation) through which the multiphase fluid is flowing. Characterization of the flow of multiphase fluids can sometimes be difficult. In some cases, for example, in oil and gas operations, accurate flow metering of multiphase fluid mixtures (such as crude oil, natural gas, and brine) can be important.

SUMMARY

This disclosure describes technologies relating to flow characterization of multiphase fluids. Certain aspects of the subject matter described can be implemented as a system. The system includes a U-bend. The U-bend is configured to flow a multiphase fluid. The multiphase fluid includes a gas phase, an aqueous phase, and an oil phase. The U-bend includes a first conduit, a second conduit, and a connecting conduit. A cross-sectional flow area of the first conduit is substantially the same as a cross-sectional flow area of the second conduit. The connecting conduit connects the first conduit to the second conduit. The system includes a third conduit that is configured to flow the multiphase fluid. The third conduit has a cross-sectional flow area that is different from the cross-sectional flow area of the first conduit. The system includes a first bend connecting the third conduit to the first conduit. The system includes a fourth conduit that is configured to flow the multiphase fluid. The fourth conduit has a cross-sectional flow area that is substantially the same as the cross-sectional flow area of the third conduit. The system includes a second bend that connects the fourth conduit to the second conduit. The system includes a first differential pressure sensor, a second differential pressure sensor, a third differential pressure sensor, and a fourth differential pressure sensor. The first differential pressure sensor is configured to measure a first differential pressure of the multiphase fluid between a first location on the third conduit of the flow pipe and a second location on the first conduit of the U-bend. The second differential pressure sensor is configured to measure a second differential pressure of the multiphase fluid between a third location on the second conduit of the U-bend and a fourth location on the fourth conduit of the flow pipe. The third differential pressure sensor is configured to measure a third differential pressure of the multiphase fluid across a specified height along the first conduit of the U-bend. The fourth differential pressure sensor is configured to measure a fourth differential pressure of the multiphase fluid across the specified height along the second conduit of the U-bend. The system includes a computer. The computer includes a processor and a computer-readable storage medium. The processor is communicatively coupled to the first differential pressure sensor, the second differential pressure sensor, the third differential pressure sensor, and the fourth differential pressure sensor. The computer-readable storage medium is coupled to the processor and stores programming instructions for execution by the processor. The programming instructions instruct the processor to perform operations. The operations include receiving a first differential pressure signal from the first differential pressure sensor. The first differential pressure signal represents the first differential pressure of the multiphase fluid. The operations include receiving a second differential pressure signal from the second differential pressure sensor. The second differential pressure signal represents the second differential pressure of the multiphase fluid. The operations include receiving a third differential pressure signal from the third differential pressure sensor. The third differential pressure signal represents the third differential pressure of the multiphase fluid. The operations include receiving a fourth differential pressure signal from the fourth differential pressure sensor. The fourth differential pressure signal represents the fourth differential pressure of the multiphase fluid. The operations include determining a mixture density of the multiphase fluid at least based on the specified distance and a difference between the third differential pressure and the fourth differential pressure. The operations include determining a total flow rate of the multiphase fluid at least based on the first differential pressure, the second differential pressure, and the mixture density of the multiphase fluid.

This, and other aspects, can include one or more of the following features.

In some implementations, the mixture density of the multiphase fluid is determined by:

$$\rho = \frac{\Delta P_3 - \Delta P_4}{2 \times g \times h},$$

where $\rho$ is the mixture density of the multiphase fluid, $\Delta P_3$ is the third differential pressure of the multiphase fluid, $\Delta P_4$ is the fourth differential pressure of the multiphase fluid, g is an acceleration due to gravity, and h is the specified height.

In some implementations, the total flow rate of the multiphase fluid is determined as a first total mass flow rate of the multiphase fluid at least based on a first differential pressure equation:

$$m_{T1} = C_{d1} \times \varepsilon_1 \times K_1 \times \sqrt{2 \times \rho \times (\Delta P_1 - \rho \times g \times h)},$$

where $m_{T1}$ is the first total mass flow rate of the multiphase fluid, $C_{d1}$ is a first discharge coefficient, $\varepsilon_1$ is a first expansion factor, $K_1$ is a first fixed geometry factor proportional to the cross-sectional flow area of the first conduit, $\Delta P_1$ is the first differential pressure, $\rho$ is the mixture density of the multiphase fluid, g is the acceleration due to gravity, and h is the specified height.

In some implementations, the total flow rate of the multiphase fluid is determined as a second total mass flow rate of the multiphase fluid at least based on a second differential pressure equation:

$$m_{T2} = C_{d2} \times \varepsilon_2 \times K_2 \times \sqrt{2 \times \rho \times (\Delta P_2 + \rho \times g \times h)},$$

where $m_{T2}$ is the second total mass flow rate of the multiphase fluid, $C_{d2}$ is a second discharge coefficient, $\varepsilon_2$ is a second expansion factor, $K_2$ is a second fixed geometry factor proportional to a cross-sectional flow area of the fourth conduit, $\Delta P_2$ is the second differential pressure, $\rho$ is the mixture density of the multiphase fluid, g is the acceleration due to gravity, and h is the specified height.

In some implementations, the operations performed by the processor include comparing the first overall flow rate of the multiphase fluid and the second overall flow rate of the multiphase fluid to determine an adjustment of the first discharge coefficient ($C_{d1}$) or an adjustment of the second discharge coefficient ($C_{d2}$).

In some implementations, the first total mass flow rate ($m_{T1}$) is equal to the second total mass flow rate ($m_{T2}$). In some implementations, the mixture density of the multiphase fluid is a first mixture density of the multiphase fluid. In some implementations, the operations performed by the processor include determining a second mixture density of the multiphase fluid at least based on a combined differential pressure equation:

$$\rho_2 = \frac{Z \times \Delta P_1 - \Delta P_2}{g \times (1+Z)},$$

wherein $\rho_2$ is the second mixture density of the multiphase fluid, $\Delta P_1$ is the first differential pressure, $\Delta P_2$ is the second differential pressure, g is the acceleration due to gravity, and Z is defined by:

$$Z = \left(\frac{C_{d1} \times \varepsilon_1 \times K_1}{C_{d2} \times \varepsilon_2 \times K_2}\right)^2,$$

wherein $C_{d1}$ is the first discharge coefficient, $\varepsilon_1$ is the first expansion factor, $K_1$ is the first fixed geometry factor, $C_{d2}$ is the second discharge coefficient, $\varepsilon_2$ is the second expansion factor, and $K_2$ is the second fixed geometry factor.

In some implementations, the operations performed by the processor include comparing the first mixture density of the multiphase fluid and the second mixture density of the multiphase fluid to determine an accuracy of the first mixture density. In some implementations, the system includes dynamic pressure sensors coupled to the U-bend. In some implementations, each dynamic pressure sensor is configured to measure a dynamic pressure of the multiphase fluid flowing through the U-bend. In some implementations, the operations performed by the processor include cross-correlating the dynamic pressures measured by the dynamic pressure sensors to determine a speed of sound of the multiphase fluid flowing through the U-bend. In some implementations, the operations performed by the processor include determining a water-liquid ratio at least based on the speed of sound of the multiphase fluid and the mixture density of the multiphase fluid, wherein the water-liquid ratio is a ratio of a volume of the aqueous phase to a sum of the volume of the aqueous phase and a volume of the oil phase. In some implementations, the third differential pressure sensor is a first circumferential pressure sensor that spans an entire circumference of the first conduit, and the fourth differential pressure sensor is a second circumferential pressure sensor that spans an entire circumference of the second conduit.

Certain aspects of the subject matter described can be implemented as a method. A multiphase fluid is flowed from a flow pipe to a U-bend. The multiphase fluid includes a gas phase, an aqueous phase, and an oil phase. The U-bend includes a first conduit, a second conduit, and a connecting conduit. The connecting conduit connects the first conduit to the second conduit. The multiphase fluid flowing through the U-bend flows into the first conduit, through the connecting conduit, and out of the second conduit. The multiphase fluid is flowed from the U-bend to the flow pipe. The flow pipe includes a third conduit and a fourth conduit. The third conduit (of the flow pipe) is connected to the first conduit (of the U-bend) by a first bend. The fourth conduit (of the flow pipe) is connected to the second conduit (of the U-bend) by a second bend. Flowing the multiphase fluid from the flow pipe to the U-bend includes flowing the multiphase fluid from the third conduit (of the flow pipe) through the first bend to the first conduit (of the U-bend). Flowing the multiphase fluid from the U-bend to the flow pipe includes flowing the multiphase fluid from the second conduit (of the U-bend) through the second bend to the fourth conduit (of the flow pipe). A first differential pressure of the multiphase fluid is measured between a first location on the third conduit (of the flow pipe) and a second location on the first conduit (of the U-bend). A second differential pressure of the multiphase fluid is measured between a third location on the second conduit (of the U-bend) and a fourth location on the fourth conduit (of the flow pipe). A third differential pressure of the multiphase fluid is measured across a specified height along the first conduit (of the U-bend). A fourth differential pressure of the multiphase fluid is measured across the specified height along the second conduit (of the U-bend). A mixture density of the multiphase fluid is determined at least based on the specified height and a difference between the third differential pressure and the fourth differential pressure. A total flow rate of the multiphase fluid is determined at least based on the first differential pressure, the second differential pressure, and the mixture density of the multiphase fluid.

This, and other aspects, can include one or more of the following features.

In some implementations, the mixture density of the multiphase fluid is determined by:

$$\rho = \frac{\Delta P_3 - \Delta P_4}{2 \times g \times h},$$

where $\rho$ is the mixture density of the multiphase fluid, $\Delta P_3$ is the third differential pressure of the multiphase fluid, $\Delta P_4$ is the fourth differential pressure of the multiphase fluid, g is an acceleration due to gravity, and h is the specified height.

In some implementations, the total flow rate of the multiphase fluid is determined as a first total mass flow rate of the multiphase fluid at least based on a first differential pressure equation:

$$m_{T1} = C_{d1} \times \varepsilon_1 \times K_1 \times \sqrt{2 \times \rho \times (\Delta P_1 - \rho \times g \times h)},$$

where $m_{T1}$ is the first total mass flow rate of the multiphase fluid, $C_{d1}$ is a first discharge coefficient, $\varepsilon_1$ is a first expansion factor, $K_1$ is a first fixed geometry factor proportional to the cross-sectional flow area of the first conduit, $\Delta P_1$ is the first differential pressure, $\rho$ is the mixture density of the multiphase fluid, g is the acceleration due to gravity, and h is the specified height.

In some implementations, the total flow rate of the multiphase fluid is determined as a second total mass flow rate of the multiphase fluid at least based on a second differential pressure equation:

$$m_{T2} = C_{d2} \times \varepsilon_2 \times K_2 \times \sqrt{2 \times \rho \times (\Delta P_2 + \rho \times g \times h)},$$

where $m_{T2}$ is the second total mass flow rate of the multiphase fluid, $C_{d2}$ is a second discharge coefficient, $\varepsilon_2$ is a second expansion factor, $K_2$ is a second fixed geometry factor proportional to a cross-sectional flow area of the fourth conduit, $\Delta P_2$ is the second differential pressure, $\rho$ is the mixture density of the multiphase fluid, g is the acceleration due to gravity, and h is the specified height.

In some implementations, the first overall flow rate of the multiphase fluid and the second overall flow rate of the multiphase fluid are compared to determine an adjustment of the first discharge coefficient ($C_{d1}$) or an adjustment of the second discharge coefficient ($C_{d2}$).

In some implementations, the first total mass flow rate ($m_{T1}$) is equal to the second total mass flow rate ($m_{T2}$). In some implementations, the mixture density of the multiphase fluid is a first mixture density of the multiphase fluid. In some implementations, the method includes determining a second mixture density of the multiphase fluid at least based on a combined differential pressure equation:

$$\rho_2 = \frac{Z \times \Delta P_1 - \Delta P_2}{g \times (1 + Z)},$$

wherein $\rho_2$ is the second mixture density of the multiphase fluid, $\Delta P_1$ is the first differential pressure, $\Delta P_2$ is the second differential pressure, g is the acceleration due to gravity, and Z is defined by:

$$Z = \left(\frac{C_{d1} \times \varepsilon_1 \times K_1}{C_{d2} \times \varepsilon_2 \times K_2}\right)^2,$$

wherein $C_{d1}$ is the first discharge coefficient, $\varepsilon_1$ is the first expansion factor, $K_1$ is the first fixed geometry factor, $C_{d2}$ is the second discharge coefficient, $\varepsilon_2$ is the second expansion factor, and $K_2$ is the second fixed geometry factor.

In some implementations, the first mixture density of the multiphase fluid and the second mixture density of the multiphase fluid are compared to determine an accuracy of the first mixture density. In some implementations, dynamic pressures of the multiphase fluid flowing through the U-bend are measured. In some implementations, the dynamic pressures are cross-correlated to determine a speed of sound of the multiphase fluid flowing through the U-bend. In some implementations, a water-liquid ratio (a ratio of a volume of the aqueous phase to a sum of the volume of the aqueous phase and a volume of the oil phase) is determined at least based on the speed of sound of the multiphase fluid and the mixture density of the multiphase fluid. In some implementations, the first differential pressure is measured by a first differential pressure sensor. In some implementations, the first differential pressure sensor is coupled to the third conduit of the flow pipe at the first location and coupled to the first conduit of the U-bend at the second location. In some implementations, the second differential pressure is measured by a second differential pressure sensor. In some implementations, the second differential pressure sensor is coupled to the second conduit of the U-bend at the third location and coupled to the fourth conduit of the flow pipe at the fourth location. In some implementations, the third differential pressure is measured by a third differential pressure sensor. In some implementations, the third differential pressure sensor is coupled to the first conduit of the U-bend at a fifth location and coupled to the first conduit of the U-bend at a sixth location. In some implementations, the fifth location and the sixth location are separated by the specified height along the first conduit. In some implementations, the fourth differential pressure is measured by a fourth differential pressure sensor. In some implementations, the fourth differential pressure sensor is coupled to the second conduit of the U-bend at a seventh location and coupled to the second conduit of the U-bend at an eighth location. In some implementations, the seventh location and the eighth location are separated by the specified height along the second conduit. In some implementations, the third differential pressure sensor is a first circumferential pressure sensor that spans an entire circumference of the first conduit. In some implementations, the fourth differential pressure sensor is a second circumferential pressure sensor that spans an entire circumference of the second conduit.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes flow characterization of multiphase fluids. The apparatuses described here can be used to accurately measure the total flow rate, the mixture density, and the phase flow rates of a multiphase fluid. This information can then be used to determine other properties of the multiphase fluid, for example, based on additional known information. The apparatuses include multiple connected conduits including an elbow (or L-bend) and a U-bend. The apparatuses include multiple pressure sensors for measuring differential pressures across various location pairs of the flowing multiphase fluid. The measured differential pressures can be compared and manipulated to determine the total flow rate, the mixture density, and the phase flow rates of the flowing multiphase fluid.

The subject matter described in this disclosure can be implemented in particular implementations, so as to realize one or more of the following advantages. The apparatuses, systems, and methods described here can be implemented independent of the use of radioactive energy sources (such as gamma-ray attenuation), which can be hazardous. The apparatuses, systems, and methods described here can be implemented to accurately determine the total flow rate, the mixture density, and the phase flow rates of a multiphase fluid, even in situations in which a gas phase is present in a non-negligible amount. The apparatuses, systems, and methods described here can be implemented to accurately determine the total flow rate, the mixture density, and the phase flow rates of a multiphase fluid, while taking into account frictional and shear pressure losses of the multiphase fluid. The apparatuses, systems, and methods described here can be implemented to accurately determine the total flow rate, the mixture density, and the phase flow rates of a multiphase fluid, even in complex flow regimes such as slug-flow, plug-flow, and annular flow regimes. The apparatuses, systems, and methods described here can be implemented to accurately determine the total flow rate, the mixture density, and the phase flow rates of a multiphase fluid, even in situations in which there is slip (that is, differential flow velocity) between gas and liquid phases. The apparatuses, systems, and methods described here can take advantage of pipe geometry (and associated fluid dynamics) to measure a relatively simple (and more direct) flow/fluid property (such as differential pressure), rather than a relatively complex (and more indirect) fluid/flow property (such as electromagnetic (spectral) absorption/transmission) to accurately determine the total flow rate, the mixture density, and the phase flow rates of a multiphase fluid. The apparatuses, systems, and methods described here can be implemented in conjunction with other flow metering components to supplement and/or enhance the accuracy of the characterization of multiphase fluid flow.

Figure 1A:
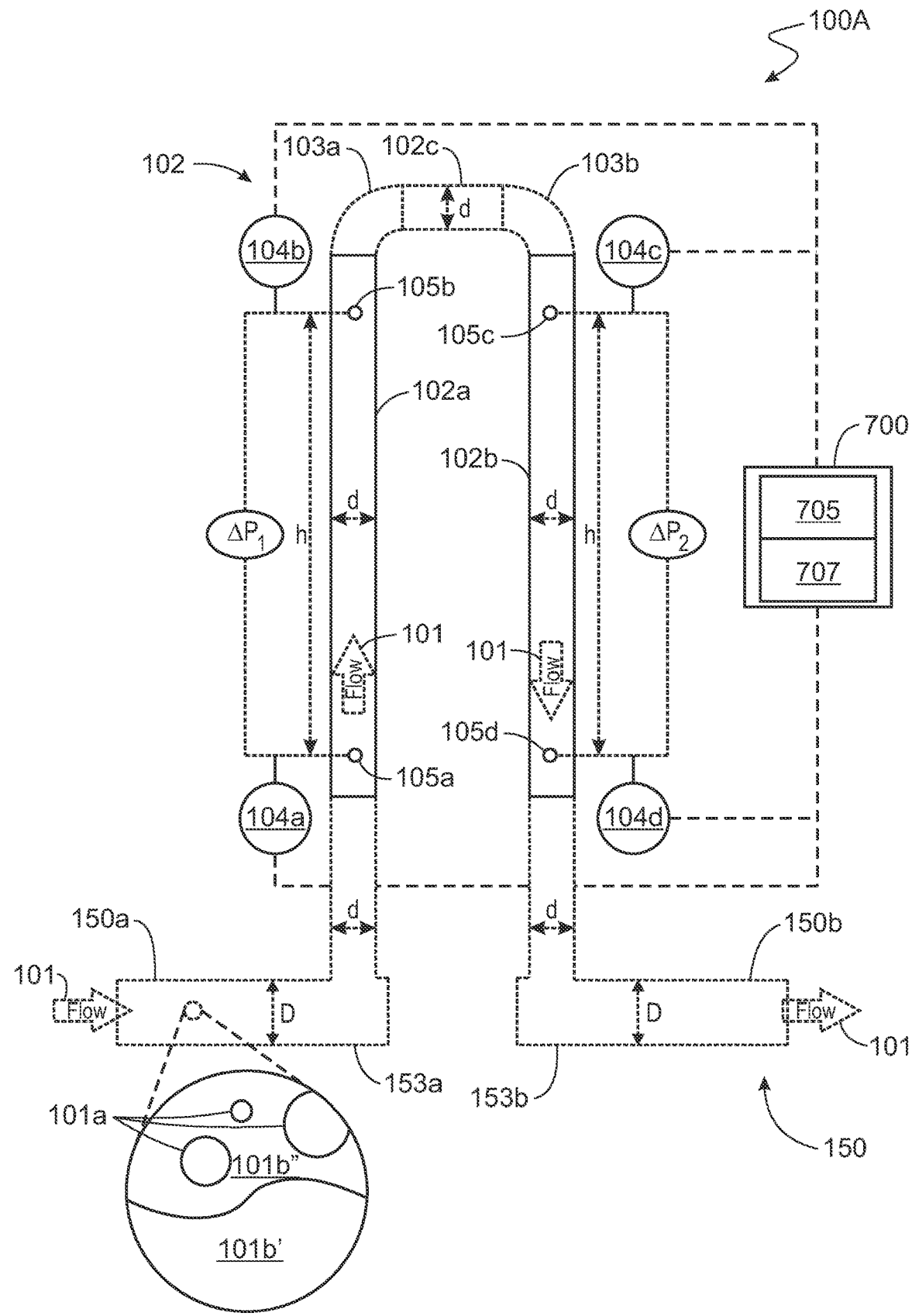
FIG. 1A is a schematic diagram of an example apparatus which can be used to measure a density of a multiphase fluid.

FIG. 1A depicts an apparatus 100A which can be used to measure a density of a multiphase fluid 101. The multiphase fluid 101 can be a 2-phase or a 3-phase fluid. For example, the multiphase fluid 101 can include a gas phase 101a and a liquid phase 101b. In some implementations, the liquid phase 101b includes an aqueous phase 101b' and an oil phase 101b". For example, the multiphase fluid 101 can include a gas phase 101a, an aqueous phase 101b', and an oil phase 101b". As one example, the multiphase fluid 101 can include hydrocarbon gas, hydrocarbon liquid, and water (or brine).

The apparatus 100A includes a U-bend 102 which is configured to flow the multiphase fluid 101. The U-bend 102 includes a first conduit 102a, a second conduit 102b, and a connecting conduit 102c. In some implementations, the second conduit 102b is parallel to the first conduit 102a. In some implementations, a longitudinal length of the first conduit 102a is substantially the same as a longitudinal length of the second conduit 102b, and a cross-sectional area of the first conduit 102a is substantially the same as a cross-sectional area of the second conduit 102b, such that a frictional component of the pressure drop experienced by the multiphase fluid 101 flowing through these components (102a, 102b) of the U-bend 102 is substantially the same for each component. For example, each of the first conduit 102a and the second conduit 102b have substantially the same inner diameter, d. The connecting conduit 102c connects the first conduit 102a to the second conduit 102b. In some implementations, the first conduit 102a, the second conduit 102b, and the connecting conduit 102c are integrated, such that the U-bend 102 is a singular, unitary body, as opposed to parts that are disjointed and coupled together to form the U-bend 102. In some implementations, the connecting conduit 102c is perpendicular to the first conduit 102a and to the second conduit 102b. The multiphase fluid 101 flowing through the U-bend 102 flows into the first conduit 102a, through the connecting conduit 102c, and out of the second conduit 102b. In some implementations, each of the first conduit 102a, the second conduit 102b, and the connecting conduit 102c are made of the same material, such that the friction experienced by the multiphase fluid 101 flowing through each of the first conduit 102a, the second conduit 102b, and the connecting conduit 102c is substantially the same. In some implementations, the connecting conduit 102b is connected to the first conduit 102a by a first curved bend 103a. In some implementations, the connecting conduit 102c is connected to the second conduit 102b by a second curved bend 103b. In some implementations, the first conduit 102a, the second conduit 102b, the connecting conduit 102c, the first curved bend 103a, and the second curved bend 103b are integrated, such that the U-bend 102 is a singular, unitary body, as opposed to parts that are disjointed and coupled together to form the U-bend 102. The first curved bend 103a and the second curved bend 103b can be made of the same material as the first conduit 102a, the second conduit 102b, and the connecting conduit 102c, such that the friction experienced by the multiphase fluid 101 flowing through each of the components of the U-bend 102 is substantially the same.

The apparatus 100A includes a first pair of pressure sensors 104a, 104b. The pressure sensors 104a, 104b are coupled to the first conduit 102a via pressure ports 105a, 105b, respectively. The pressure sensors 104a, 104b are cooperatively configured to measure a first differential pressure of the multiphase fluid 101 flowing through the U-bend 102. The pressure ports 105a, 105b to which the pressure sensors 104a, 104b are coupled, respectively, are separated by a specified differential pressure height, h, along the first tubular 102a. The apparatus 100A includes a second pair of pressure sensors 104c, 104d. The pressure sensors 104c, 104d are coupled to the second conduit 102b via pressure ports 105c, 105d. The pressure sensors 104c, 104d are cooperatively configured to measure a second differential pressure of the multiphase fluid 101 flowing through the U-bend 102. The pressure ports 105c, 105d to which the pressure sensors 104c, 104d are coupled, respectively, are separated by the same specified differential pressure height, h, along the second tubular 102b. In other words, the height difference between the pressure ports 105a, 105b of the pressure sensors 104a, 104b and the height difference between the pressure ports 105c, 105d of the pressure sensors 104c, 104d are the same, such that the frictional components of the pressure drops experienced by the multiphase fluid 101 flowing through the first conduit 102a (measured by pressure sensors 104a, 104b) and through the second conduit 102b (measured by the pressure sensors 104c, 104d) are substantially the same. In some implementations, the first pair of pressure sensors 104a, 104b is replaced by a first differential pressure sensor that is coupled to the first conduit 102a via the pressure ports 105a, 105b. In some implementations, the second pair of pressure sensors 104c, 104d is replaced by a second differential pressure sensor that is coupled to the second conduit 102b via the pressure ports 105c, 105d.

As shown in FIG. 1A, the U-bend 102 can be connected to a flow pipe 150 that flows the multiphase fluid 101. The flow pipe 150 includes a first pipe 150a and a second pipe 150b. The terms "pipe" and "conduit" are synonymous. The term "pipe" is being used in relation to the flow pipe 150 and the term "conduit" is being used in relation to the U-bend 102 simply for consistency/clarity and to avoid confusion. In some implementations, the U-bend 102 is connected to the flow pipe 150 by angled bends 153a, 153b. For example, the first conduit 102a of the U-bend 102 is connected to the first pipe 150a of the flow pipe 150 by the first angled bend 153a. For example, the second conduit 102b of the U-bend 102 is connected to the second pipe 150b of the flow pipe 150 by the second angled bend 153b. In some implementations, as shown in FIG. 1A, the angled bends 153a, 153b are 90-degree angled bends. Although shown as 90-degree angled bends in FIG. 1A, the angled bends 153a, 153b can have a different degree angle, such as in a range of from 30 degrees to 150 degrees. In some implementations, the first conduit 102a, the second conduit 102b, the connecting conduit 102c, the first curved bend 103a, the second curved bend 103b, the first angled bend 153a, the second angled bend 153b, and the flow pipe 150 are integrated, such that the U-bend 102 and the flow pipe 150 form a singular, unitary body, as opposed to parts that are disjointed and coupled together. In some implementations, the angled bends 153a, 153b are replaced by curved bends (similar to the curved bends 103a, 103b).

In some implementations, the inner diameters (d) of the first conduit 102a and the second conduit 102b are different from the inner diameter (D) of the flow pipe 150. A change in cross-sectional flow area between the flow pipe 150 and the U-bend 102 can ensure that the differential pressures of the multiphase fluid 101 flowing across the angled bends 153a, 153b are predominantly functions of the total flow rate of the multiphase fluid 101 as opposed to other factors, such as frictional pressure losses. In some implementations, the inner diameters (d) of the first conduit 102a and the second conduit 102b can be in a range of from half of the inner diameter (D) of the flow pipe 150 to double the inner diameter (2D) of the flow pipe 150 (that is, D/2≤d≤2D).

In some implementations, each of the pressure sensors (104a, 104b, 104c, 104d) are at least a threshold distance away from the closest bend. The threshold distance is long enough to allow the flow of the multiphase fluid 101 to fully develop after the disturbance in flow caused by an upstream bend or long enough to allow the flow of the multiphase fluid 101 to remain fully developed before approaching a downstream bend. Without being bound to theory, the method of sensing (for example, the application and/or objective of the measurement) can determine the location at which the sensors should be placed. For the apparatuses and methods described here, the threshold distance can be, for example, four times the inner diameter, d (that is, 4d). For example, if the inner diameter (d) of the U-bend 102 is 1 inch, the threshold distance is 4 inches. For example, the pressure port 105a, to which the pressure sensor 104a is coupled, is located on the first conduit 102a at least 4d distance away from the angled bend 153a. For example, the pressure port 105b, to which the pressure sensor 104b is coupled, is located on the first conduit 102a at least 4d distance away from the curved bend 103a. For example, the pressure port 105c, to which the pressure sensor 104c is coupled, is located on the second conduit 102b at least 4d distance away from the curved bend 103b. For example, the pressure port 105d, to which the pressure sensor 104d is coupled, is located on the second conduit 102b at least 4d distance away from the angled bend 153b.

Figure 7:
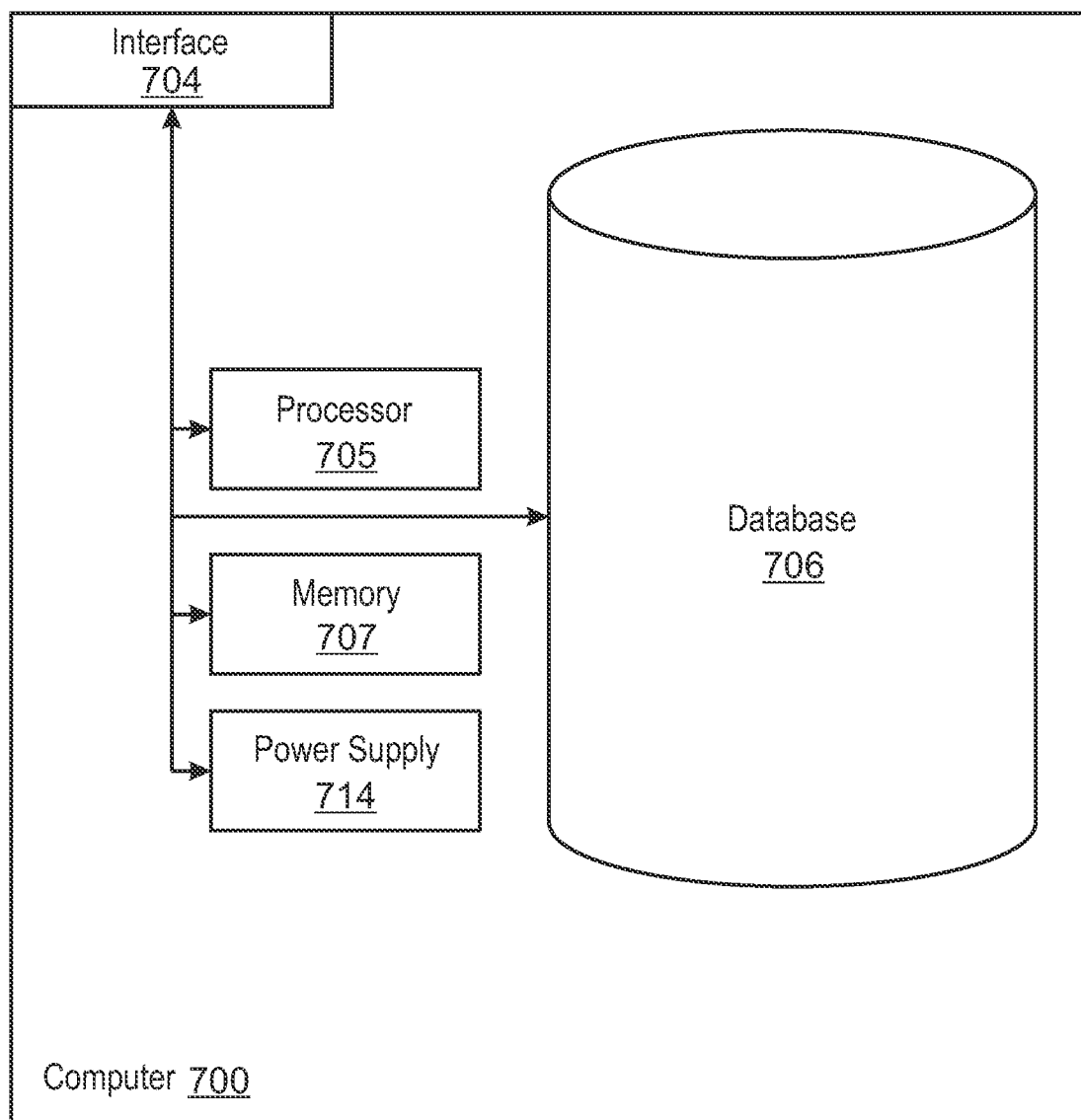
FIG. 7 is a block diagram of an example computer system.

As shown in FIG. 1A, the apparatus 100A can be communicatively coupled to a computer 700. The computer 700 includes a processor 705 and a memory 707. The processor 705 can be communicatively coupled to the first pair of pressure sensors 104a, 104b (or first differential pressure sensor) and to the second pair of pressure sensors 104c, 104d (or second differential pressure sensor). The memory 707 is coupled to the processor 705. The computer 700 is also shown in FIG. 7 and is described in more detail later. The memory 707 stores programming instructions for execution by the processor 705. The programming instructions can instruct the processor 705 to perform various operations. The operations performed by the processor 705 can include receiving a first differential pressure signal from the first pair of pressure sensors 104a, 104b (or first differential pressure sensor). The first differential pressure signal can represent the first differential pressure of the multiphase fluid 101 measured by the first pair of pressure sensors 104a, 104b (or first differential pressure sensor). The operations performed by the processor 705 can include receiving a second differential pressure signal from the second pair of pressure sensors 104c, 104d (or second differential pressure sensor). The second differential pressure signal can represent the second differential pressure of the multiphase fluid 101 measured by the pressure sensors 104c, 104d (or second differential pressure sensor). The operations performed by the processor 705 can include determining an overall density of the multiphase fluid 101 at least based on a difference between the first differential pressure and the second differential pressure of the multiphase fluid 101 and the specified differential pressure height, h.

In cases in which the first conduit 102a and the second conduit 102b are in a vertical orientation (relative to a reference horizontal, such as ground level), the differential pressure loss of multiphase fluid 101 flowing across a vertical distance can be estimated by Equation 1:

$$\Delta P = \rho \times g \times h_v - \Delta P_f \qquad (1)$$

where ΔP is the total differential pressure loss of the multiphase fluid 101, ρ is the apparent mixture density of the multiphase fluid 101, g is acceleration due to gravity, $h_v$ is the difference in vertical height of two reference points (such as the locations of the pressure ports 105a, 105b or the locations of the pressure ports 105c, 105d), and $\Delta P_f$ is the pressure loss due to miscellaneous factors, such as frictional losses and multiphase shear. Thus, the first differential pressure measured by the first pair of pressure sensors 104a, 104b can be estimated by Equation 1a, and the second differential pressure measured by the second pair of pressure sensors 104c, 104d can be estimated by Equation 1b:

$$\Delta P_1 = \rho \times g \times h_1 + \Delta P_{f1} \quad (1a)$$

$$\Delta P_2 = -\rho \times g \times h_2 + \Delta P_{f2} \quad (1b)$$

The apparent mixture density of the multiphase fluid (ρ) can be determined by obtaining the difference between the first and second differential pressures ($\Delta P_1 - \Delta P_2$) and re-arranging the resulting equation to solve for ρ. The difference between the first and second differential pressures is shown by Equation 2a:

$$\Delta P_1 - \Delta P_2 = \rho \times g \times h_1 + \Delta P_{f1} + \rho \times g \times h_2 - \Delta P_{f2} \quad (2a)$$

Because the flow characteristics of the first conduit 102a and the second conduit 102b are substantially the same, $\Delta P_{f1}$ and $\Delta P_{f2}$ can be assumed to be substantially the same ($\Delta P_{f1} \cong \Delta P_{f2}$), thus Equation 2a can be re-written as Equation 2b:

$$\Delta P_1 - \Delta P_2 = \rho \times g \times h_1 + \rho \times g \times h_2 \quad (2b)$$

In cases in which the first differential pressure ($\Delta_{P1}$) and the second differential pressure ($\Delta P_1$) are each measured across the same vertical distance, but at opposite flow directions (as is the case for the first pair of pressure sensors 104a, 104b and the second pair of pressure sensors 104c, 104d shown in FIG. 1A), the first vertical height ($h_1$) is equal to the second vertical height ($h_2$)—that is, $h_1 = h_2$. Thus, Equation 2b can be re-written as Equation 2c:

$$\Delta P_1 - \Delta P_2 = \rho \times g \times h_1 \quad (2c)$$

Inputting h as the vertical height for $h_1$ and re-arranging Equation 2c to solve for the overall density of the multiphase fluid (ρ) results in Equation 2d:

$$\rho = \frac{\Delta P_1 - \Delta P_2}{2 \times g \times h} \quad (2d)$$

The first differential pressure ($\Delta P_1$) is measured by the first pair of pressure sensors 104a, 104b (or first differential pressure sensor). The second differential pressure ($\Delta P_2$) is measured by the second pair of pressure sensors 104c, 104d (or second differential pressure sensor). The acceleration of gravity is a known universal constant. Thus, $\Delta P_1$, $\Delta P_2$, g, and h can be input to Equation 2d to estimate the mixture density (ρ) of the multiphase fluid 101.

Additionally, information about the frictional/shear pressure losses can be estimated by adding the first differential pressure ($\Delta P_1$) and the second differential pressure ($\Delta P_2$), as shown in Equation 2e:

$$\Delta P_1 + \Delta P_2 = \rho \times g \times h_1 + \Delta P_{f1} - \rho \times g \times h_2 + \Delta P_{f2} \quad (2e)$$

As mentioned previously, in cases where the first vertical height ($h_1$) is equal to the second vertical height ($h_2$), Equation 2e can be re-written as Equation 2f:

$$\Delta P_1 + \Delta P_2 = \Delta P_{f1} + \Delta P_{f2} \quad (2f)$$

As mentioned previously, because the flow characteristics of the first conduit 102a and the second conduit 102b are substantially the same, $\Delta P_{f1}$ and $\Delta P_{f2}$ can be assumed to be substantially the same ($\Delta P_{f1} \cong \Delta P_{f2}$) and can simply be substituted as $\Delta P_f$, thus Equation 2f can be re-written as Equation 2g:

$$\Delta P_1 + \Delta P_2 = 2 \times \Delta P_f \quad (2g)$$

Re-arranging Equation 2g to solve for frictional/shear pressure losses ($\Delta P_f$) provides Equation 2h:

$$\Delta P_f = \frac{\Delta P_1 + \Delta P_2}{2} \quad (2h)$$

The information obtained related to frictional/shear pressure losses ($\Delta P_f$) can be useful for determining other correlations and flow characteristics of the multiphase fluid 101. For example, if the apparatus 100A is used in conjunction with a Venturi-type flowmeter, the information obtained related to frictional/shear pressure losses ($\Delta P_f$) can be used to determine correlations of variables used in the Venturi-type flowmeter calculations. For a Venturi-type flowmeter, Bernoulli's equation can be converted into the form shown in Equation 3a:

$$m_T = C_d \times \varepsilon \times K \times \sqrt{2 \times \rho \times (\Delta P - k_f \times \Delta P_f)} \quad (3a)$$

where $m_T$ is the total mass flow rate of the multiphase fluid 101, $C_d$ is the discharge coefficient, ε is the expansion factor, K is a fixed geometry factor ($K = A/\sqrt{1 - \beta^4}$, where A is the cross-sectional flow area of the Venturi-type flowmeter's neck (d) and β is the beta ratio (d/D, where d is the neck diameter of the Venturi-type flowmeter and D is the upstream pipe which converges with the Venturi-type flowmeter)), ΔP is measured pressure drop including frictional/shear pressure losses, $k_f$ is a geometry-based correction factor to account for difference(s) in the shape/geometry of the Venturi-type flowmeter (for example, as in apparatus 100A), $\Delta P_f$ is frictional/shear pressure losses (for example, measured by apparatus 100A and Equation 2h), and ρ is the mixture density of the multiphase fluid 101. The overall density (ρ) of the multiphase fluid 101 and frictional/shear pressure losses ($\Delta P_f$) determined by the apparatus 100A can, for example, be used in conjunction with the information obtained by the Venturi-type flowmeter (for example, total mass flow rate of the multiphase fluid 101, $m_T$) and be input to Equation 3a.

The operations performed by the processor 705 can include receiving, as input, a gas phase volume fraction ($\alpha_g$) of the multiphase fluid 101. The operations performed by the processor 705 can include receiving, as input, a gas phase density ($\rho_g$) of the gas phase 101a the multiphase fluid 101. The operations performed by the processor 705 can include receiving, as input, an aqueous phase density ($\rho_a$) of the aqueous phase 101b' of the multiphase fluid 101. The operations performed by the processor 705 can include receiving, as input, an oil phase density ($\rho_o$) of the oil phase 101b'' of the multiphase fluid 101. The operations performed by the processor 705 can include determining an aqueous phase volume fraction ($\alpha_a$) of the multiphase fluid 101 at least based on the gas phase volume fraction ($\alpha_g$), the gas density ($\rho_g$), the aqueous phase density ($\rho_a$), the oil phase density ($\rho_o$), and the overall density (ρ) of the multiphase fluid 101. For example, the gas phase volume fraction ($\alpha_g$), the gas density ($\rho_g$), the aqueous phase density ($\rho_a$), the oil phase density ($\rho_o$), and the overall density (ρ) of the multiphase fluid 101 can be input to Equation 3b and re-arranged to calculate the aqueous phase volume fraction ($\alpha_a$) of the multiphase fluid 101:

$$\rho = \rho_g \times \alpha_g + \rho_a \times \alpha_a + \rho_o \times (1 - \alpha_g - \alpha_a) \quad (3b)$$

The operations performed by the processor 705 can include receiving, as input, an aqueous phase volume fraction ($\alpha_a$) of the multiphase fluid 101. The operations performed by the processor 705 can include determining a gas phase volume fraction ($\alpha_g$) of the multiphase fluid 101 at least based on the aqueous phase volume fraction ($\alpha_a$), the gas density ($\rho_g$), the aqueous phase density ($\rho_a$), the oil phase density ($\rho_o$), and the overall density ($\rho$) of the multiphase fluid 101. For example, the aqueous phase volume fraction ($\alpha_a$), the gas density ($\rho_g$), the aqueous phase density ($\rho_a$), the oil phase density ($\rho_o$), and the overall density ($\rho$) of the multiphase fluid 101 can be input to Equation 3b and re-arranged to calculate the gas phase volume fraction ($\alpha_g$) of the multiphase fluid 101.

In some implementations, the first pair of pressure sensors 104a, 104b and the second pair of pressure sensors 104c, 104d measure the first differential pressure and the second differential pressure, respectively, of the multiphase fluid 101 flowing through the U-bend 102 multiple times across a time duration. Each of the first differential pressures and each of the second differential pressures measured by the first pair of pressure sensors 104a, 104b and the second pair of pressure sensors 104c, 104d, respectively, can be correlated to time points at which they were measured. Each of the first differential pressures and each of the second differential pressures measured by the first pair of pressure sensors 104a, 104b and the second pair of pressure sensors 104c, 104d, respectively, can take account for the time delay of the multiphase fluid 101 taking time to travel from the first conduit 102a (where the first pair of pressure sensors 104a, 104b are located), through the connecting conduit 102c, and to the second conduit 102b (where the second pair of pressure sensors 104c, 104d are located). For example, the measured differential pressures can be time-corrected to account for the delay in the multiphase fluid 101 traveling through the U-bend 102. The time-series data can, for example, be stored in the memory 707. The time-series data can, for example, be used to train and/or build a neural network-based classification model, which can be used to accurately identify flow regimes (for example, bubble flow, mist flow, slug flow, churn flow, annular flow, stratified flow, or intermittent flow). For example, the time-series data can be converted into a spectrogram (for example, by using a Morlet wavelet transform), and a single-layer two-dimensional image can be compiled from the spectrogram. A neural network (machine learning model) can then analyze the image and identify the flow regime of the multiphase fluid 101 flowing through the U-bend 102, for example, based on comparison to historical data. The time-series data can, for example, be used to train and/or build a neural network-based classification model, which can be used to estimate bulk flow velocity of the multiphase fluid 101 flowing through the U-bend 102. For example, the time-series data can be converted into a spectrogram (for example, by using a Morlet wavelet transform), and a single-layer two-dimensional image can be compiled from the spectrogram. A neural network (machine learning model) can then analyze the image and estimate the bulk flow velocity and/or flow rate of the multiphase fluid 101 flowing through the U-bend 102, for example, based on comparison to historical data.

Figure 1B:
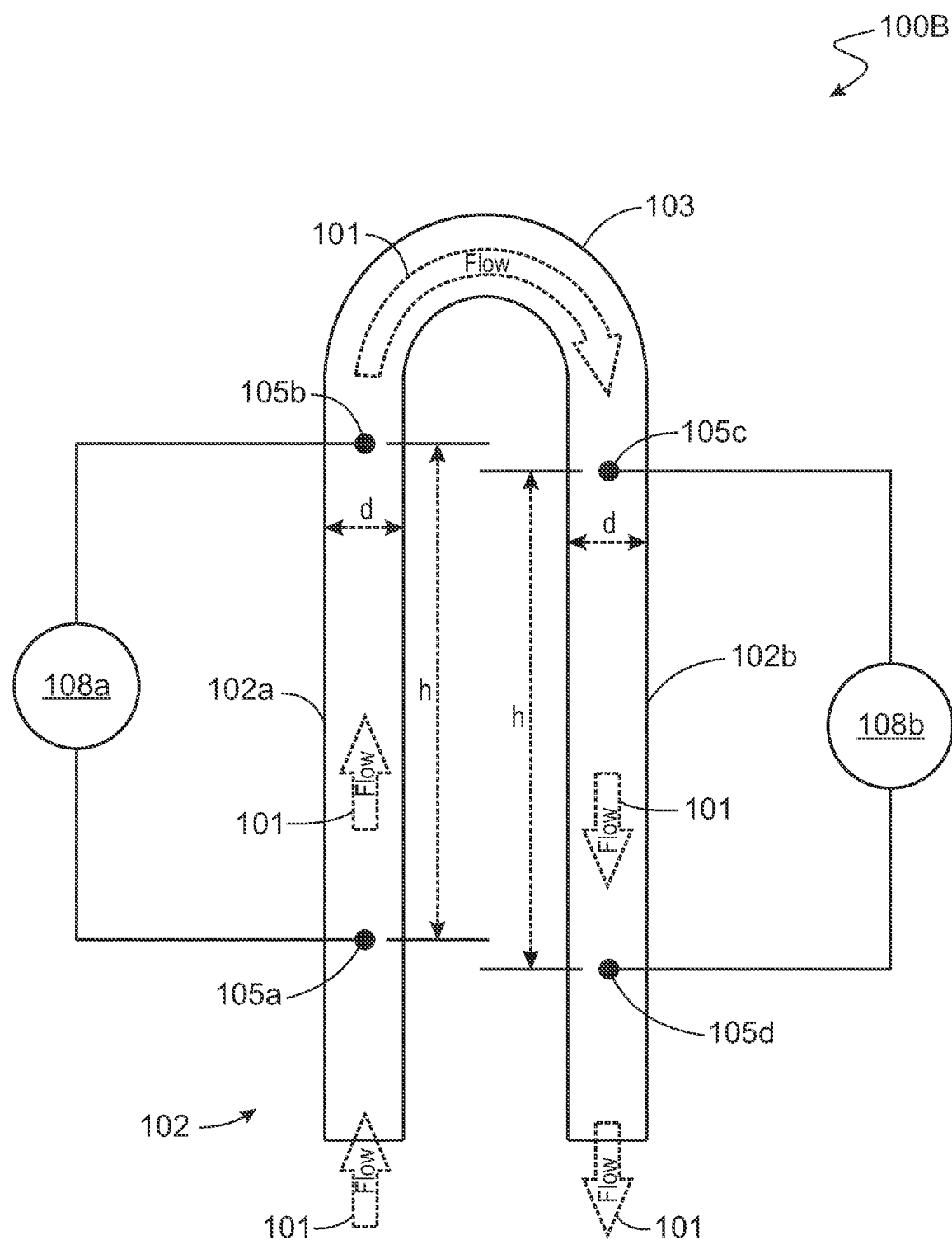
FIG. 1B is a schematic diagram of an example apparatus which can be used to measure a density of a multiphase fluid.

FIG. 1B depicts an apparatus 100B which can be used to measure a density of a multiphase fluid 101. The apparatus 100B can be substantially similar to the apparatus 100A shown in FIG. 1A. In comparison, the apparatus 100B omits the connecting conduit (102c shown in FIG. 1A). The apparatus 100B includes the U-bend 102, which includes the first conduit 102a and the second conduit 102b. The first conduit 102a is connected to the second conduit 102b by a curved bend 103. In some implementations, the first conduit 102a, the second conduit 102b, and the curved bend 103 are integrated, such that the U-bend 102 is a singular, unitary body, as opposed to parts that are disjointed and coupled together to form the U-bend 102. The curved bend 103 can be made of the same material as the first conduit 102a and the second conduit 102b, such that the friction experienced by the multiphase fluid 101 flowing through each of the components of the U-bend 102 is substantially the same.

The apparatus 100B can include a first differential pressure sensor 108a coupled to the first conduit 102a via pressure ports 105a and 105b. The first differential pressure sensor 108a is configured to measure a first differential pressure of the multiphase fluid 101 flowing through the U-bend 102. The pressure ports 105a and 105b are separated by the specified differential pressure height, h, with respect to gravity. The apparatus 100B can include a second differential pressure sensor 108b coupled to the second conduit 102b via pressure ports 105c and 105d. The second differential pressure sensor 108b is configured to measure a second differential pressure of the multiphase fluid 101 flowing through the U-bend 102. The pressure ports 105c and 105d are separated by the specified differential pressure height, h, with respect to gravity. As shown in FIG. 1B, the pressure port 105a does not necessarily need to be at the same vertical height as pressure port 105d, and the pressure port 105b does not necessarily need to be at the same vertical height as pressure port 105c. Instead, the vertical distance between pressure port 105a and pressure port 105b should match the vertical distance between pressure port 105c and pressure port 105d. The height difference between the pressure ports 105a, 105b of the first differential pressure sensor 108a and the height difference between the pressure ports 105c, 105d of the second differential pressure sensor 108b are the same, such that the frictional components of the pressure drops experienced by the multiphase fluid 101 flowing through the first conduit 102a (measured by the first differential pressure sensor 108a) and through the second conduit 102b (measured by the second differential pressure sensor 108b) are substantially the same.

Although not shown in FIG. 1B, the apparatus 100B can be coupled to a flow pipe (such as the flow pipe 150 shown in FIG. 1A), for example, by angled or curved bends. Although not shown in FIG. 1B, the first and second differential pressure sensors 108a, 108b can be coupled to a computer (such as the computer 700), to determine characteristics (such as a mixture density, a total mass flow rate, an aqueous phase volume fraction, a gas phase volume fraction, or any combination of these) of the multiphase fluid 101 flowing through the U-bend 102 (for example, using Equations 1, 1a, 1b, 2a, 2b, 2c, 2d, 2e, 2f, 2g, 2h, 3a, 3b, or any combination of these).

Figure 1C:
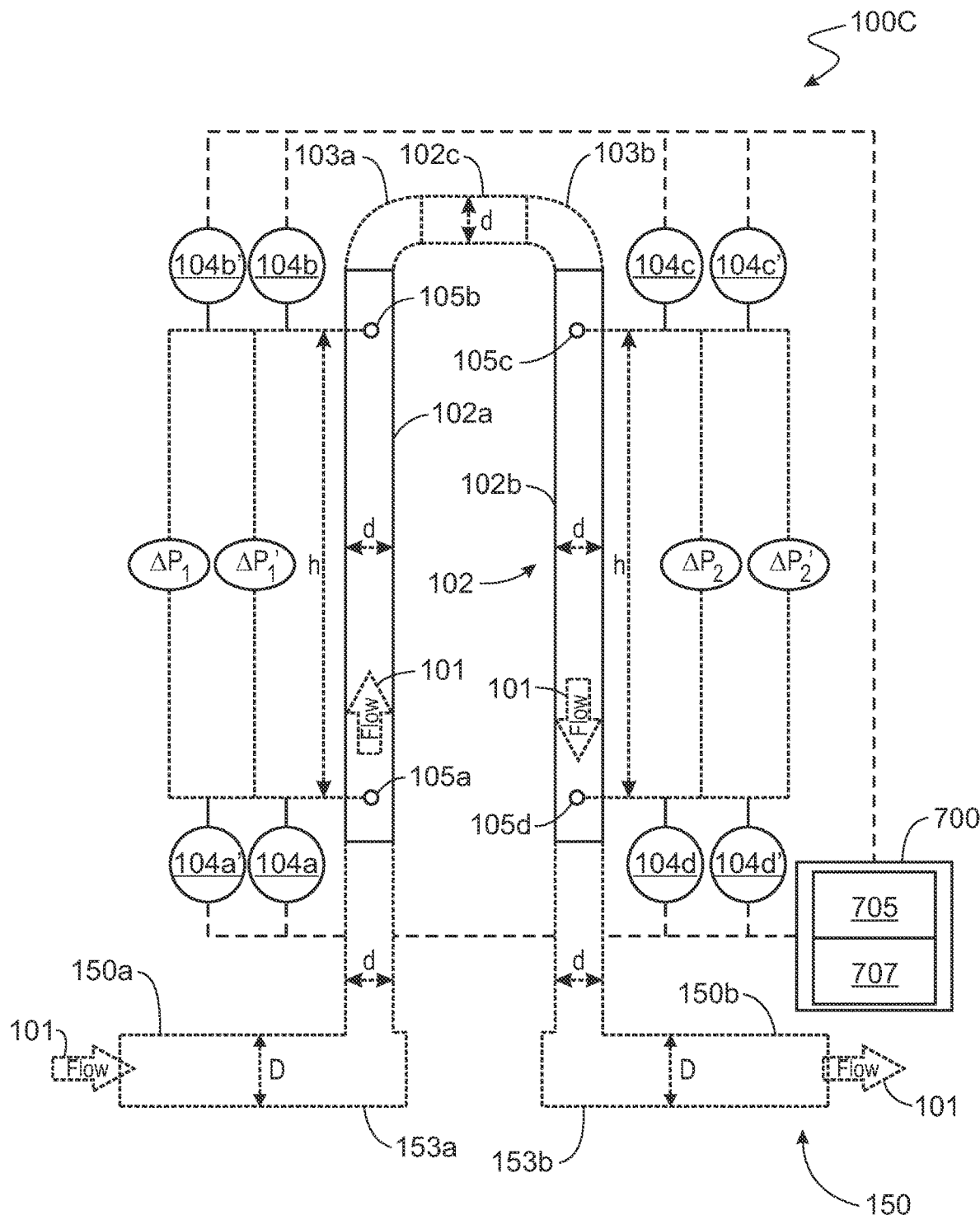
FIG. 1C is a schematic diagram of an example apparatus which can be used to measure a density of a multiphase fluid.

FIG. 1C depicts an apparatus 100C which can be used to measure a density of a multiphase fluid 101. The apparatus 100C can be substantially similar to the apparatus 100A shown in FIG. 1A. In comparison, the apparatus 100C includes multiple pairs of pressure sensors coupled to the first conduit 102a and multiple pairs of pressure sensors coupled to the second conduit 102b. The apparatus 100C shown in FIG. 1C includes two pairs of pressure sensors (104a, 104b and 104a', 104b') coupled to the first conduit 102a installed in a parallel configuration, but can, in other embodiments, include additional pairs of pressure sensors. The apparatus 100C shown in FIG. 1C includes two pairs of pressure sensors (104c, 104d and 104c', 104d') coupled to the second conduit 102b installed in a parallel configuration, but can, in other embodiments, include additional pairs of pressure sensors. The redundancy in pressure sensors can be useful in providing more accurate pressure measurements (for example, by averaging the measured pressures). The redundancy in pressure sensors can also be useful in identifying malfunctions in one or more of the pressure sensors, for example, if one or more of the pressure sensors provide pressure readings that deviate from the remaining pressure sensors by more than a threshold deviation. In some implementations, each pair of pressure sensors can be replaced by a differential pressure sensor. For example, the pair of pressure sensors 104a, 104b can be replaced by a first differential pressure sensor, the pair of pressure sensors 104a', 104b' can be replaced by a second differential pressure sensor, the pair of pressure sensors 104c, 104d can be replaced by a third differential pressure sensor, and the pair of pressure sensors 104c', 104d' can be replaced by a fourth differential pressure sensor. The redundancy in differential pressure sensors can be useful in providing a wider range of measurements (for example, by using sensors with different, but overlapping ranges).

Figure 1D:
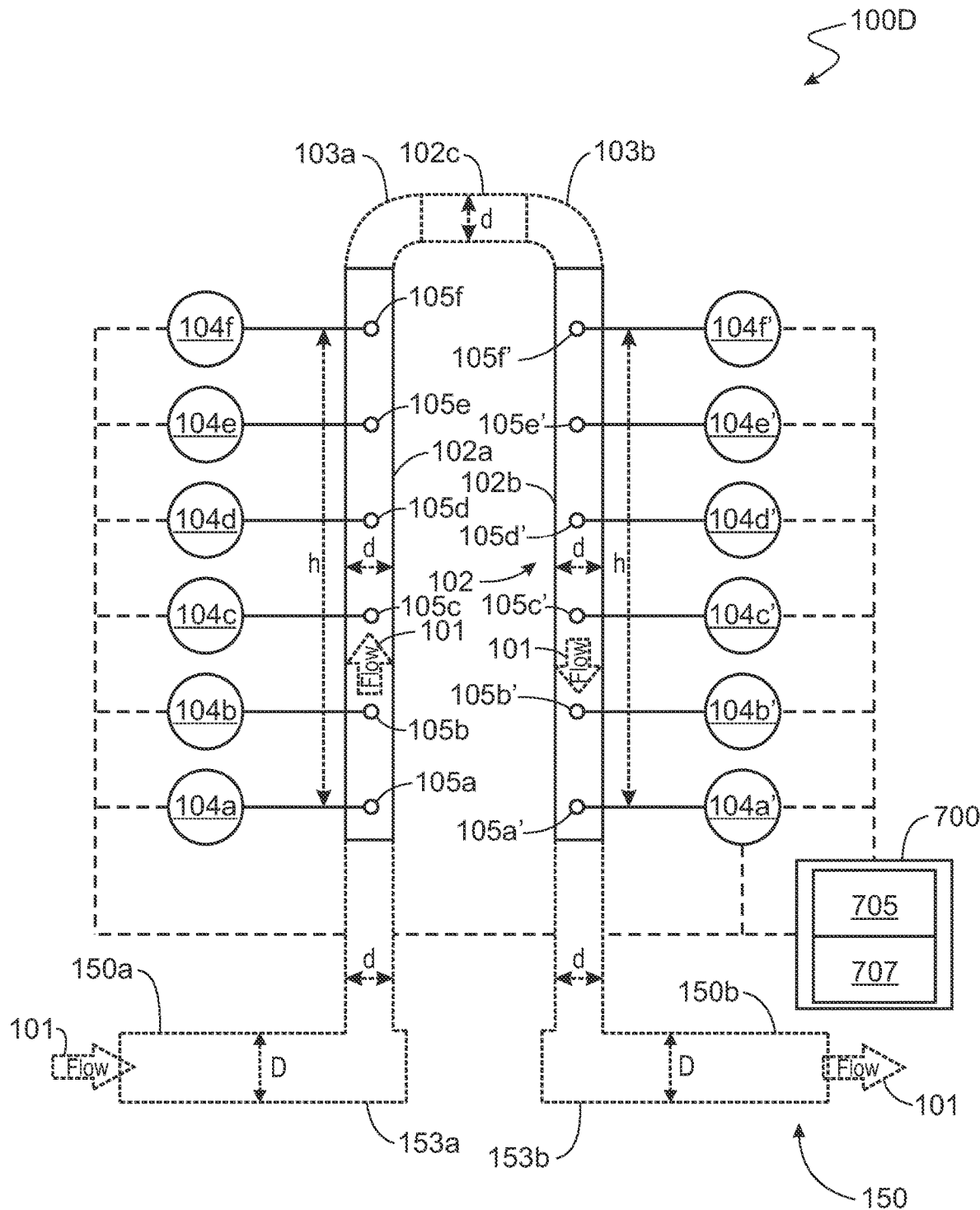
FIG. 1D is a schematic diagram of an example apparatus which can be used to measure a density of a multiphase fluid.

FIG. 1D depicts an apparatus 100D which can be used to measure a density of a multiphase fluid 101. The apparatus 100D can be substantially similar to the apparatus 100A shown in FIG. 1A. In comparison, the apparatus 100D includes more than two pressure sensors coupled to the first conduit 102a and more than two pressure sensors coupled to the second conduit 102b. Although shown in FIG. 1D as including six pressure sensors (104a, 104b, 104c, 104d, 104e, 104f) coupled to the first conduit 102a, the apparatus 100D can include fewer pressure sensors (such as three, four, or five) or more pressure sensors (such as seven or more than seven) coupled to the second conduit 102b. Although shown in FIG. 1D as including six pressure sensors (104a', 104b', 104c', 104d', 104e', 104f) coupled to the second conduit 102b, the apparatus 100D can include fewer pressure sensors (such as three, four, or five) or more pressure sensors (such as seven or more than seven) coupled to the second conduit 102b. Ideally, the apparatus 100D would include the same number of pressure sensors coupled to the first conduit 102a as coupled to the second conduit 102b. As shown in FIG. 1D, the pressure sensors (104a, 104b, 104c, 104d, 104e, 104f are installed on the first conduit 102a in a series configuration, and the pressure sensors (104a', 104b', 104c', 104d', 104e', 104f) are installed on the second conduit 102b in a series configuration.

In some cases, the pressure sensors 104a and 104b can be considered a first pair for the first conduit 102a, corresponding to the pressure sensors 104a' and 104b' as a corresponding first pair for the second conduit 102b. In some cases, the pressure sensors 104b and 104c can be considered a second pair for the first conduit 102a, corresponding to the pressure sensors 104b' and 104c' as a corresponding second pair for the second conduit 102b. In some cases, the pressure sensors 104c and 104d can be considered a third pair for the first conduit 102a, corresponding to the pressure sensors 104c' and 104d' as a corresponding third pair for the second conduit 102b. In some cases, the pressure sensors 104d and 104e can be considered a fourth pair for the first conduit 102a, corresponding to the pressure sensors 104d' and 104e' as a corresponding fourth pair for the second conduit 102b. In some cases, the pressure sensors 104e and 104f can be considered a fifth pair for the first conduit 102a, corresponding to the pressure sensors 104e' and 104f' as a corresponding fifth pair for the second conduit 102b. These pairs can be used to measure a piecewise pressure gradient along the first and second conduits 102a, 102b. This piecewise pressure gradient data can, for example, be averaged to more accurately calculate the density of the multiphase fluid 101 flowing through the U-bend.

In some cases, the pressure sensors 104a and 104c can be considered a first pair for the first conduit 102a, corresponding to the pressure sensors 104a' and 104c' as a corresponding first pair for the second conduit 102b. In some cases, the pressure sensors 104b and 104d can be considered a second pair for the first conduit 102a, corresponding to the pressure sensors 104b' and 104d' as a corresponding second pair for the second conduit 102b. In some cases, the pressure sensors 104c and 104e can be considered a third pair for the first conduit 102a, corresponding to the pressure sensors 104c' and 104e' as a corresponding third pair for the second conduit 102b. In some cases, the pressure sensors 104d and 104f can be considered a fourth pair for the first conduit 102a, corresponding to the pressure sensors 104d' and 104f' as a corresponding fourth pair for the second conduit 102b. Similarly, these pairs can be used to measure a piecewise pressure gradient along the first and second conduits 102a, 102b. This piecewise pressure gradient data can, for example, be averaged to more accurately calculate the density of the multiphase fluid 101 flowing through the U-bend.

In some cases, the pressure sensors 104a and 104d can be considered a first pair for the first conduit 102a, corresponding to the pressure sensors 104a' and 104d' as a corresponding first pair for the second conduit 102b. In some cases, the pressure sensors 104b and 104e can be considered a second pair for the first conduit 102a, corresponding to the pressure sensors 104b' and 104e' as a corresponding second pair for the second conduit 102b. In some cases, the pressure sensors 104c and 104f can be considered a third pair for the first conduit 102a, corresponding to the pressure sensors 104c' and 104f' as a corresponding third pair for the second conduit 102b. Similarly, these pairs can be used to measure a piecewise pressure gradient along the first and second conduits 102a, 102b. This piecewise pressure gradient data can, for example, be averaged to more accurately calculate the density of the multiphase fluid 101 flowing through the U-bend.

In some cases, the pressure sensors 104a and 104e can be considered a first pair for the first conduit 102a, corresponding to the pressure sensors 104a' and 104e' as a corresponding first pair for the second conduit 102b. In some cases, the pressure sensors 104b and 104f can be considered a second pair for the first conduit 102a, corresponding to the pressure sensors 104b' and 104f' as a corresponding second pair for the second conduit 102b. Similarly, these pairs can be used to measure a piecewise pressure gradient along the first and second conduits 102a, 102b. This piecewise pressure gradient data can, for example, be averaged to more accurately calculate the density of the multiphase fluid 101 flowing through the U-bend.

In some cases, the pressure sensors 104a and 104f can be considered a first pair for the first conduit 102a, corresponding to the pressure sensors 104a' and 104f' as a corresponding first pair for the second conduit 102b. In such cases, the apparatus 100D is substantially the same as the apparatus 100A shown in FIG. 1A. Any combinations or sub-combinations of the aforementioned pairs or pressure sensors can be considered as suitable implementations of the apparatus 100D.

In some implementations, any pair of pressure sensors coupled to the first tubular 102a can be replaced by a differential pressure sensor. For example, the pair of pressure sensors 104a, 104b can be replaced by a differential pressure sensor. For example, the pair of pressure sensors 104a, 104c can be replaced by a differential pressure sensor. For example, the pair of pressure sensors 104a, 104d can be replaced by a differential pressure sensor. For example, the pair of pressure sensors 104a, 104e can be replaced by a differential pressure sensor. For example, the pair of pressure sensors 104a, 104f can be replaced by a differential pressure sensor. For example, the pair of pressure sensors 104b, 104c can be replaced by a differential pressure sensor. For example, the pair of pressure sensors 104b, 104d can be replaced by a differential pressure sensor. For example, the pair of pressure sensors 104b, 104e can be replaced by a differential pressure sensor. For example, the pair of pressure sensors 104b, 104f can be replaced by a differential pressure sensor. For example, the pair of pressure sensors 104c, 104d can be replaced by a differential pressure sensor. For example, the pair of pressure sensors 104c, 104e can be replaced by a differential pressure sensor. For example, the pair of pressure sensors 104c, 104f can be replaced by a differential pressure sensor. For example, the pair of pressure sensors 104d, 104e can be replaced by a differential pressure sensor. For example, the pair of pressure sensors 104d, 104f can be replaced by a differential pressure sensor. For example, the pair of pressure sensors 104e, 104f can be replaced by a differential pressure sensor.

In some implementations, any pair of pressure sensors coupled to the second tubular 102b can be replaced by a differential pressure sensor. For example, the pair of pressure sensors 104a', 104b' can be replaced by a differential pressure sensor. For example, the pair of pressure sensors 104a', 104c' can be replaced by a differential pressure sensor. For example, the pair of pressure sensors 104a', 104d' can be replaced by a differential pressure sensor. For example, the pair of pressure sensors 104a', 104e' can be replaced by a differential pressure sensor. For example, the pair of pressure sensors 104a', 104f' can be replaced by a differential pressure sensor. For example, the pair of pressure sensors 104b', 104c' can be replaced by a differential pressure sensor. For example, the pair of pressure sensors 104b', 104d' can be replaced by a differential pressure sensor. For example, the pair of pressure sensors 104b', 104e' can be replaced by a differential pressure sensor. For example, the pair of pressure sensors 104b', 104f' can be replaced by a differential pressure sensor. For example, the pair of pressure sensors 104c', 104d' can be replaced by a differential pressure sensor. For example, the pair of pressure sensors 104c', 104e' can be replaced by a differential pressure sensor. For example, the pair of pressure sensors 104c', 104f' can be replaced by a differential pressure sensor. For example, the pair of pressure sensors 104d', 104e' can be replaced by a differential pressure sensor. For example, the pair of pressure sensors 104d', 104f' can be replaced by a differential pressure sensor. For example, the pair of pressure sensors 104e', 104f' can be replaced by a differential pressure sensor.

Figure 1E:
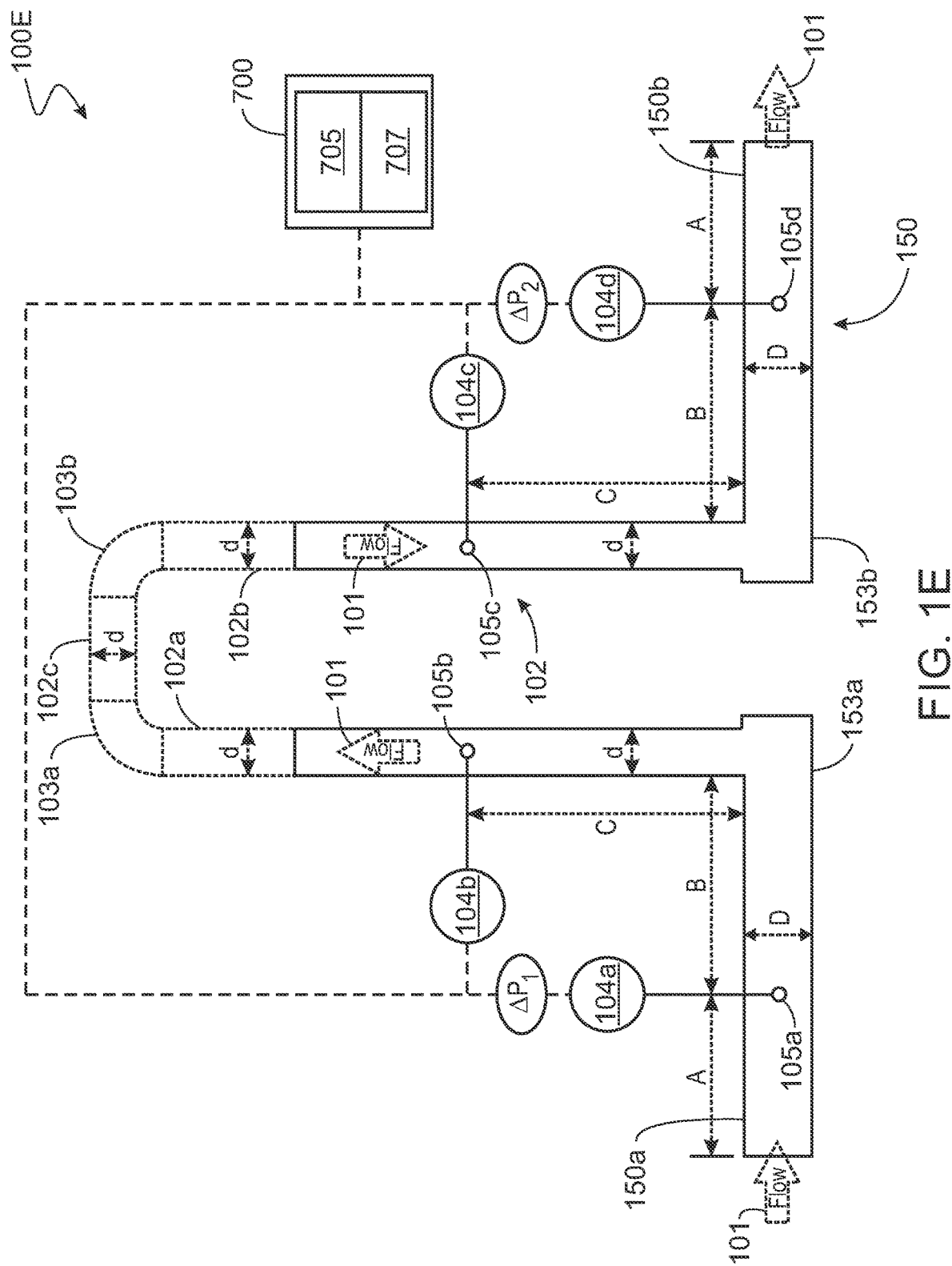
FIG. 1E is a schematic diagram of an example apparatus which can be used to measure a flow rate of a multiphase fluid.

FIG. 1E depicts an apparatus 100E which can be used to measure a total mass flow rate of a multiphase fluid 101. The apparatus 100E can be substantially similar to the apparatus 100A shown in FIG. 1A. The first pair of pressure sensors 104a, 104b and the second pair of pressure sensors 104c, 104d are located at different locations on the apparatus 100E in comparison to the apparatus 100A. The first pressure sensor 104a is coupled to the pressure port 105a on the first pipe 150a (third conduit) of the flow pipe 150. The second pressure sensor 104b is coupled to the pressure port 105b on the first conduit 102a of the U-bend 102. The third pressure sensor 104c is coupled to the pressure port 105c on the second conduit 102b of the U-bend 102. The fourth pressure sensor 104d is coupled to pressure port 105d on the second pipe 150b (fourth conduit) of the flow pipe 150. In some implementations, the first pair of pressure sensors 104a, 104b is replaced by a first differential pressure sensor. In some implementations, the second pair of pressure sensors 104c, 104d is replaced by a second differential pressure sensor.

The first pair of pressure sensors 104a, 104b (or first differential pressure sensor) are configured to measure a first differential pressure of the multiphase fluid 101. The first differential pressure includes the pressure losses of the multiphase fluid 101 flowing through the first angled bend 153a. The second pair of pressure sensors 104c, 104d (or second differential pressure sensor) are configured to measure a second differential pressure of the multiphase fluid 101. The second differential pressure includes the pressure losses of the multiphase fluid 101 flowing through the second angled bend 153b. The operations performed by the processor 705 can include receiving a first differential pressure signal from the first pair of pressure sensors 104a, 104b (or first differential pressure sensor). The first differential pressure signal can represent the first differential pressure of the multiphase fluid 101 measured by the pressure sensors 104a, 104b (or first differential pressure sensor). The operations performed by the processor 705 can include receiving a second differential pressure signal from the second pair of pressure sensors 104c, 104d (or second differential pressure sensor). The second differential pressure signal can represent the second differential pressure of the multiphase fluid 101 measured by the pressure sensors 104c, 104d (or second differential pressure sensor). The operations performed by the processor 705 can include determining an overall flow rate of the multiphase fluid 101 at least based on the first differential pressure, the second differential pressure, a difference between the first differential pressure and the second differential pressure of the multiphase fluid 101 and the overall density of the multiphase fluid 101. The overall density of the multiphase fluid 101 can be measured, for example, by a separate multiphase flowmeter. For example, the apparatus 100E can include features from the apparatus 100A, which can be used to determine the mixture density ($\rho$) of the multiphase fluid 101.

The overall flow rate of the multiphase fluid 101 can be determined in various ways. As a first example, the overall flow rate of the multiphase fluid 101 (ignoring frictional pressure loss) can be determined using the first differential pressure by Equation 4a:

$$m_{T1} = C_{d1} \times \varepsilon_1 \times K_1 \times \sqrt{2 \times \rho \times (\Delta P_1 - \rho \times g \times h_v)} \quad (4a)$$

where $m_{T1}$ is the total mass flow rate of the multiphase fluid 101, $C_{d1}$ is an empirically characterized discharge coefficient, $\varepsilon_1$ is an expansion factor, $K_1$ is a fixed geometry factor ($K_1 = A_1/\sqrt{1-\beta_1^4}$, where $A_1$ is the cross-sectional flow area of the throat of the first angled bend 153a and $\beta_1$ is the beta ratio (d/D, where d is the inner diameter of the first conduit 102a and D is the inner diameter of the first pipe 150a)), $\Delta P_1$ is the first differential pressure measured by the pressure sensors 104a, 104b (or the first differential pressure sensor), $\rho$ is the mixture density of the multiphase fluid 101, g is the acceleration due to gravity, and $h_v$ is the vertical height difference between the pressure ports 105a, 105b to which the pressure sensors 104a, 104b (or the first differential pressure sensor) are coupled. The discharge coefficient ($C_{d1}$) can be determined empirically, for example, based on historical data or correcting with real-time data.

As a second example, the total mass flow rate of the multiphase fluid 101 (ignoring frictional pressure loss) can be determined using the second differential pressure by Equation 4b:

$$m_{T2} = C_d \times \varepsilon_2 \times K_2 \times \sqrt{2 \times \rho \times (\Delta P_2 + \rho \times g \times h_v)} \tag{4b}$$

where $m_{T2}$ is the total mass flow rate of the multiphase fluid 101, $C_{d2}$ is an empirically characterized discharge coefficient, $\varepsilon_2$ is an expansion factor, $K_2$ is a fixed geometry factor ($K_2 = A_2/\sqrt{1-\beta_2^4}$, where $A_2$ is the cross-sectional flow area of the throat of the second angled bend 153b and $\beta_2$ is the beta ratio (D/d, where d is the inner diameter of the second conduit 102b and D is the inner diameter of the second pipe 150b)), $\Delta P_2$ is the second differential pressure measured by the pressure sensors 104c, 104d (or the second differential pressure sensor), $\rho$ is the mixture density of the multiphase fluid 101, g is the acceleration due to gravity, and $h_v$ is the vertical height difference between the pressure ports 105c, 105d to which the pressure sensors 104c, 104d (or the second differential pressure sensor) are coupled. The discharge coefficient ($C_{d2}$) can be determined empirically, for example, based on historical data or correcting with real-time data.

The operations performed by the processor 705 can include comparing the total mass flow rates ($m_{T1}$, $m_{T2}$) determined by Equations 4a and 4b to determine an adjustment of the discharge coefficients ($C_{d1}$, $C_{d2}$). Equation 4a can be re-written as: $m_{T1} = C_{d1} \times Y_1$, where $Y_1$ simply substitutes the right-hand side of Equation 4a (including measured parameters $\Delta P_1$ and $\rho$ and predetermined parameters $\varepsilon_1$ and $K_1$) excluding the discharge coefficient $C_{d1}$. Equation 4b can be re-written as: $m_{T2} = C_{d2} \times Y_2$, where $Y_2$ simply substitutes the right-hand side of Equation 4b (including measured parameters $\Delta P_2$ and $\rho$ and predetermined parameters $\varepsilon_2$ and $K_2$) excluding the discharge coefficient $C_{d1}$. Because the total mass flow rate does not change as the multiphase fluid 101 flows through the apparatus 100E, $m_{T1} = m_{T2}$. Thus, $C_{d1} \times Y_1 = C_{d2} \times Y_2$. Because of this relationship, given $C_{d1}$ and the measured parameters $Y_1$ and $Y_2$, $C_{d2}$ can be calculated. Similarly, given $C_{d2}$ and the measured parameters $Y_1$ and $Y_2$, $C_{d1}$ can be calculated. As such, the discharge coefficients ($C_{d1}$, $C_{d2}$) can be verified for consistency and accuracy, as an in situ self-check. Other techniques (such as least-squares minimization) can be additionally or alternatively used to accurately calculate the discharge coefficients ($C_{d1}$, $C_{d2}$).

The first differential pressure ($\Delta P_1$) measured by the pressure sensors 104a, 104b (or the first differential pressure sensor) and the second differential pressure ($\Delta P_2$) measured by the pressure sensors 104c, 104d (or the second differential pressure sensor) can be used to calculate the mixture density ($\rho$) of the multiphase fluid 101. Equation 4a can be re-arranged as Equation 5a:

$$\Delta P_1 - \rho \times g \times h_v = \frac{m_{T1}^2}{2 \times \rho \times (C_{d1} \times \varepsilon_1 \times K_1)^2} \tag{5a}$$

Equation 4b can be re-arranged as Equation 5b:

$$\Delta P_2 + \rho \times g \times h_v = \frac{m_{T2}^2}{2 \times \rho \times (C_{d2} \times \varepsilon_2 \times K_2)^2} \tag{5b}$$

As mentioned previously, the total mass flow rate does not change as the multiphase fluid 101 flows through the apparatus 100E, so $m_{T1} = m_{T2}$. For simplicity, the variable Z is defined by Equation 5c:

$$Z = \left(\frac{C_{d1} \times \varepsilon_1 \times K_1}{C_{d2} \times \varepsilon_2 \times K_2}\right)^2 \tag{5c}$$

Combining Equations 5a, 5b, and 5c and then solving for the mixture density ($\rho$) results in Equation 5d:

$$\rho = \frac{Z \times \Delta P_1 - \Delta P_2}{g \times (1 + Z)} \tag{5d}$$

Equation 5d can be used, for example, to verify the accuracy of the mixture density ($\rho$) determined by any one of apparatuses 100A, 100B, 100C, or 100D.

In some implementations, a distance between the first pressure sensor 104a and the second pressure sensor 104b is substantially the same as a distance between the third pressure sensor 104c and the fourth pressure sensor 104d. In a specific example, the apparatus 100E has the following dimensions. The inner diameter (d) of the U-bend 102 (the first conduit 102a, the second conduit 102b, and the connecting conduit 102c) is about 2.067 inches (nominal pipe size (NPS) 2" Schedule 40). The inner diameter (D) of the first pipe 150a and the second pipe 150b is about 3.068" (NPS 3" Schedule 40). The dimension A is the length of straight pipe (that is, pipe that is free of any bends) of the first pipe 150a upstream of the first pressure sensor 104a. The dimension A is also the length of straight pipe of the second pipe 150b downstream of the fourth pressure sensor 104d. The dimension A is a minimum length of straight pipe that ensures minimal interference of turbulence and friction which may affect the measurements taken by the first pair of pressure sensors 104a, 104b and the measurements taken by the second pair of pressure sensors 104c, 104d. In some implementations, the dimension A is at least five times the inner diameter (D) of the first pipe 150a (A≥5D). The dimension B is the length of straight pipe of the first pipe 150a downstream of the first pressure sensor 104a and upstream of the first angled bend 153a. The dimension B is also the length of straight pipe of the second pipe 150b downstream of the second angled bend 153b and upstream of the fourth pressure sensor 104d. Similarly, the dimension B is a minimum length of straight pipe that ensures minimal interference of turbulence and friction which may affect the measurements taken by the first pair of pressure sensors 104a, 104b and the measurements taken by the second pair of pressure sensors 104c, 104d. In some implementations, the dimension B is at least five times the inner diameter (D) of the first pipe 150a (B≥5D). The dimension C is the length of straight pipe of the first conduit 102a downstream of the first angled bend 153a and upstream of the second pressure sensor 104b. The dimension C is also the length of straight pipe of the second conduit 102b downstream of the third pressure sensor 104c and upstream of the second angled bend 153b. Similarly, the dimension C is a minimum length of straight pipe that ensures minimal interference of turbulence and friction which may affect the measurements taken by the first pair of pressure sensors 104a, 104b and the measurements taken by the second pair of pressure sensors 104c, 104d. In some implementations, the dimension C is at least five times the inner diameter (d) of the U-bend 102 (C≥5d).

Figure 1F:
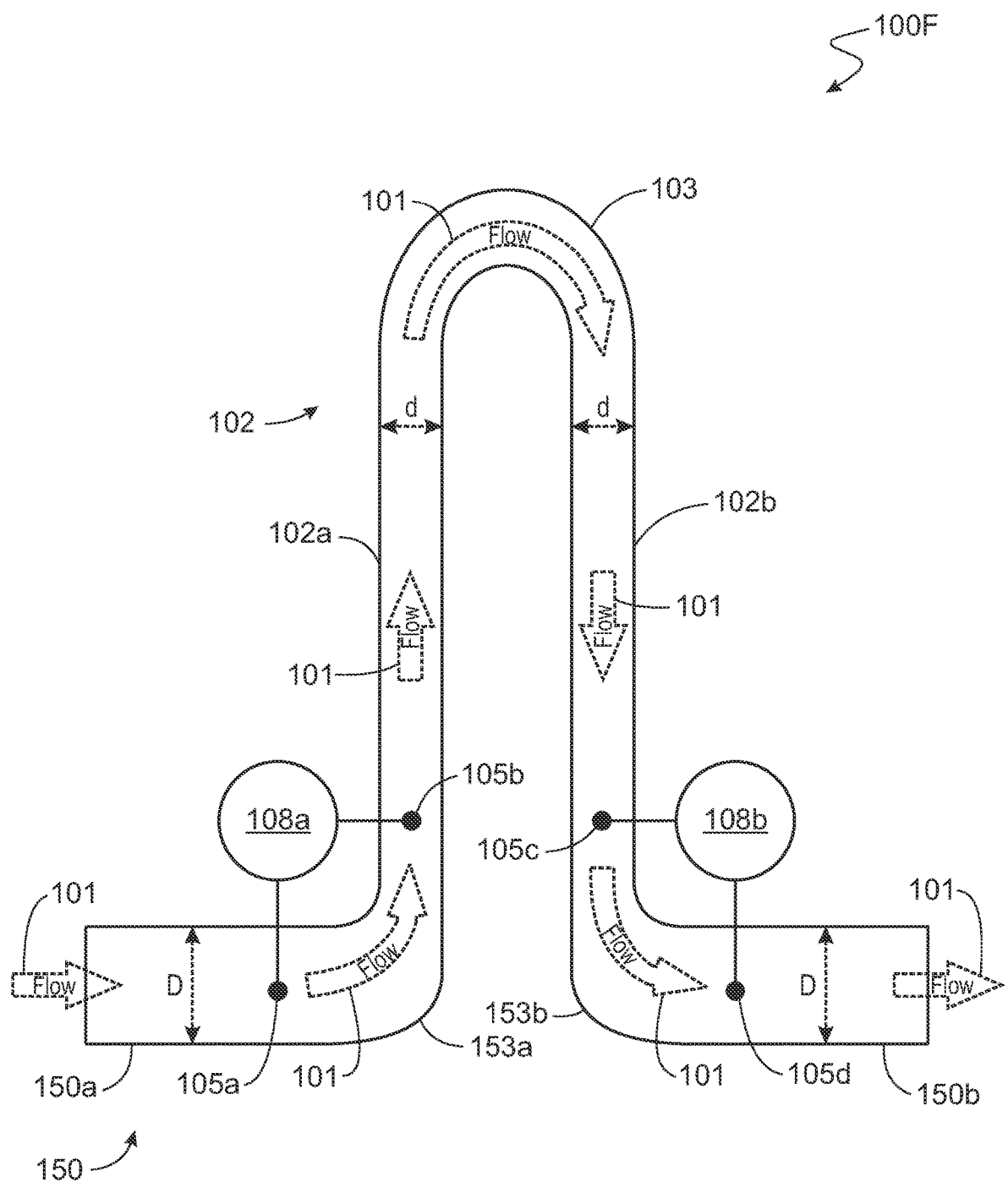
FIG. 1F is a schematic diagram of an example apparatus which can be used to measure a flow rate of a multiphase fluid.

FIG. 1F depicts an apparatus 100F which can be used to measure a total mass flow rate of a multiphase fluid 101. The apparatus 100F can be substantially similar to the apparatus 100E shown in FIG. 1E. In comparison, the apparatus 100F omits the connecting conduit (102c shown in FIG. 1E). The apparatus 100F includes the U-bend 102, which includes the first conduit 102a and the second conduit 102b. The first conduit 102a is connected to the second conduit 102b by a curved bend 103. In some implementations, the first conduit 102a, the second conduit 102b, and the curved bend 103 are integrated, such that the U-bend 102 is a singular, unitary body, as opposed to parts that are disjointed and coupled together to form the U-bend 102. The curved bend 103 can be made of the same material as the first conduit 102a and the second conduit 102b, such that the friction experienced by the multiphase fluid 101 flowing through each of the components of the U-bend 102 is substantially the same.

As shown in FIG. 1F, the U-bend 102 can be connected to a flow pipe 150 that flows the multiphase fluid 101. The flow pipe 150 includes the first pipe 150a and the second pipe 150b. In some implementations, the U-bend 102 is connected to the flow pipe 150 by curved bends 153c, 153d. For example, the first conduit 102a of the U-bend 102 is connected to the first pipe 150a of the flow pipe 150 by the first curved bend 153c. For example, the second conduit 102b of the U-bend 102 is connected to the second pipe 150b of the flow pipe 150 by the second curved bend 153d. In some implementations, the first conduit 102a, the second conduit 102b, the curved bend 103, the first curved bend 153c, the second curved bend 153d, and the flow pipe 150 are integrated, such that the U-bend 102 and the flow pipe 150 form a singular, unitary body, as opposed to parts that are disjointed and coupled together.

The apparatus 100F can include a first differential pressure sensor 108a coupled to the first pipe 150a and to the first conduit 102a via pressure ports 105a and 105b, respectively. The first differential pressure sensor 108a is configured to measure a first differential pressure of the multiphase fluid 101 flowing across the first curved bend 153c. The pressure ports 105a and 105b are separated by the specified differential pressure height, h, with respect to gravity. The apparatus 100B can include a second differential pressure sensor 108b coupled to the second conduit 102b and to the second pipe 150b via pressure ports 105c and 105d, respectively. The second differential pressure sensor 108b is configured to measure a second differential pressure of the multiphase fluid 101 flowing across the second curved bend 153d. The pressure ports 105c and 105d are separated by the specified differential pressure height, h, with respect to gravity. As shown in FIG. 1F, the pressure port 105a does not necessarily need to be at the same vertical height as pressure port 105d, and the pressure port 105b does not necessarily need to be at the same vertical height as pressure port 105c. Instead, the vertical distance between pressure port 105a and pressure port 105b should match the vertical distance between pressure port 105c and pressure port 105d. The height difference between the pressure ports 105a, 105b of the first differential pressure sensor 108a and the height difference between the pressure ports 105c, 105d of the second differential pressure sensor 108b are the same, and the horizontal distance between the pressure ports 105a, 105b of the first differential pressure sensor 108a and the horizontal distance between the pressure ports 105c, 105d of the second differential pressure sensor 108b are the same, such that the frictional components of the pressure drops experienced by the multiphase fluid 101 flowing across the first curved bend 153c (measured by the first differential pressure sensor 108a) and through the second curved bend 153d (measured by the second differential pressure sensor 108b) are substantially the same.

Although not shown in FIG. 1F, the first and second differential pressure sensors 108a, 108b can be coupled to a computer (such as the computer 700), to determine characteristics (such as a mixture density, a total mass flow rate, or both) of the multiphase fluid 101 flowing through the U-bend 102 (for example, using Equations 4a, 4b, 5a, 5b, 5c, 5d, or any combination of these).

Figure 1G:
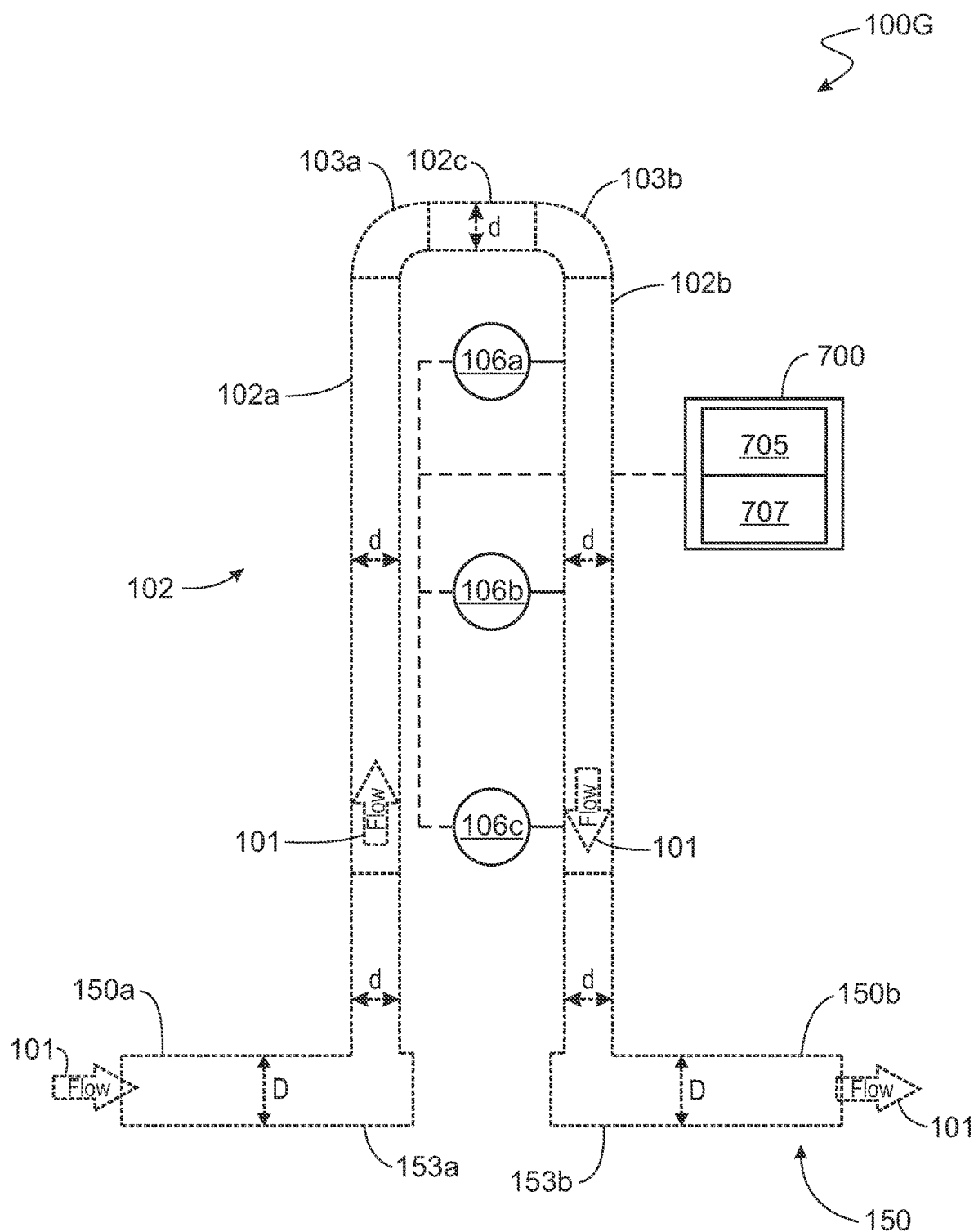
FIG. 1G is a schematic diagram of an example apparatus which can be used to measure a water-liquid ratio of a multiphase fluid.

FIG. 1G depicts an apparatus 100G which can be used to measure a water-liquid ratio of a multiphase fluid 101. The apparatus 100G can be substantially similar to the apparatus 100A shown in FIG. 1A. In comparison to the apparatus 100A, the apparatus 100G includes dynamic pressure sensors 106a, 106b, 106c that are coupled to the U-bend 102. Although shown in FIG. 1G as including three dynamic pressure sensors 106a, 106b, 106c, the apparatus 100G can include fewer dynamic pressure sensors (such as two dynamic pressure sensors) or more dynamic pressure sensors (such as four dynamic pressure sensors or more than four dynamic pressure sensors). The dynamic pressure sensors 106a, 106b, 106c measure a dynamic pressure of the multiphase fluid 101 flowing through the U-bend 102, as opposed to a static pressure of the multiphase fluid 101. The dynamic pressure sensors 106a, 106b, 106c can be located at any locations along the U-bend 102. In some implementations, the dynamic pressure sensors 106a, 106b, 106c are coupled to the first conduit 102a of the U-bend 102. In some implementations, the dynamic pressure sensors 106a, 106b, 106c are coupled to the second conduit 102b of the U-bend 102. In some implementations, a first portion of the dynamic pressure sensors 106a, 106b, 106c (for example, one or two of the dynamic pressure sensors 106a, 106b, 106c) is coupled to the first conduit 102a of the U-bend 102, and a remaining portion of the dynamic pressure sensors 106a, 106b, 106c is coupled to the second conduit 102b of the U-bend 102. The dynamic pressure sensors 106a, 106b, 106c can be evenly or randomly distributed along the U-bend 102.

The dynamic pressure measurements taken by the dynamic pressure sensors 106a, 106b, 106c can be cross-correlated (for example, by the processor 705) to determine a speed of sound of the multiphase fluid 101 flowing through the U-bend 102. The speed of sound of the multiphase fluid 101 and the overall density ($\rho$) of the multiphase fluid 101 can then be used to determine the water-liquid ratio of the multiphase fluid 101. The water-liquid ratio of the multiphase fluid 101 is a ratio of a volume of the aqueous phase 101b' to a sum of the volume of the aqueous phase 101b' and a volume of the oil phase 101b" (liquid phase 101b) (that is, the ratio of (volume of 101b')/(volume of 101b'+volume of 101b"), which is the same as the ratio of (volume of 101b')/(volume of 101b)). For example, the speed of sound of the multiphase fluid 101 and the overall density ($\rho$) of the multiphase fluid 101 can be compared to a plotted graph of various phase curves (gas/oil, gas/aqueous, oil/aqueous) to determine the water-liquid ratio.

Figure 1H:
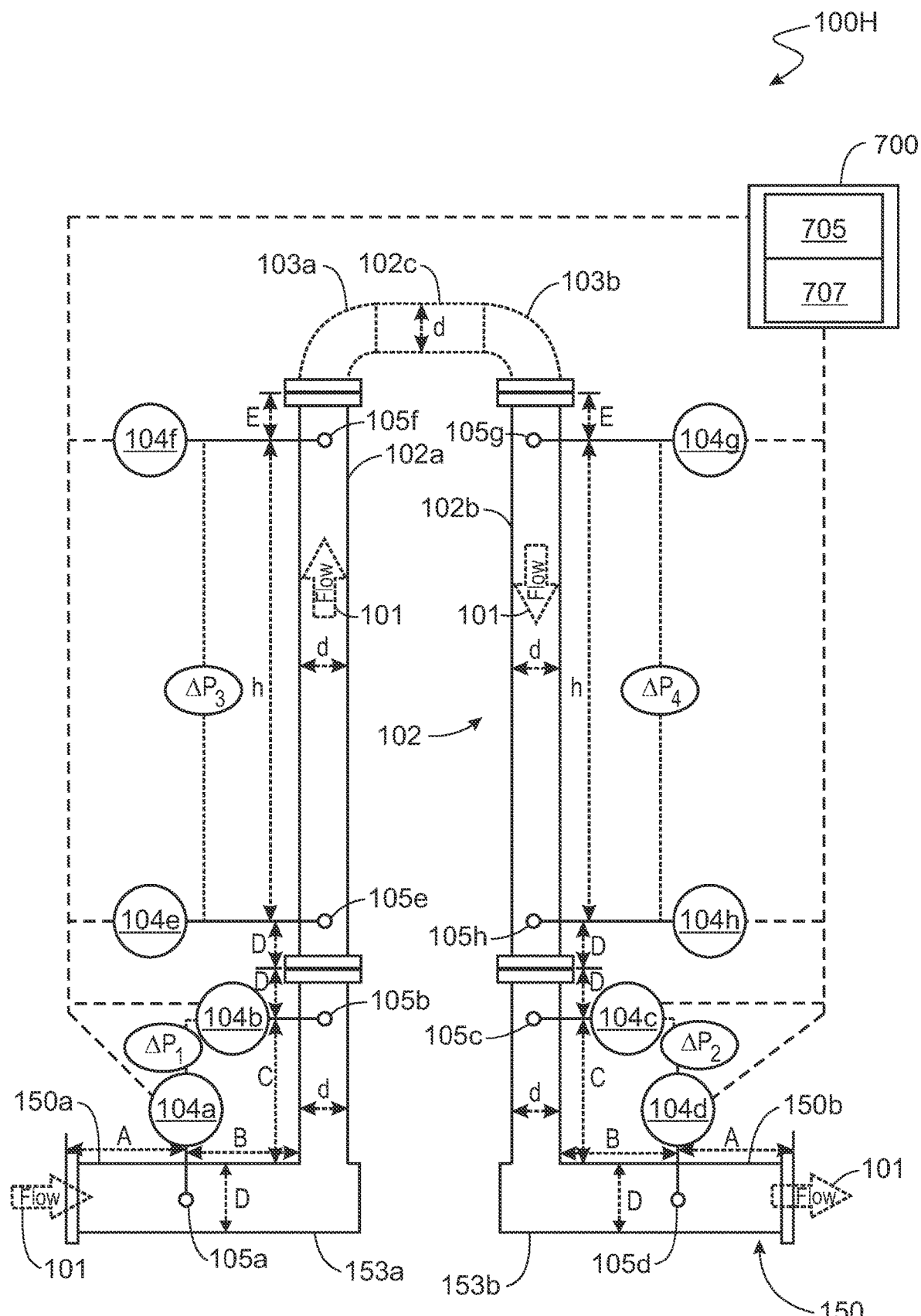
FIG. 1H is a schematic diagram of an example apparatus which can be used to measure a density and a flow rate of a multiphase fluid.

FIG. 1H depicts an apparatus 100H which can be used to measure a density, a total flow rate, and phase flow rates of a multiphase fluid 101. The apparatus 100H can be substantially similar to the apparatus 100A shown in FIG. 1A and the apparatus 100E shown in FIG. 1E. For example, the apparatus 100H can be a combination of the apparatus 100A and the apparatus 100E. The first pressure sensor 104a is coupled to a first pressure port 105a on the first pipe 150a (third conduit) of the flow pipe 150. The second pressure sensor 104b is coupled to a second pressure port 105b on the first conduit 102a of the U-bend 102. The third pressure sensor 104c is coupled to a third pressure port 105c on the second conduit 102b of the U-bend 102. The fourth pressure sensor 104d is coupled to a fourth pressure port 105d on the second pipe 150b (fourth conduit) of the flow pipe 150. The fifth and sixth pressure sensors 104e, 104f are coupled to fifth and sixth pressure ports 105e, 105f, respectively, on the first conduit 102a of the U-bend 102. The fifth and sixth pressure ports 105e, 105f are separated by the specified height, h, along the first conduit 102a. The seventh and eighth pressure sensors 104g, 104h are coupled to seventh and eighth pressure ports 105g, 105h, respectively, on the second conduit 102b of the U-bend 102. The seventh and eighth pressure ports 105g, 105h are separated by the specified height, h, along the second conduit 102b. In some implementations, the first and second pressure sensors 104a, 104b are replaced by a first differential pressure sensor. In some implementations, the third and fourth pressure sensors 104c, 104d are replaced by a second differential pressure sensor. In some implementations, the fifth and sixth pressure sensors 104e, 104f are replaced by a third differential pressure sensor. In some implementations, the seventh and eighth pressure sensors 104g, 104h are replaced by a fourth differential pressure sensor.

The first pair of pressure sensors 104a, 104b (or first differential pressure sensor) are configured to measure a first differential pressure of the multiphase fluid 101. The first differential pressure includes the pressure losses of the multiphase fluid 101 flowing through the first angled bend 153a. The second pair of pressure sensors 104c, 104d (or second differential pressure sensor) are configured to measure a second differential pressure of the multiphase fluid 101. The second differential pressure includes the pressure losses of the multiphase fluid 101 flowing through the second angled bend 153b. The third pair of pressure sensors 104e, 104f (or third differential pressure sensor) are configured to measure a third differential pressure of the multiphase fluid 101. The fourth pair of pressure sensors 104g, 104h (or fourth differential pressure sensor) are configured to measure a fourth differential pressure of the multiphase fluid 101. The operations performed by the processor 705 can include receiving a first differential pressure signal from the first pair of pressure sensors 104a, 104b (or first differential pressure sensor). The first differential pressure signal can represent the first differential pressure of the multiphase fluid 101 measured by the pressure sensors 104a, 104b (or first differential pressure sensor). The operations performed by the processor 705 can include receiving a second differential pressure signal from the second pair of pressure sensors 104c, 104d (or second differential pressure sensor). The second differential pressure signal can represent the second differential pressure of the multiphase fluid 101 measured by the pressure sensors 104c, 104d (or second differential pressure sensor). The operations performed by the processor 705 can include receiving a third differential pressure signal from the third pair of pressure sensors 104e, 104f (or third differential pressure sensor). The third differential pressure signal can represent the third differential pressure of the multiphase fluid 101 measured by the pressure sensors 104e, 104f (or third differential pressure sensor). The operations performed by the processor 705 can include receiving a fourth differential pressure signal from the fourth pair of pressure sensors 104g, 104h (or fourth differential pressure sensor). The fourth differential pressure signal can represent the fourth differential pressure of the multiphase fluid 101 measured by the pressure sensors 104g, 104h (or fourth differential pressure sensor). The operations performed by the processor 705 can include determining an overall density of the multiphase fluid 101 at least based on the specified height (h) and a difference between the third differential pressure and the fourth differential pressure. The operations performed by the processor 705 can include determining an overall flow rate of the multiphase fluid 101 at least based on the first differential pressure and the second differential pressure of the multiphase fluid 101 and the overall density of the multiphase fluid 101.

The mixture density of the multiphase fluid 101 can be determined in various ways. As a first example, the mixture density ($\rho$) of the multiphase fluid 101 can be determined by Equation 2d tailored for the apparatus 100H, where $\Delta P_1$ is the third differential pressure measured by the third pair of pressure sensors 104e, 104f (or third differential pressure sensor), $\Delta P_2$ is the fourth differential pressure measured by the fourth pair of pressure sensors 104g, 104h (or fourth differential pressure sensor), and $h_2$ is the specified height (h). As a second example, the mixture density ($\rho$) of the multiphase fluid 101 can be determined by Equation 5d tailored for the apparatus 100H, where $\Delta P_1$ is the third differential pressure measured by the third pair of pressure sensors 104e, 104f (or third differential pressure sensor) and $\Delta P_2$ is the fourth differential pressure measured by the fourth pair of pressure sensors 104g, 104h (or fourth differential pressure sensor).

The total flow rate of the multiphase fluid 101 can be determined in various ways. As a first example, the total flow rate of the multiphase fluid 101 can be determined using the first differential pressure by Equation 4a. As a second example, the total flow rate of the multiphase fluid 101 can be determined using the second differential pressure by Equation 4b. The operations performed by the processor 705 can include comparing the overall flow rates ($m_{T1}$, $m_{T2}$) determined by Equations 4a and 4bc to determine an adjustment of the discharge coefficients ($C_{d1}$, $C_{d2}$).

In some implementations, a distance between the first pressure sensor 104a and the second pressure sensor 104b is substantially the same as a distance between the third pressure sensor 104c and the fourth pressure sensor 104d. In a specific example, the apparatus 100D has the following dimensions. The inner diameter (d) of the U-bend 102 (the first conduit 102a, the second conduit 102b, and the connecting conduit 102c) is about 2.067 inches (NPS 2" Schedule 40). The inner diameter (D) of the first pipe 150a and the second pipe 150b is about 3.068" (NPS 3" Schedule 40). The dimension A is the length of straight pipe (that is, pipe that is free of any bends) of the first pipe 150a upstream of the first pressure sensor 104a. The dimension A is also the length of straight pipe of the second pipe 150b downstream of the fourth pressure sensor 104d. The dimension A is a minimum length of straight pipe that ensures minimal interference of turbulence and friction which may affect the measurements taken by the first pair of pressure sensors 104a, 104b and the measurements taken by the second pair of pressure sensors 104c, 104d. In some implementations, the dimension A is at least five times the inner diameter (D) of the first pipe 150a (A≥5D). The dimension B is the length of straight pipe of the first pipe 150a downstream of the first pressure sensor 104a and upstream of the first angled bend 153a. The dimension B is also the length of straight pipe of the second pipe 150*b* downstream of the second angled bend 153*b* and upstream of the fourth pressure sensor 104*d*. Similarly, the dimension B is a minimum length of straight pipe that ensures minimal interference of turbulence and friction which may affect the measurements taken by the first pair of pressure sensors 104*a*, 104*b* and the measurements taken by the second pair of pressure sensors 104*c*, 104*d*. In some implementations, the dimension B is at least five times the inner diameter (D) of the first pipe 150*a* (B≥5D). The dimension C is the length of straight pipe of the first conduit 102*a* downstream of the first angled bend 153*a* and upstream of the second pressure sensor 104*b*. The dimension C is also the length of straight pipe of the second conduit 102*b* downstream of the third pressure sensor 104*c* and upstream of the second angled bend 153*b*. Similarly, the dimension C is a minimum length of straight pipe that ensures minimal interference of turbulence and friction which may affect the measurements taken by the first pair of pressure sensors 104*a*, 104*b* and the measurements taken by the second pair of pressure sensors 104*c*, 104*d*. In some implementations, the dimension C is at least five times the inner diameter (d) of the U-bend 102 (C≥5d). In some implementations, there is a length of straight pipe between the second pressure sensor 104*b* and the fifth pressure sensor 104*e* of at least two times the inner diameter (d) of the U-bend 102 (≥2d) along the longitudinal length of the first conduit 102*a* of the U-bend 102. In some implementations, there is a length of straight pipe between the eighth pressure sensor 104*h* and the third pressure sensor 104*c* of at least two times the inner diameter (d) of the U-bend 102 (≥2d) along the longitudinal length of the second conduit 102*b* of the U-bend 102. The dimension E is the length of straight pipe of the first conduit 102*a* downstream of the sixth pressure sensor 104*f* and upstream of the first curved bend 103*a*. The dimension E is also the length of straight pipe of the second conduit 102*b* downstream of the second curved bend 103*b* and upstream of the seventh pressure sensor 104*g*. Similarly, the dimension E is a minimum length of straight pipe that ensures minimal interference of turbulence and friction which may affect the measurements taken by the third pair of pressure sensors 104*e*, 104*f* and the measurements taken by the fourth pair of pressure sensors 104*g*, 104*h*. In some implementations, the dimension E is at least five times the inner diameter (d) of the U-bend 102 (E≥5d).

Figure 1I:
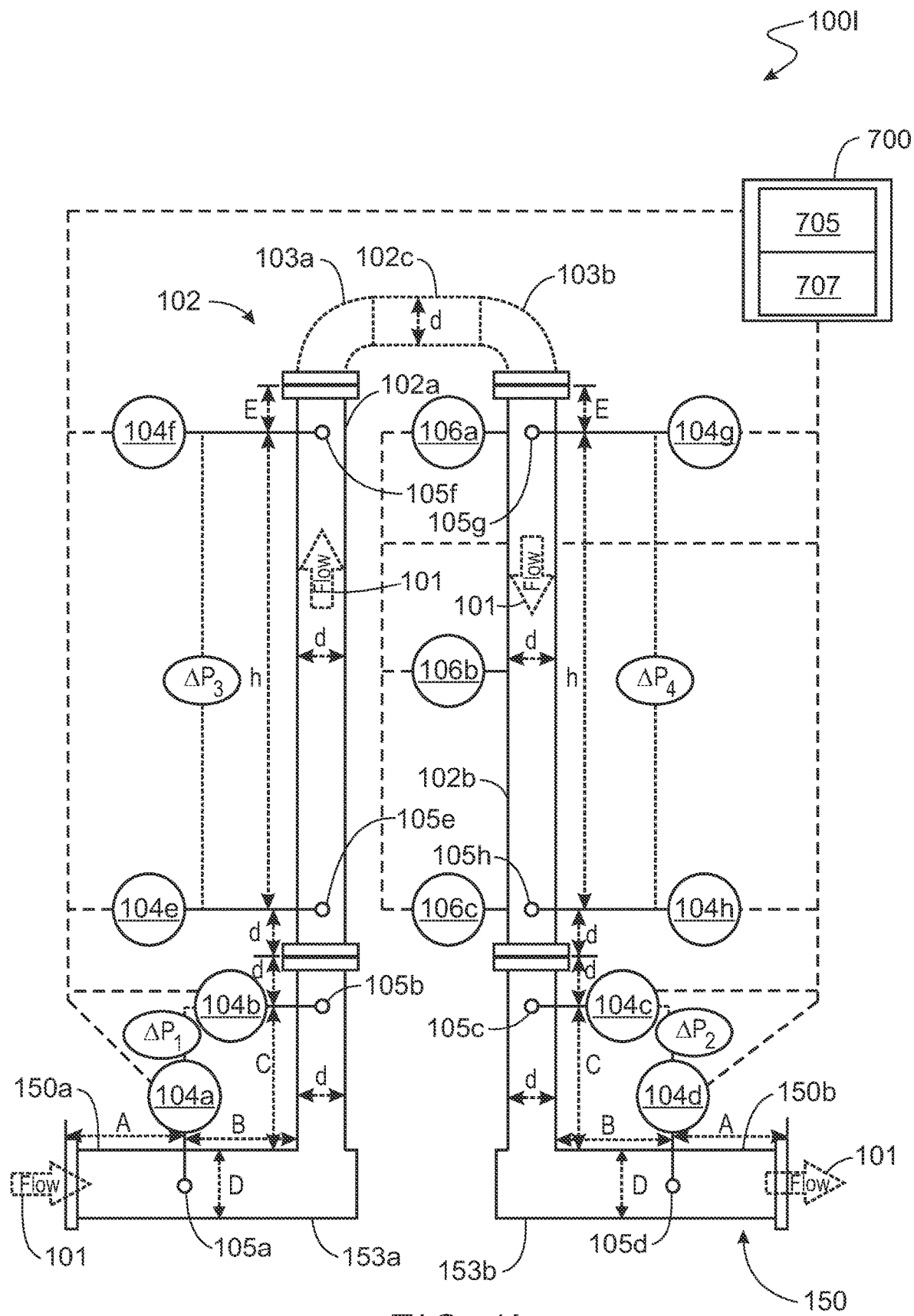
FIG. 1I is a schematic diagram of an example apparatus which can be used to measure a density, a flow rate, and a water-liquid ratio of a multiphase fluid.

FIG. 1I depicts an apparatus 100I which can be used to measure a density, a flow rate, and a water-liquid ratio of a multiphase fluid 101. The apparatus 100I can be substantially similar to the apparatus 100A shown in FIG. 1A, the apparatus 100E shown in FIG. 1E, the apparatus 100G shown in FIG. 1G, and the apparatus 100H shown in FIG. 1H. For example, the apparatus 100I can be a combination of the apparatus 100G and the apparatus 100H. For example, the apparatus 100I can be a copy of the apparatus 100H that also includes dynamic pressure sensors 106*a*, 106*b*, 106*c* (similar to the apparatus 100G) that are coupled to the U-bend 102. Thus, the apparatus 100I can perform all of the functions that can be performed by the apparatus 100G and also by the apparatus 100H.

Although shown in FIG. 1I as including three dynamic pressure sensors 106*a*, 106*b*, 106*c*, the apparatus 100I can include fewer dynamic pressure sensors (such as two dynamic pressure sensors) or more dynamic pressure sensors (such as four dynamic pressure sensors or more than four dynamic pressure sensors). The dynamic pressure sensors 106*a*, 106*b*, 106*c* measure a dynamic pressure of the multiphase fluid 101 flowing through the U-bend 102, as opposed to a static pressure of the multiphase fluid 101. The dynamic pressure sensors 106*a*, 106*b*, 106*c* can be located at any locations along the U-bend 102. In some implementations, the dynamic pressure sensors 106*a*, 106*b*, 106*c* are coupled to the first conduit 102*a* of the U-bend 102. In some implementations, the dynamic pressure sensors 106*a*, 106*b*, 106*c* are coupled to the second conduit 102*b* of the U-bend 102. In some implementations, a first portion of the dynamic pressure sensors 106*a*, 106*b*, 106*c* (for example, one or two of the dynamic pressure sensors 106*a*, 106*b*, 106*c*) is coupled to the first conduit 102*a* of the U-bend 102, and a remaining portion of the dynamic pressure sensors 106*a*, 106*b*, 106*c* is coupled to the second conduit 102*b* of the U-bend 102. The dynamic pressure sensors 106*a*, 106*b*, 106*c* can be evenly or randomly distributed along the U-bend 102.

The dynamic pressure measurements taken by the dynamic pressure sensors 106*a*, 106*b*, 106*c* can be cross-correlated (for example, by the processor 705) to determine a speed of sound of the multiphase fluid 101 flowing through the U-bend 102. The speed of sound of the multiphase fluid 101 and the overall density ($\rho$) of the multiphase fluid 101 can then be used to determine the water-liquid ratio of the multiphase fluid 101. For example, the speed of sound of the multiphase fluid 101 and the overall density ($\rho$) of the multiphase fluid 101 can be compared to a plotted graph of various phase curves (gas/oil, gas/aqueous, oil/aqueous) to determine the water-liquid ratio.

Figure 1J:
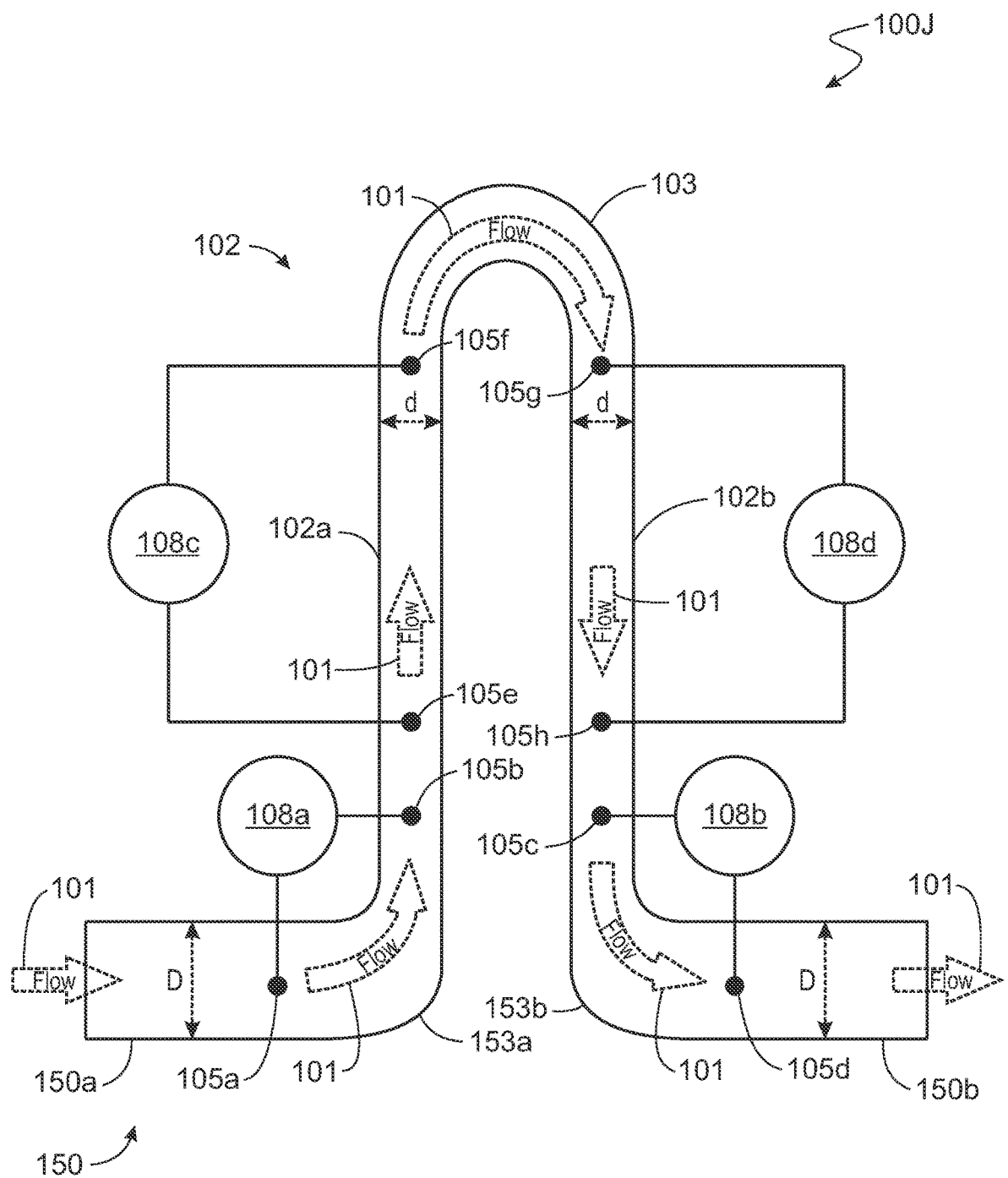
FIG. 1J is a schematic diagram of an example apparatus which can be used to measure a density, a flow rate, and a water-liquid ratio of a multiphase fluid.

FIG. 1J depicts an apparatus 100J which can be used to measure a density, a flow rate, and a water-liquid ratio of a multiphase fluid 101. The apparatus 100J can be substantially similar to the apparatus 100H shown in FIG. 1H. In comparison, the apparatus 100J omits the connecting conduit (102*c* shown in FIG. 1H). The apparatus 100J includes the U-bend 102, which includes the first conduit 102*a* and the second conduit 102*b*. The first conduit 102*a* is connected to the second conduit 102*b* by a curved bend 103. In some implementations, the first conduit 102*a*, the second conduit 102*b*, and the curved bend 103 are integrated, such that the U-bend 102 is a singular, unitary body, as opposed to parts that are disjointed and coupled together to form the U-bend 102. The curved bend 103 can be made of the same material as the first conduit 102*a* and the second conduit 102*b*, such that the friction experienced by the multiphase fluid 101 flowing through each of the components of the U-bend 102 is substantially the same.

As shown in FIG. 1J, the U-bend 102 can be connected to a flow pipe 150 that flows the multiphase fluid 101. The flow pipe 150 includes the first pipe 150*a* and the second pipe 150*b*. In some implementations, the U-bend 102 is connected to the flow pipe 150 by curved bends 153*c*, 153*d*. For example, the first conduit 102*a* of the U-bend 102 is connected to the first pipe 150*a* of the flow pipe 150 by the first curved bend 153*c*. For example, the second conduit 102*b* of the U-bend 102 is connected to the second pipe 150*b* of the flow pipe 150 by the second curved bend 153*d*. In some implementations, the first conduit 102*a*, the second conduit 102*b*, the curved bend 103, the first curved bend 153*c*, the second curved bend 153*d*, and the flow pipe 150 are integrated, such that the U-bend 102 and the flow pipe 150 form a singular, unitary body, as opposed to parts that are disjointed and coupled together.

The apparatus 100J can include a first differential pressure sensor 108*a* coupled to the first pipe 150*a* and to the first conduit 102*a* via pressure ports 105*a* and 105*b*, respectively. The first differential pressure sensor 108*a* is configured to measure a first differential pressure of the multiphase fluid 101 flowing across the first curved bend 153c. The pressure ports 105a and 105b are separated by the specified differential pressure height, h, with respect to gravity. The apparatus 100B can include a second differential pressure sensor 108b coupled to the second conduit 102b and to the second pipe 150b via pressure ports 105c and 105d, respectively. The second differential pressure sensor 108b is configured to measure a second differential pressure of the multiphase fluid 101 flowing across the second curved bend 153d. The pressure ports 105c and 105d are separated by the specified differential pressure height, h, with respect to gravity. As shown in FIG. 1F, the pressure port 105a does not necessarily need to be at the same vertical height as pressure port 105d, and the pressure port 105b does not necessarily need to be at the same vertical height as pressure port 105c. Instead, the vertical distance between pressure port 105a and pressure port 105b should match the vertical distance between pressure port 105c and pressure port 105d. The height difference between the pressure ports 105a, 105b of the first differential pressure sensor 108a and the height difference between the pressure ports 105c, 105d of the second differential pressure sensor 108b are the same, and the horizontal distance between the pressure ports 105a, 105b of the first differential pressure sensor 108a and the horizontal distance between the pressure ports 105c, 105d of the second differential pressure sensor 108b are the same, such that the frictional components of the pressure drops experienced by the multiphase fluid 101 flowing across the first curved bend 153c (measured by the first differential pressure sensor 108a) and through the second curved bend 153d (measured by the second differential pressure sensor 108b) are substantially the same.

The apparatus 100J can include a third differential pressure sensor 108c coupled to the first conduit 102a via pressure ports 105e and 105f. The third differential pressure sensor 108c is configured to measure a third differential pressure of the multiphase fluid 101 flowing through the U-bend 102. The pressure ports 105e and 105f are separated by the specified differential pressure height, h, with respect to gravity. The apparatus 100J can include a fourth differential pressure sensor 108d coupled to the second conduit 102b via pressure ports 105g and 105h. The fourth differential pressure sensor 108d is configured to measure a fourth differential pressure of the multiphase fluid 101 flowing through the U-bend 102. The pressure ports 105g and 105h are separated by the specified differential pressure height, h, with respect to gravity. As shown in FIG. 1J, the pressure port 105e does not necessarily need to be at the same vertical height as pressure port 105h, and the pressure port 105f does not necessarily need to be at the same vertical height as pressure port 105g. Instead, the vertical distance between pressure port 105e and pressure port 105f should match the vertical distance between pressure port 105g and pressure port 105h. The height difference between the pressure ports 105e, 105f of the third differential pressure sensor 108c and the height difference between the pressure ports 105g, 105h of the fourth differential pressure sensor 108d are the same, such that the frictional components of the pressure drops experienced by the multiphase fluid 101 flowing through the first conduit 102a (measured by the third differential pressure sensor 108c) and through the second conduit 102b (measured by the fourth differential pressure sensor 108d) are substantially the same.

Although not shown in FIG. 1J, the first, second, third, and fourth differential pressure sensors 108a, 108b, 108c, 108d can be coupled to a computer (such as the computer 700), to determine characteristics (such as a mixture density, a total mass flow rate, an aqueous phase volume fraction, a gas phase volume fraction, or any combination of these) of the multiphase fluid 101 flowing through the U-bend 102 (for example, using Equations 1, 1a, 1b, 2a, 2b, 2c, 2d, 2e, 2f, 2g, 2h, 3a, 3b, 4a, 4b, 5a, 5b, 5c, 5d, or any combination of these).

Any of the apparatuses 100A, 100B, 100C, 100D, 100E, 100F, 100G, 100H, 100I, or 100J can be combined with any of the following components to obtain additional information about the multiphase fluid 101: a flowmeter (such as a Venturi-type meter), a water-cut meter that measures water fraction or water-liquid ratio, a dynamic pressure sensor, a temperature sensor, or a strain gauge. In cases where a dynamic pressure sensor is included, the dynamic pressure sensor can be located on the same pressure tap as any of the pressure sensors already included in the apparatus (100A, 100B, 100C, 100D, 100E, 100F, 100G, 100H, 100I, or 100J).

Figure 2A:
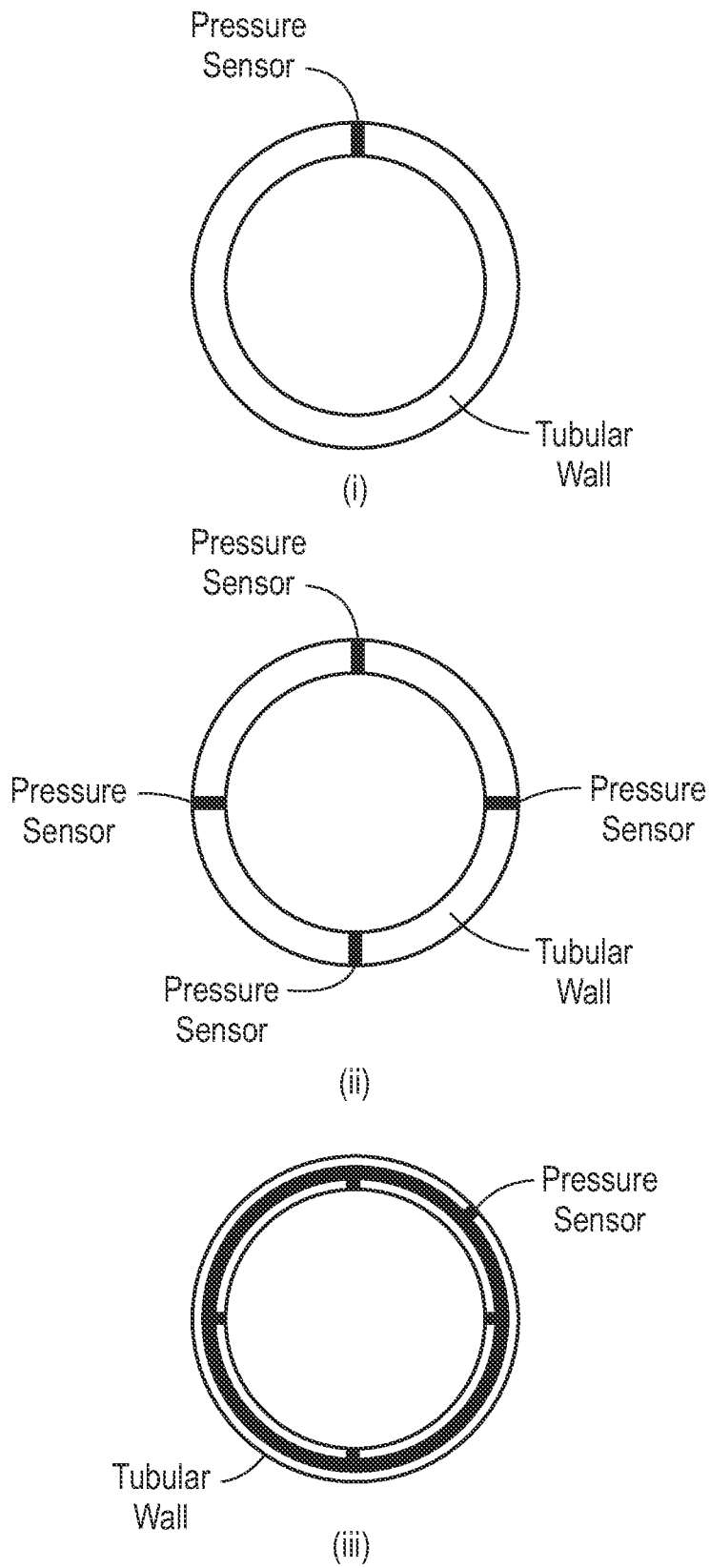
FIG. 2A is a schematic diagram depicting various example pressure tap arrangements.

FIG. 2A is a schematic diagram depicting various example pressure tap arrangements. Each of the views (i), (ii), and (iii) are cross-sectional views of a pipe (for example, the first conduit 102a or the second conduit 102b). Any of the pressure sensors (104a, 104b, 104c, 104d, 104e, 104f, 104a', 104b', 104c', 104d', 104e', 104f) can have the form shown in view (i), (ii), or (iii). In view (i), the pressure sensor includes a single pressure tap. In view (ii), the pressure sensor includes various pressure taps (for example, four) that are distributed around a circumference of the conduit. In view (ii), the pressure sensor can obtain four simultaneous readings (one at each of the four pressure taps) and average the four simultaneous readings to obtain an averaged pressure reading for that particular axial location along the conduit. Although shown in view (ii) as having four pressure taps, the pressure sensors can have fewer pressure taps (such as two or three) or more pressure taps (such as five or more than five). In view (iii), the pressure sensor includes a circumferential pressure tap that fully spans the entire circumference of the conduit. The circumferential pressure tap shown in view (iii) may be the most accurate out of all the views (i), (ii), and (iii) shown in FIG. 2A.

Figure 2B:
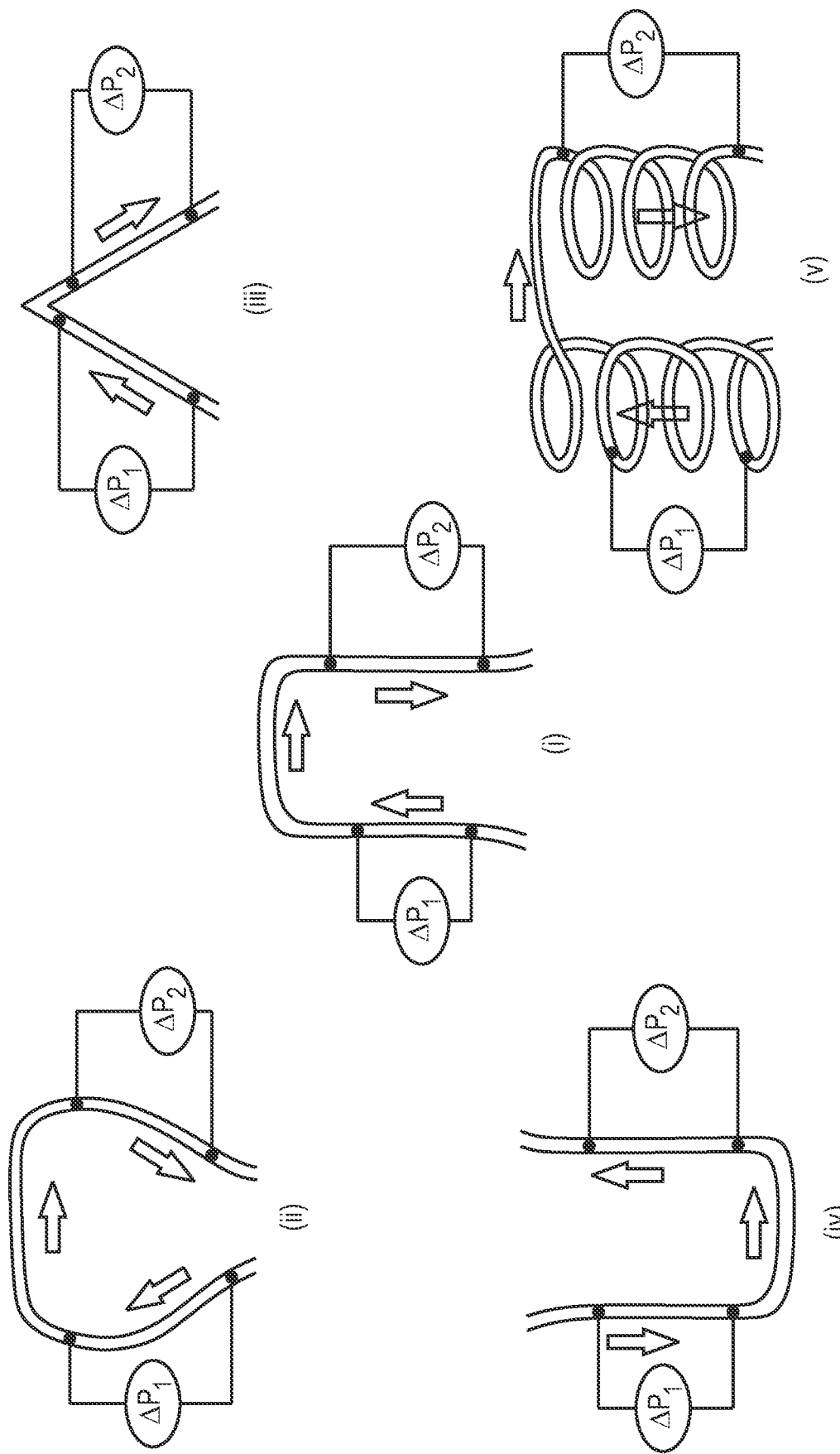
FIG. 2B is a schematic diagram depicting various example piping arrangements.

FIG. 2B is a schematic diagram depicting various example piping arrangements. Each of the views (i), (ii), (iii), (iv), and (v) depict piping arrangements that can used in addition to or alternatively to the piping arrangements already described with respect to the apparatuses 100A, 100B, 100C, 100D, 100E, 100F, 100G, 100H, 100I, and 100J. $\Delta P_1$ is a first differential pressure of the multiphase fluid 101 flowing through the respective piping arrangement. $\Delta P_2$ is a second differential pressure of the multiphase fluid 101 flowing through the respective piping arrangement. $\Delta P_1$ can be measured by a pair of pressure sensors or a single differential pressure sensor. Similarly, $\Delta P_2$ can be measured by a pair of pressure sensors or a single differential pressure sensor. The first and second differential pressures ($\Delta P_1$, $\Delta P_2$) measured from any of these piping arrangements can be used, for example, to determine characteristics (such as a mixture density, a total mass flow rate, an aqueous phase volume fraction, a gas phase volume fraction, or any combination of these) of the multiphase fluid 101 flowing through the respective piping arrangement (for example, using Equations 1, 1a, 1b, 2a, 2b, 2c, 2d, 2e, 2f, 2g, 2h, 3a, 3b, or any combination of these).

As an example, view (i) can be considered a base case that generally conforms to the piping arrangements of apparatuses 100A and 100B shown in FIGS. 1A and 1B, respectively. The piping arrangement of view (ii) is substantially similar to the piping arrangement of view (i), but the first and second conduits 102a, 102b of view (ii) are not necessarily straight pipes. In view (iii), the connecting conduit (102c) is omitted, and the first and second conduits 102a, 102b are connected by an angled bend. The piping arrangement of view (iv) is substantially similar to the piping arrangement of view (i), but is flipped vertically, such that the multiphase fluid 101 flowing through the piping arrangement of view (iv) flows downward before flowing upward. The piping arrangement of view (v) is substantially similar to the piping arrangement of view (i), but the first and second conduits 102a, 102b are coiled (that is, includes coiled piping).

Figure 2C:
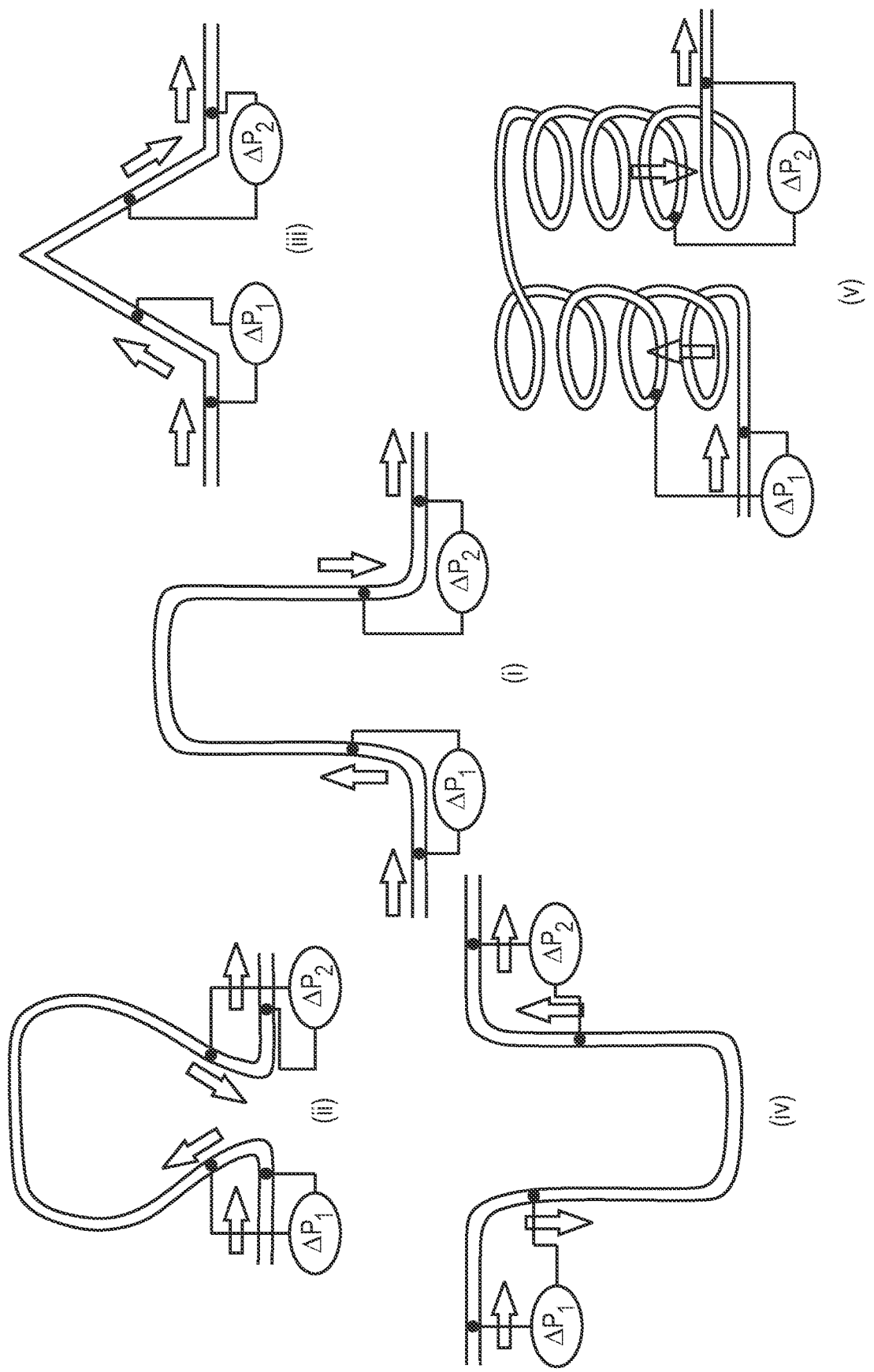
FIG. 2C is a schematic diagram depicting various example piping arrangements.

FIG. 2C is a schematic diagram depicting various example piping arrangements. Each of the views (i), (ii), (iii), (iv), and (v) depict piping arrangements that can used in addition to or alternatively to the piping arrangements already described with respect to the apparatuses 100A, 100B, 100C, 100D, 100E, 100F, 100G, 100H, 100I, and 100J. $\Delta P_1$ is a first differential pressure of the multiphase fluid 101 flowing through the respective piping arrangement across a first bend (curved or angled). $\Delta P_2$ is a second differential pressure of the multiphase fluid 101 flowing through the respective piping arrangement across a second bend (curved or angled). $\Delta P_1$ can be measured by a pair of pressure sensors or a single differential pressure sensor. Similarly, $\Delta P_2$ can be measured by a pair of pressure sensors or a single differential pressure sensor. The first and second differential pressures ($\Delta P_1$, $\Delta P_2$) measured from any of these piping arrangements can be used, for example, to determine characteristics (such as a mixture density, a total mass flow rate, or both) of the multiphase fluid 101 flowing through the respective piping arrangement (for example, using Equations 4a, 4b, 5a, 5b, 5c, 5d, or any combination of these).

As an example, view (i) can be considered a base case that generally conforms to the piping arrangements of apparatuses 100E and 100F shown in FIGS. 1E and 1F, respectively. The piping arrangement of view (ii) is substantially similar to the piping arrangement of view (i), but the first and second conduits 102a, 102b of view (ii) deviate from vertically oriented pipes (that is, they are disposed at non-zero angles with respect to a vertical) and are not necessarily straight pipes. Similarly, in view (iii), the first and second conduits 102a, 102b deviate from vertically oriented pipes, but are straight pipes that are connected with angled bends. The piping arrangement of view (iv) is substantially similar to the piping arrangement of view (i), but is flipped vertically, such that the multiphase fluid 101 flowing through the piping arrangement of view (iv) flows downward before flowing upward. The piping arrangement of view (v) is substantially similar to the piping arrangement of view (i), but the first and second conduits 102a, 102b are coiled (that is, includes coiled piping).

Figure 2D:
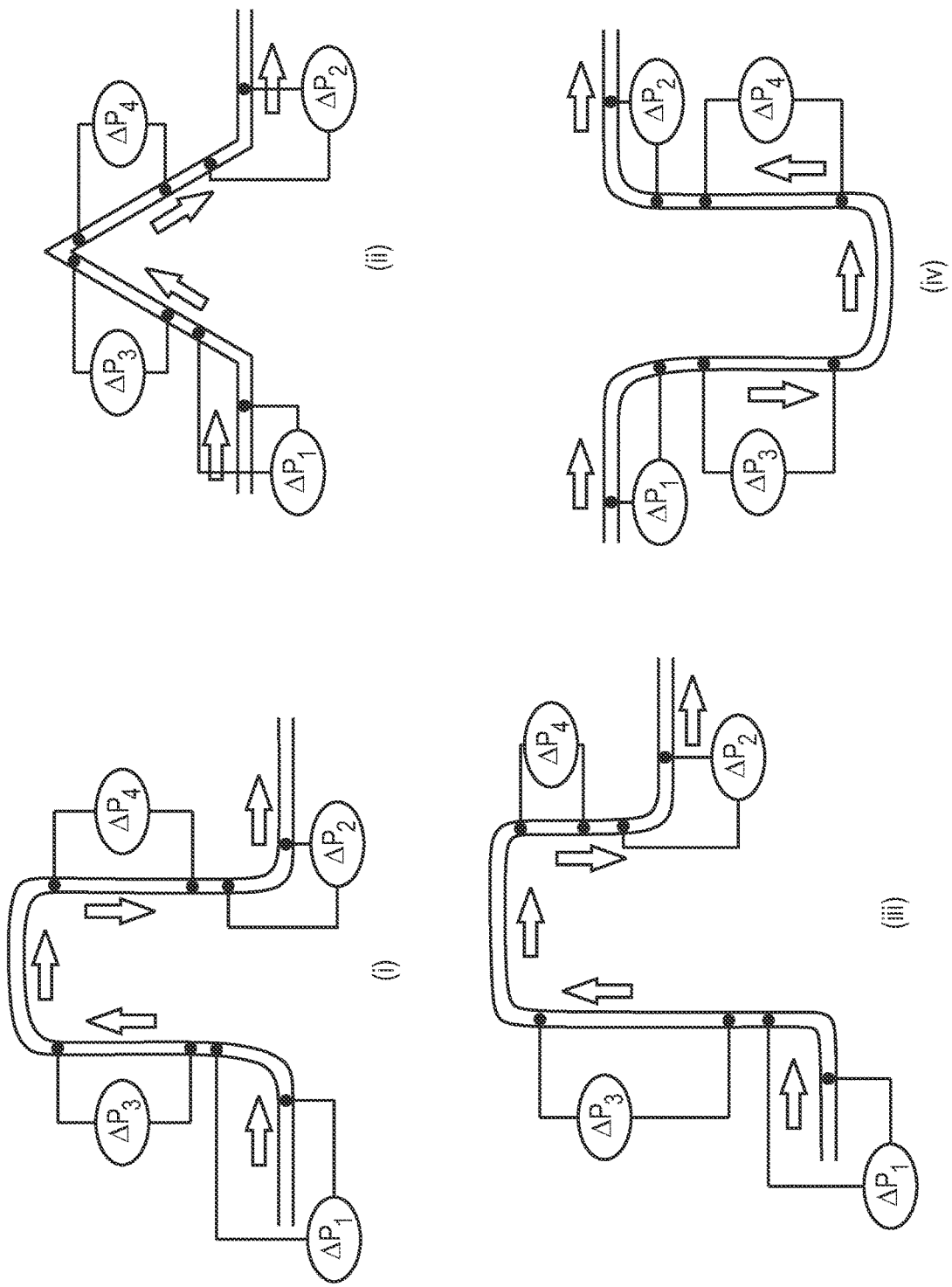
FIG. 2D is a schematic diagram depicting various example piping arrangements.

FIG. 2D is a schematic diagram depicting various example piping arrangements. Each of the views (i), (ii), (iii), and (iv) depict piping arrangements that can used in addition to or alternatively to the piping arrangements already described with respect to the apparatuses 100A, 100B, 100C, 100D, 100E, 100F, 100G, 100H, 100I, and 100J. $\Delta P_1$ is a first differential pressure of the multiphase fluid 101 flowing through the respective piping arrangement across a first bend (curved or angled). $\Delta P_2$ is a second differential pressure of the multiphase fluid 101 flowing through the respective piping arrangement across a second bend (curved or angled). $\Delta P_1$ can be measured by a pair of pressure sensors or a single differential pressure sensor. Similarly, $\Delta P_2$ can be measured by a pair of pressure sensors or a single differential pressure sensor. $\Delta P_3$ is a third differential pressure of the multiphase fluid 101 flowing through the first conduit 102a of the respective piping arrangement. $\Delta P_4$ is a fourth differential pressure of the multiphase fluid 101 flowing through the second conduit 102b of the respective piping arrangement. $\Delta P_3$ can be measured by a pair of pressure sensors or a single differential pressure sensor. Similarly, $\Delta P_4$ can be measured by a pair of pressure sensors or a single differential pressure sensor. The first, second, third, and fourth differential pressures ($\Delta P_1$, $\Delta P_2$, $\Delta P_3$, $\Delta P_4$) measured from any of these piping arrangements can be used, for example, to determine characteristics (such as a mixture density, a total mass flow rate, an aqueous phase volume fraction, a gas phase volume fraction, or any combination of these) of the multiphase fluid 101 flowing through the respective piping arrangement (for example, using Equations 1, 1a, 1b, 2a, 2b, 2c, 2d, 2e, 2f, 2g, 2h, 3a, 3b, 4a, 4b, 5b, 5c, 5d, or any combination of these).

As an example, view (i) can be considered a base case that generally conforms to the piping arrangements of apparatuses 100H and 100J shown in FIGS. 1H and 1J, respectively. The piping arrangement of view (ii) is substantially similar to the piping arrangement of view (i), but the first and second conduits 102a, 102b of view (ii) deviate from vertically oriented pipes and are connected with angled bends. In the piping arrangement of view (iii), the first and second pipes 150a, 150b of the flow pipe 150 are not in-line with one another. The piping arrangement of view (iv) is substantially similar to the piping arrangement of view (i), but is flipped vertically, such that the multiphase fluid 101 flowing through the piping arrangement of view (iv) flows downward before flowing upward.

Figure 2E:
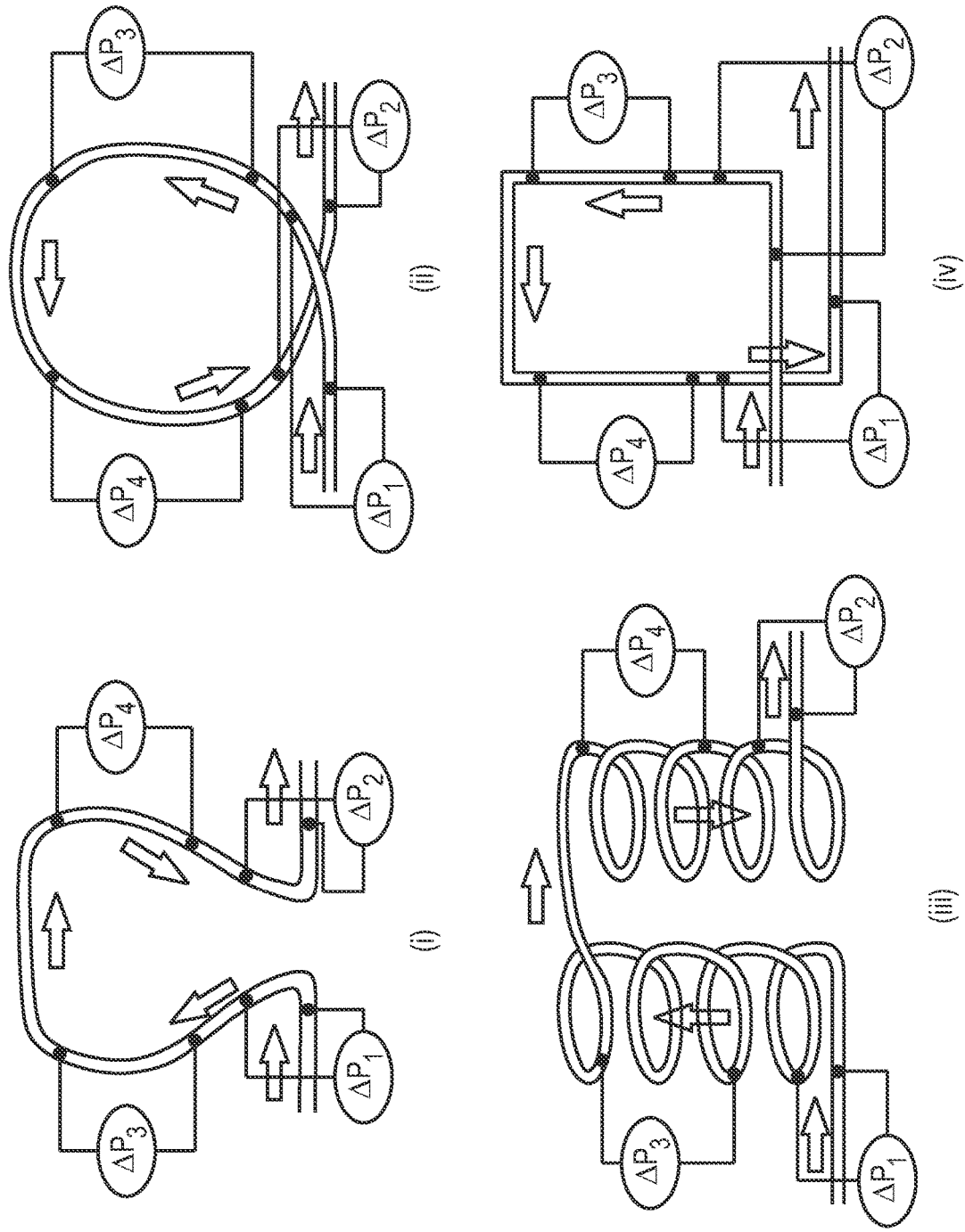
FIG. 2E is a schematic diagram depicting various example piping arrangements.

FIG. 2E is a schematic diagram depicting various example piping arrangements. Each of the views (i), (ii), (iii), and (iv) depict piping arrangements that can used in addition to or alternatively to the piping arrangements already described with respect to the apparatuses 100A, 100B, 100C, 100D, 100E, 100F, 100G, 100H, 100I, and 100J. $\Delta P_1$ is a first differential pressure of the multiphase fluid 101 flowing through the respective piping arrangement across a first bend (curved or angled). $\Delta P_2$ is a second differential pressure of the multiphase fluid 101 flowing through the respective piping arrangement across a second bend (curved or angled). $\Delta P_1$ can be measured by a pair of pressure sensors or a single differential pressure sensor. Similarly, $\Delta P_2$ can be measured by a pair of pressure sensors or a single differential pressure sensor. $\Delta P_3$ is a third differential pressure of the multiphase fluid 101 flowing through the first conduit 102a of the respective piping arrangement. $\Delta P_4$ is a fourth differential pressure of the multiphase fluid 101 flowing through the second conduit 102b of the respective piping arrangement. $\Delta P_3$ can be measured by a pair of pressure sensors or a single differential pressure sensor. Similarly, $\Delta P_4$ can be measured by a pair of pressure sensors or a single differential pressure sensor. The first, second, third, and fourth differential pressures ($\Delta P_1$, $\Delta P_2$, $\Delta P_3$, $\Delta P_4$) measured from any of these piping arrangements can be used, for example, to determine characteristics (such as a mixture density, a total mass flow rate, an aqueous phase volume fraction, a gas phase volume fraction, or any combination of these) of the multiphase fluid 101 flowing through the respective piping arrangement (for example, using Equations 1, 1a, 1b, 2a, 2b, 2c, 2d, 2e, 2f, 2g, 2h, 3a, 3b, 4a, 4b, 5b, 5c, 5d, or any combination of these).

Figure 2F:
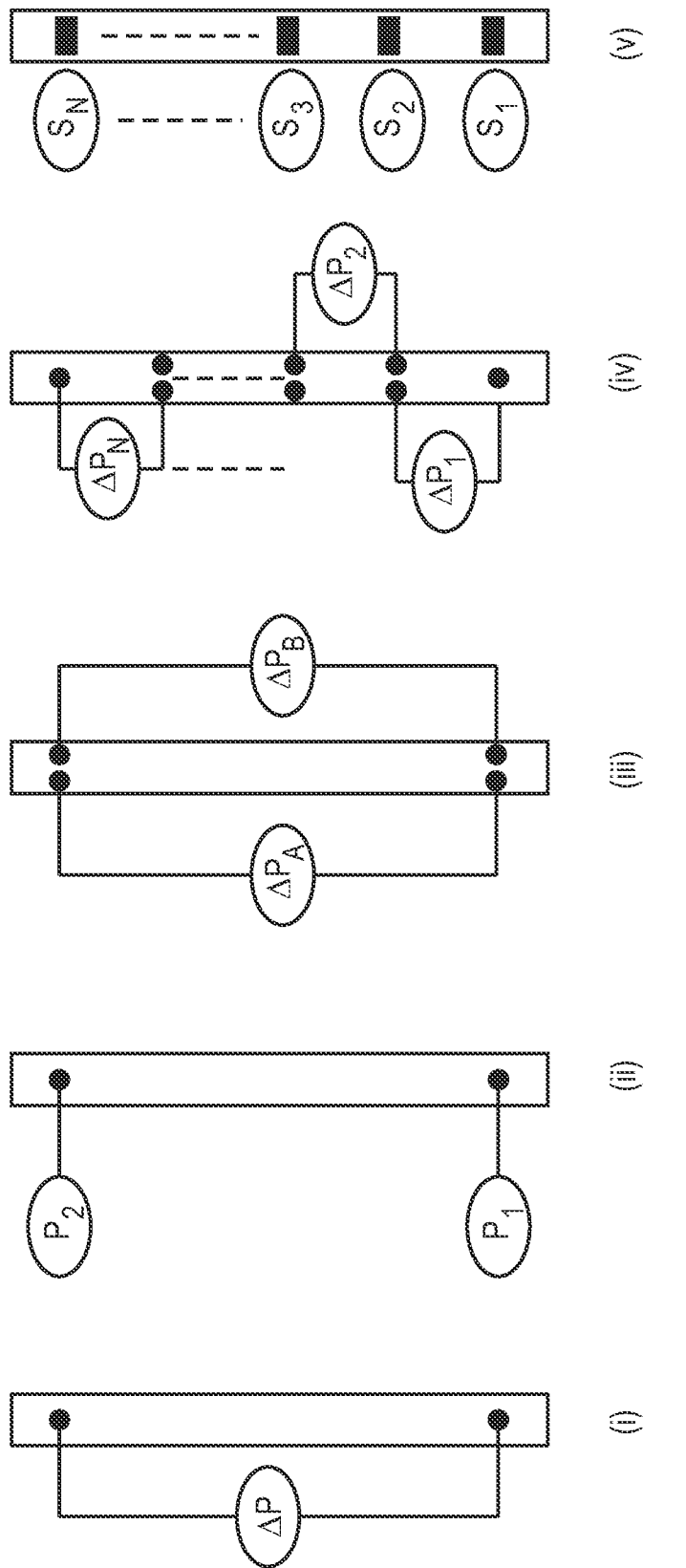
FIG. 2F is a schematic diagram depicting various example sensor arrangements.

The piping arrangement of view (i) is substantially similar to the piping arrangements of apparatuses 100H and 100J shown in FIGS. 1H and 1J, respectively, but the first and second conduits 102a, 102b of view (i) are not necessarily straight pipes. In the piping arrangement of view (ii), the first and second conduits 102a, 102b form a loop. The piping arrangement of view (iii) is substantially similar to the piping arrangement of view (i) of FIG. 2D, but the first and second conduits 102a, 102b are coiled (that is, includes coiled piping). The piping arrangement of view (iv) is substantially similar to the piping arrangement of view (ii), but the first and second conduits 102a, 102b form an angled loop with straight portions of piping in between angled bends. Further, in the piping arrangement of view (iv), the first and second pipes 150a, 150b of the flow pipe 150 are not in-line with one another FIG. 2F is a schematic diagram depicting various example sensor arrangements. Any of the sensor arrangements shown in views (i), (ii), (iii), (iv), and (v) can be applied (either alone or in combination) in addition to or alternatively to the sensor arrangements already described with respect to the apparatuses 100A, 100B, 100C, 100D, 100E, 100F, 100G, 100H, 100I, and 100J.

As an example, view (i) can be considered a base case that generally conforms to the differential pressure sensor arrangements of apparatuses 100B, 100F, and 100J shown in FIGS. 1B, 1F, and 1J, respectively. The pressure sensor arrangement of view (ii) includes two pressure sensors which measure static pressure at their respective locations. A difference between the measured static pressures can be determined as a differential pressure (similar to the differential pressure sensor). The pressure sensor arrangement of view (ii) is substantially similar to the pressure sensor arrangements shown in the apparatuses 100A, 100C, 100D, 100E, 100G, 100H, and 100I shown in FIGS. 1A, 1C, 1D, 1E, 1G, 1H, and 1I, respectively. The differential pressure sensor arrangement of view (iii) is substantially similar to the view (i) but includes redundant differential pressure sensors in a parallel configuration across the same length of piping, which is substantially similar to the differential pressure sensor arrangement shown in apparatus 100C of FIG. 1C. The differential pressure sensor arrangement of view (iv) is substantially similar to the differential pressure sensor arrangement of view (i), but includes additional differential pressure sensors in a series configuration across a length of piping, which is substantially similar to the differential pressure sensor arrangement shown in apparatus 100D of FIG. 1D. The sensor arrangement of view (v) includes multiple strain sensors (such as strain gauges) disposed along a length of piping. The measured strain can be correlated to pressure, such that similar calculations can be completed to determine characteristics of the flowing multiphase fluid 101.

Figure 3A:
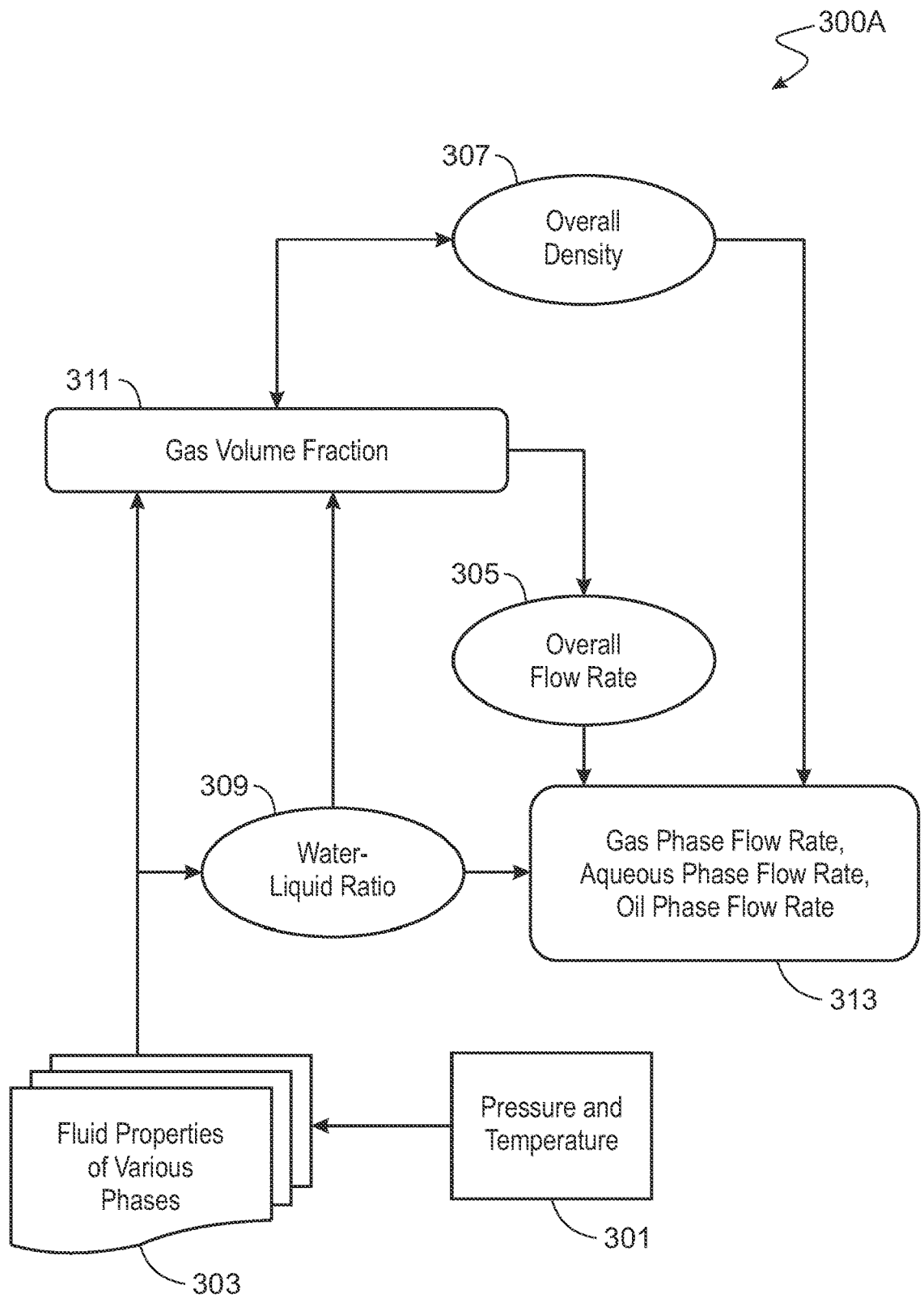
FIG. 3A is a flowchart depicting an example multiphase fluid flow model.

FIG. 3A is a flowchart depicting an example multiphase fluid flow model 300A. Any one of the apparatuses 100H, 100I, or 100J can, for example, be used to implement the model 300A to characterize a multiphase fluid, such as the multiphase fluid 101. At block 301a, pressure and temperature of the multiphase fluid 101 is determined (for example, using pressure and temperature sensors). At block 303a, various properties (such as the density, viscosity, and speed of sound) of the phases (gas phase 101a, aqueous phase 101b', and oil phase 101b") of the multiphase fluid 101 are determined. For example, the gas phase density ($\rho_g$) of the gas phase 101a, the aqueous phase density ($\rho_a$) of the aqueous phase 101b', and the oil phase density ($\rho_o$) of the oil phase 101b" are determined at block 303a. At block 305a, a total flow rate ($m_T$) of the multiphase fluid 101 is determined (for example, using differential pressure sensors as in the apparatus 100D). At block 307a, a mixture density ($\rho$) of the multiphase fluid 101 is determined (for example, using differential pressure sensors as in the apparatus 100A). At block 309a, a water-liquid ratio ($R_{WL}$) of the multiphase fluid 101 is determined (for example, using dynamic pressure sensors as in the apparatus 100E)). At block 311a, a gas volume fraction ($\alpha_g$) is determined at least based on the densities of the various phases (determined at block 303a), the mixture density ($\rho$) of the multiphase fluid 101 (determined at block 307a), and the water-liquid ratio ($R_{WL}$) of the multiphase fluid 101 (determined at block 309a): $\rho=(\rho_a \times R_{WL}+\rho_o \times (1-R_{WL})) \times (1-\alpha_g)+\rho_g \times \alpha_g$. At block 313a, a gas flow rate ($Q_g$) of the gas phase 101a is determined based on the gas volume fraction ($\alpha_g$) and the total volume flow rate (Q) of the multiphase fluid 101: $Q_g=\alpha_g \times Q$. At block 313a, an aqueous phase flow rate ($Q_a$) of the aqueous phase 101b' is determined based on the water-liquid ratio ($R_{WL}$), the gas volume fraction ($\alpha_g$), and the overall flow rate (Q) of the multiphase fluid 101: $Q_a=R_{WL} \times (1-\alpha_g) \times Q$. At block 313a, an oil phase flow rate ($Q_a$) of the oil phase 101b" is determined based on the water-liquid ratio ($R_{WL}$), the gas volume fraction ($\alpha_g$), and the total volume flow rate (Q) of the multiphase fluid 101: $Q_o=(1-R_{WL}) \times (1-\alpha_g) \times Q$.

Figure 3B:
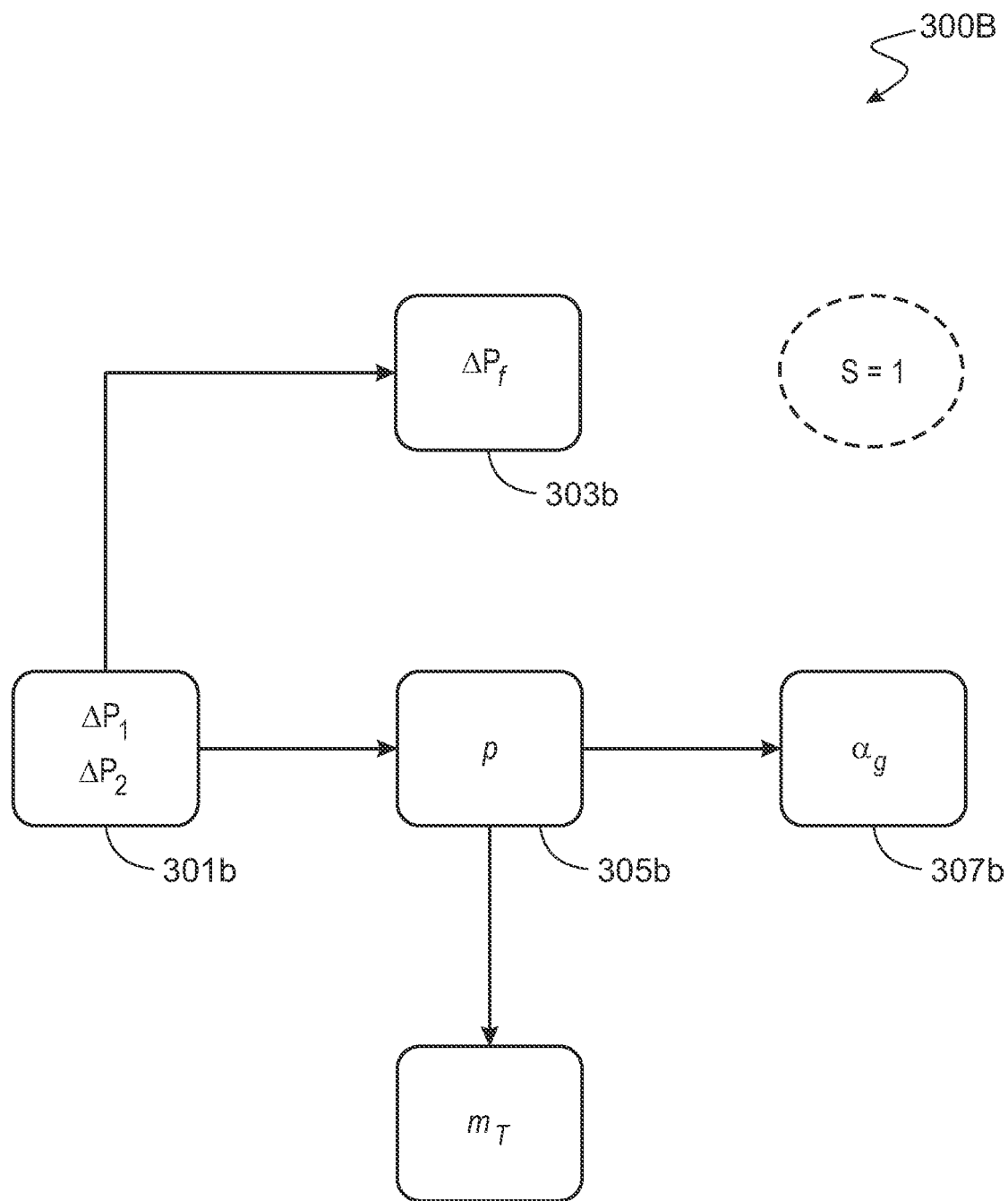
FIG. 3B is a flowchart depicting an example multiphase fluid flow model for determining density.

FIG. 3B is a flowchart depicting an example multiphase fluid flow model 300B. Any one of the apparatuses 100A, 100B, 100C, 100D, 100H, 100I, or 100J can, for example, be used to implement the model 300B to characterize a multiphase fluid, such as the multiphase fluid 101. At block 301b, a first differential pressure ($\Delta P_1$) and a second differential pressure ($\Delta P_2$) of the flowing multiphase fluid 101 is measured. The first differential pressure ($\Delta P_1$) is measured in a first direction across a specified differential pressure height (h). The second differential pressure ($\Delta P_2$) is measured in a second direction (different from the first direction) across the specified differential pressure height (h). The first and second directions are such that the multiphase fluid 101 flows generally upward across the specified differential pressure height (h) in one of the first or second directions and flows generally downward across the specified differential pressure height (h) in the other direction. For example, the multiphase fluid 101 flows generally upward across the specified differential pressure height (h) in the first direction and flows generally downward across the specified differential pressure height (h) in the second direction. For example, the multiphase fluid 101 flows generally downward across the specified differential pressure height (h) in the first direction and flows generally upward across the specified differential pressure height (h) in the second direction.

At block 303b, a frictional pressure loss ($\Delta P_f$) of the flowing multiphase fluid 101 is calculated based on the first and second differential pressures ($\Delta P_1$, $\Delta P_2$) measured at block 301b. The frictional pressure loss ($\Delta P_f$) can be calculated at block 303b, for example, by Equation 2h. At block 305b, a mixture density ($\rho$) of the multiphase fluid 101 is calculated based on the first and second differential pressures ($\Delta P_1$, $\Delta P_2$) measured at block 301b. The mixture density ($\rho$) can be calculated at block 305b, for example, by Equation 2d. At block 307b, a gas phase volume fraction ($\alpha_g$) of the multiphase fluid 101 is calculated based on the mixture density ($\rho$) determined at block 305b. The gas phase volume fraction ($\alpha_g$) can be calculated at block 307b, for example, by Equation 3b. In some implementations, gas phase volume fraction ($\alpha_g$) can be calculated at block 307b based on other known or measured parameters, such as density of the liquid phase ($\rho_l$) and density of the gas phase ($\rho_g$). In such implementations, the gas phase volume fraction ($\alpha_g$) can be calculated by Equation 6a.

$$\alpha_g = \frac{\rho - \rho_l}{\rho_g - \rho_l} \quad (6a)$$

In some implementations, a total mass flow rate ($m_T$) of the multiphase fluid 101 is determined. The total mass flow rate ($m_T$) can be determined, for example, by a mass flowmeter and/or by any of Equations 3a, 4a, or 4b. The multiphase fluid flow model 300B assumes that a slip ratio (S) of the multiphase fluid 101 is substantially equal to 1. The slip ratio (S) is the ratio of the velocity of the gas phase to the velocity of the liquid phase (including the aqueous phase and the oil phase) in the flowing multiphase fluid 101.

Figure 3C:
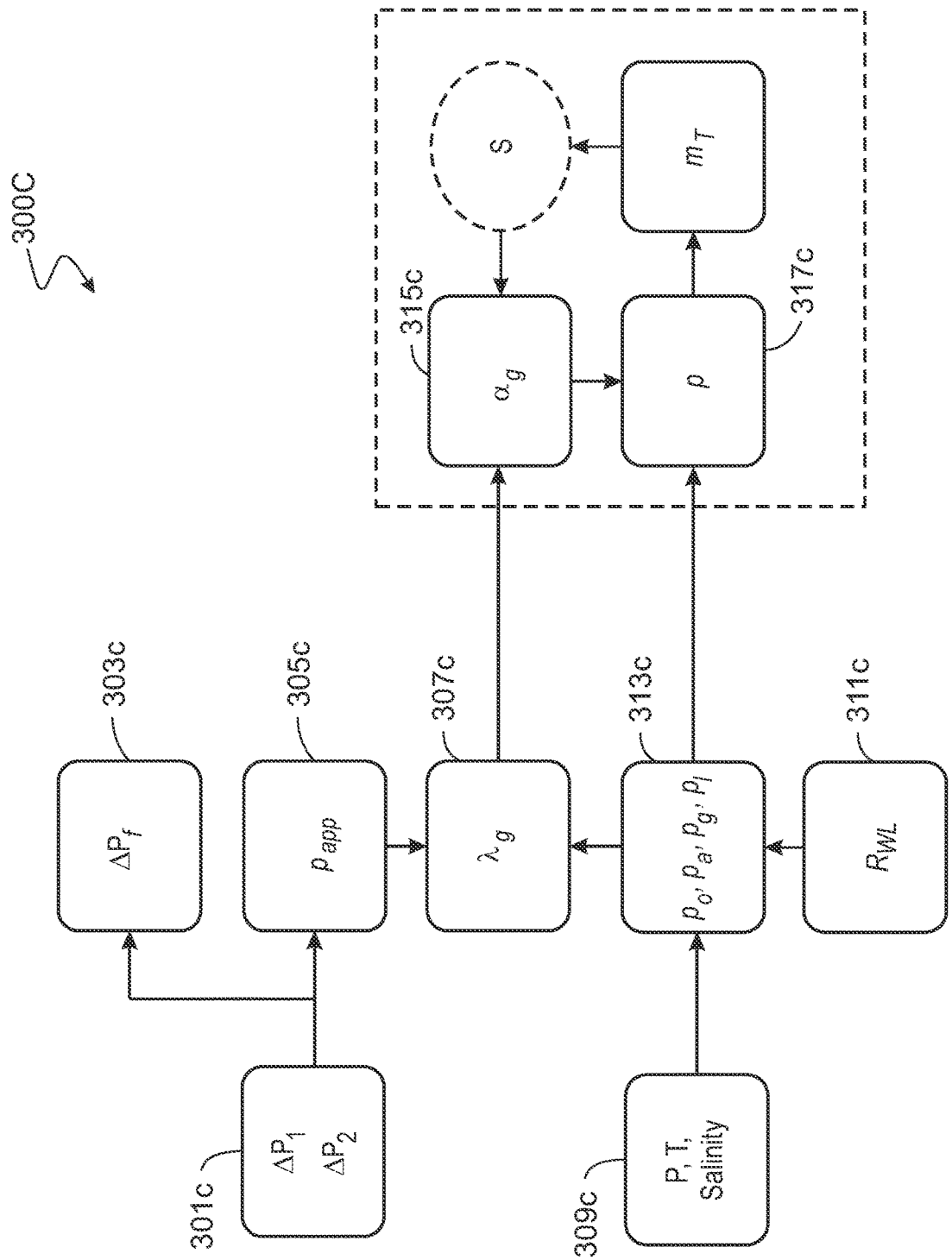
FIG. 3C is a flowchart depicting an example multiphase fluid flow model for determining density.

FIG. 3C is a flowchart depicting an example multiphase fluid flow model 300C. Any one of the apparatuses 100A, 100B, 100C, 100D, 100H, 100I, or 100J can, for example, be used to implement the model 300C to characterize a multiphase fluid, such as the multiphase fluid 101. At block 301c, a first differential pressure ($\Delta P_1$) and a second differential pressure ($\Delta P_2$) of the flowing multiphase fluid 101 is measured. The first differential pressure ($\Delta P_1$) is measured in a first direction across a specified differential pressure height (h). The second differential pressure ($\Delta P_2$) is measured in a second direction (different from the first direction) across the specified differential pressure height (h). The first and second directions are such that the multiphase fluid 101 flows generally upward across the specified differential pressure height (h) in one of the first or second directions and flows generally downward across the specified differential pressure height (h) in the other direction. For example, the multiphase fluid 101 flows generally upward across the specified differential pressure height (h) in the first direction and flows generally downward across the specified differential pressure height (h) in the second direction. For example, the multiphase fluid 101 flows generally downward across the specified differential pressure height (h) in the first direction and flows generally upward across the specified differential pressure height (h) in the second direction.

At block 303c, a frictional pressure loss ($\Delta P_f$) of the flowing multiphase fluid 101 is calculated based on the first and second differential pressures ($\Delta P_1$, $\Delta P_2$) measured at block 301c. The frictional pressure loss ($\Delta P_f$) can be calculated at block 303c, for example, by Equation 2h. At block 305c, an apparent mixture density ($\rho_{app}$) of the multiphase fluid 101 is estimated based on the first and second differential pressures ($\Delta P_1$, $\Delta P_2$) measured at block 301c. The apparent mixture density ($\rho_{app}$) can be estimated at block 305c, for example, by Equation 2d. At block 307c, a void fraction ($\lambda_g$) of the multiphase fluid 101 is calculated based on the apparent mixture density ($\rho_{app}$) estimated at block 305c. The void fraction ($\lambda_g$) can be calculated at block 307c, for example, by Equation 6b.

$$\lambda_g = \frac{\rho_{app} - \rho_l}{\rho_g - \rho_l} \quad (6b)$$

At block 309c, various operating conditions and/or properties (such as pressure, temperature, and salinity) about the flowing multiphase fluid 101 are determined. The conditions and/or properties determined at block 309c can be measured, for example, by external sensors (such as pressure sensors, temperature sensors, and brine samplers). At block 311c, a water-liquid ratio ($R_{WL}$) of the flowing multiphase fluid 101 is determined. The water-liquid ratio ($R_{WL}$) can be determined at block 311c can be measured, for example, by external sensors (such as dynamic pressure sensors, as in apparatus 100G shown in FIG. 1G). At block 313c, densities of the various phases (such as density of the gas phase ($\rho_g$), density of the aqueous phase ($\rho_a$), and density of the oil phase ($\rho_o$)) of the flowing multiphase fluid 101 are determined. The densities of the various phases of the flowing multiphase fluid 101 can be determined at block 313c, for example, based on the operating conditions (pressure and temperature) of the flowing multiphase fluid 101 determined at block 309c. At block 313c, a density of the liquid phase ($\rho_l$, including the aqueous phase and the oil phase) is determined. The density of the liquid phase ($\rho_l$) can be determined at block 313c based on the densities of the various phases of the flowing multiphase fluid 101 and the water-liquid ratio ($R_{WL}$) determined at block 311c. The density of the liquid phase ($\rho_l$) can be determined at block 313c by Equation 6c.

$$\rho_l = \rho_a R_{WL} + \rho_o(1 - R_{WL}) \quad (6c)$$

In some implementations, the void fraction ($\lambda_g$) can be calculated at block 307c based on the density of the liquid phase ($\rho_l$) and the density of the gas phase ($\rho_g$) determined at block 313c.

At block 315c, a gas phase volume fraction ($\alpha_g$) of the multiphase fluid 101 is calculated based on the void fraction ($\lambda_g$) determined at block 307c and slip ratio (S) of the flowing multiphase fluid 101. The slip ratio (S) used at block 315c to determine the gas phase volume fraction ($\alpha_g$) can, for example, be measured by an external sensor or assumed to be substantially equal to 1 as an initial guess. At block 317c, a mixture density ($\rho$) of the multiphase fluid 101 is calculated based on the gas phase volume fraction ($\alpha_g$) determined at block 315c, the density of the gas phase ($\rho_g$) determined at block 313c, and the density of the liquid phase ($\rho_l$) determined at block 313c. The mixture density ($\rho$) can be determined at block 317c by Equation 6d.

$$\rho = \alpha_g \rho_g + (1 - \alpha_g)\rho_l \quad (6d)$$

In some implementations, a total mass flow rate ($m_T$) of the multiphase fluid 101 is determined. The total mass flow rate ($m_T$) can be determined, for example, by a mass flowmeter and/or by any of Equations 3a, 4a, or 4b. In some implementations, the blocks in the dotted box of the multiphase fluid flow model 300C (blocks 315c, 317c, determining the total mass flow rate ($m_T$), and determining the slip ratio (S)) are performed simultaneously (for example, in parallel). In some implementations, the blocks in the dotted box of the multiphase fluid flow model 300C (blocks 315c, 317c, determining the total mass flow rate ($m_T$), and determining the slip ratio (S)) are performed iteratively (for example, in series) until the calculated values converge to final values.

Figure 3D:
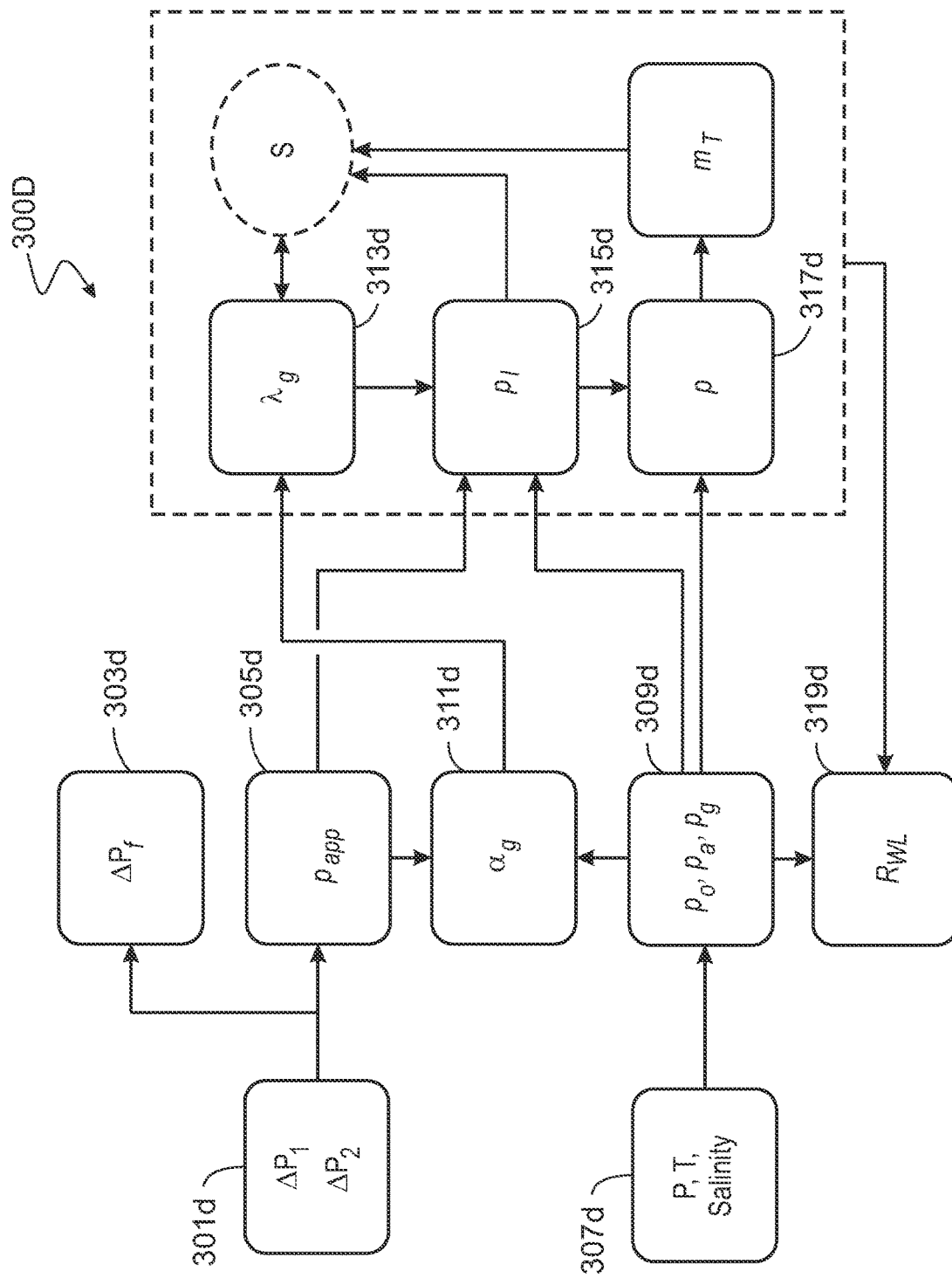
FIG. 3D is a flowchart depicting an example multiphase fluid flow model for determining density.

FIG. 3D is a flowchart depicting an example multiphase fluid flow model 300D. Any one of the apparatuses 100A, 100B, 100C, 100D, 100H, 100I, or 100J can, for example, be used to implement the model 300D to characterize a multiphase fluid, such as the multiphase fluid 101. At block 301d, a first differential pressure ($\Delta P_1$) and a second differential pressure ($\Delta P_2$) of the flowing multiphase fluid 101 is measured. The first differential pressure ($\Delta P_1$) is measured in a first direction across a specified differential pressure height (h). The second differential pressure ($\Delta P_2$) is measured in a second direction (different from the first direction) across the specified differential pressure height (h). The first and second directions are such that the multiphase fluid 101 flows generally upward across the specified differential pressure height (h) in one of the first or second directions and flows generally downward across the specified differential pressure height (h) in the other direction. For example, the multiphase fluid 101 flows generally upward across the specified differential pressure height (h) in the first direction and flows generally downward across the specified differential pressure height (h) in the second direction. For example, the multiphase fluid 101 flows generally downward across the specified differential pressure height (h) in the first direction and flows generally upward across the specified differential pressure height (h) in the second direction.

At block 303d, a frictional pressure loss ($\Delta P_f$) of the flowing multiphase fluid 101 is calculated based on the first and second differential pressures ($\Delta P_1$, $\Delta P_2$) measured at block 301d. The frictional pressure loss ($\Delta P_f$) can be calculated at block 303d, for example, by Equation 2h. At block 305d, an apparent mixture density ($\rho_{app}$) of the multiphase fluid 101 is estimated based on the first and second differential pressures ($\Delta P_1$, $\Delta P_2$) measured at block 301d. The apparent mixture density ($\rho_{app}$) can be estimated at block 305d, for example, by Equation 2d.

At block 307d, various operating conditions and/or properties (such as pressure, temperature, and salinity) about the flowing multiphase fluid 101 are determined. The conditions and/or properties determined at block 307d can be measured, for example, by external sensors (such as pressure sensors, temperature sensors, and brine samplers). At block 309d, densities of the various phases (such as density of the gas phase (p 9), density of the aqueous phase ($\rho_a$), and density of the oil phase ($\rho_o$)) of the flowing multiphase fluid 101 are determined. The densities of the various phases of the flowing multiphase fluid 101 can be determined at block 309d, for example, based on the operating conditions (pressure and temperature) of the flowing multiphase fluid 101 determined at block 307d. At block 311d, a gas phase volume fraction ($\alpha_g$) of the flowing multiphase fluid 101 is determined. The gas phase volume fraction ($\alpha_g$) determined at block 311d can be measured, for example, by an external sensor (such as an ultrasonic sensor).

At block 313d, a void fraction ($\lambda_g$) of the multiphase fluid 101 is calculated based on the gas volume fraction ($\alpha_g$) determined at block 311d and slip ratio (S) of the flowing multiphase fluid 101. The slip ratio (S) used at block 313d to determine the void fraction ($\lambda_g$) can, for example, be measured by an external sensor or assumed to be substantially equal to 1 as an initial guess. At block 315d, a density of the liquid phase ($\rho_l$, including the aqueous phase and the oil phase) is determined. The density of the liquid phase ($\rho_l$) can be determined at block 315d based on the apparent mixture density ($\rho_{app}$) determined at block 305d, the densities of the various phases of the flowing multiphase fluid 101 determined at block 309d, and the void fraction ($\lambda_g$) determined at block 313d. The density of the liquid phase ($\rho_l$) can be calculated at block 315d, for example, by Equation 6e.

$$\rho_l = \frac{\rho_{app} - \lambda_g \rho_g}{1 - \lambda_g} \quad (6e)$$

At block 317d, a mixture density ($\rho$) of the multiphase fluid 101 is calculated based on the density of the gas phase ($\rho_g$) determined at block 309d, the gas phase volume fraction ($\alpha_g$) determined at block 311d, and the density of the liquid phase ($\rho_l$) determined at block 315d. The mixture density ($\rho$) can be determined at block 317c by Equation 6d.

In some implementations, a total mass flow rate ($m_T$) of the multiphase fluid 101 is determined. The total mass flow rate ($m_T$) can be determined, for example, by a mass flowmeter and/or by any of Equations 3a, 4a, or 4b. In some implementations, the blocks in the dotted box of the multiphase fluid flow model 300D (blocks 313d, 315d, 317d, determining the total mass flow rate ($m_T$), and determining the slip ratio (S)) are performed simultaneously (for example, in parallel). In some implementations, the blocks in the dotted box of the multiphase fluid flow model 300D (blocks 313d, 315d, 317d, determining the total mass flow rate ($m_T$), and determining the slip ratio (S)) are performed iteratively (for example, in series) until the calculated values converge to final values. At block 319d, a water-liquid ratio ($R_{WL}$) of the multiphase fluid 101 is determined. The water-liquid ratio ($R_{WL}$) can be determined at block 319d by re-arranging Equation 6c to solve for $$R_{WL}\left(R_{WL} = \frac{\rho_l - \rho_o}{\rho_a - \rho_o}\right).$$

Figure 3E:
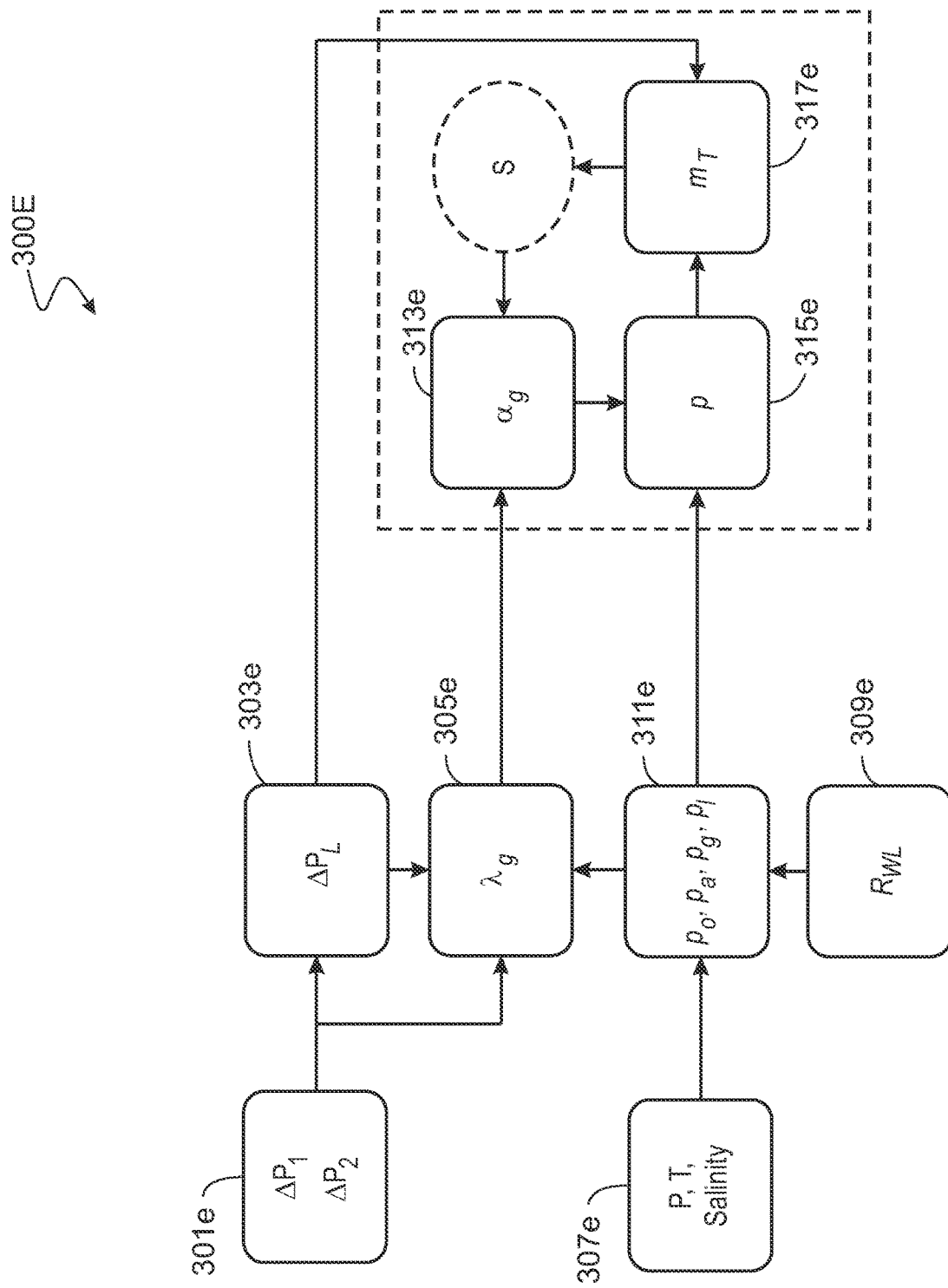
FIG. 3E is a flowchart depicting an example multiphase fluid flow model for determining flow rate.

FIG. 3E is a flowchart depicting an example multiphase fluid flow model 300E. Any one of the apparatuses 100E, 100F, 100H, 100I, or 100J can, for example, be used to implement the model 300E to characterize a multiphase fluid, such as the multiphase fluid 101. At block 301e, a first differential pressure ($\Delta P_1$) and a second differential pressure ($\Delta P_2$) of the flowing multiphase fluid 101 is measured. The first differential pressure ($\Delta P_1$) is measured across a first bend in piping. The second differential pressure ($\Delta P_2$) is measured across a second bend in piping. The multiphase fluid 101 flows generally upward across either of the first or second bends and flows generally downward across the other of the first or second bends. For example, the multiphase fluid 101 flows generally upward across the first bend and flows generally downward across the second bend. For example, the multiphase fluid 101 flows generally downward across the first bend and flows generally upward across the second bend. Examples are provided with respect to apparatuses 100E, 100F, 100H, 100I, and 100J shown in FIGS. 1E, 1F, 1H, 1I, and 1J, respectively). At block 303e, either one of the first differential pressure ($\Delta P_1$) or the second differential pressure ($\Delta P_2$) measured at block 301e is selected for further calculations in the model 300E.

At block 305e, a void fraction ($\lambda_g$) of the multiphase fluid 101 is determined. The void fraction ($\lambda_g$) determined at block 305e can be measured for example, by an external sensor (such as an ultrasonic sensor). At block 307e, various operating conditions and/or properties (such as pressure, temperature, and salinity) about the flowing multiphase fluid 101 are determined. The conditions and/or properties determined at block 307e can be measured, for example, by external sensors (such as pressure sensors, temperature sensors, and brine samplers). At block 309e, a water-liquid ratio ($R_{WL}$) of the flowing multiphase fluid 101 is determined. The water-liquid ratio ($R_{WL}$) can be determined at block 309e can be measured, for example, by external sensors (such as dynamic pressure sensors, as in apparatus 100G shown in FIG. 1G). At block 311e, densities of the various phases (such as density of the gas phase ($\rho_g$), density of the aqueous phase ($\rho_a$), and density of the oil phase ($\rho_o$)) of the flowing multiphase fluid 101 are determined. The densities of the various phases of the flowing multiphase fluid 101 can be determined at block 311e, for example, based on the operating conditions (pressure and temperature) of the flowing multiphase fluid 101 determined at block 307e. At block 311e, a density of the liquid phase ($\rho_l$, including the aqueous phase and the oil phase) is determined. The density of the liquid phase ($\rho_l$) can be determined at block 311e based on the densities of the various phases of the flowing multiphase fluid 101 and the water-liquid ratio ($R_{WL}$) determined at block 309e. The density of the liquid phase ($\rho_l$) can be determined at block 311e by Equation 6c. In some implementations, the void fraction ($\lambda_g$) can be calculated at block 305e based on the density of the liquid phase ($\rho_l$) and the density of the gas phase ($\rho_g$) determined at block 311e.

At block 313e, a gas phase volume fraction ($\alpha_g$) of the multiphase fluid 101 is calculated based on the void fraction ($\lambda_g$) determined at block 305e and slip ratio (S) of the flowing multiphase fluid 101. The slip ratio (S) used at block 313e to determine the gas phase volume fraction ($\alpha_g$) can, for example, be measured by an external sensor or assumed to be substantially equal to 1 as an initial guess. At block 315e, a mixture density ($\rho$) of the multiphase fluid 101 is calculated based on the gas phase volume fraction ($\alpha_g$) determined at block 313e, the density of the gas phase ($\rho_g$) determined at block 311e, and the density of the liquid phase ($\rho_l$) determined at block 311e. The mixture density ($\rho$) can be determined at block 315e by Equation 6d. At block 317e, a total mass flow rate ($m_T$) of the multiphase fluid 101 is determined. The total mass flow rate ($m_T$) can be determined at block 317e, for example, by a mass flowmeter and/or by any of Equations 4a or 4b based on the selected differential pressure at block 303e. In some implementations, the blocks in the dotted box of the multiphase fluid flow model 300E (blocks 313e, 315e, 317e, and determining the slip ratio (S)) are performed simultaneously (for example, in parallel). In some implementations, the blocks in the dotted box of the multiphase fluid flow model 300E (blocks 313e, 315e, 317e, and determining the slip ratio (S)) are performed iteratively (for example, in series) until the calculated values converge to final values.

Figure 3F:
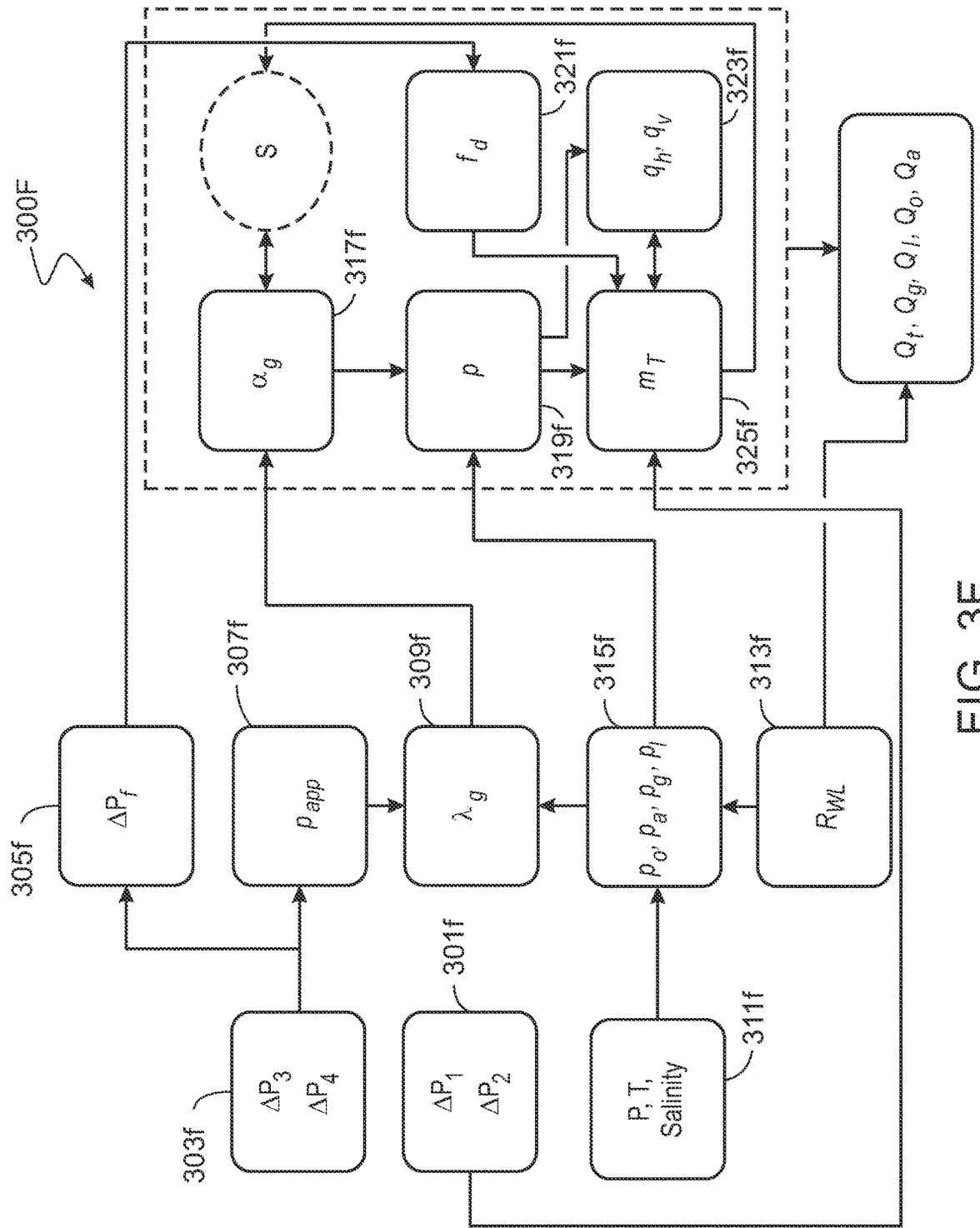
FIG. 3F is a flowchart depicting an example multiphase fluid flow model.

FIG. 3F is a flowchart depicting an example multiphase fluid flow model 300F. Any one of the apparatuses 100H, 100I, or 100J can, for example, be used to implement the model 300F to characterize a multiphase fluid, such as the multiphase fluid 101. At block 301f, a first differential pressure ($\Delta P_1$) and a second differential pressure ($\Delta P_2$) of the flowing multiphase fluid 101 is measured. The first differential pressure ($\Delta P_1$) is measured across a first bend in piping. The second differential pressure ($\Delta P_2$) is measured across a second bend in piping. The multiphase fluid 101 flows generally upward across either of the first or second bends and flows generally downward across the other of the first or second bends. For example, the multiphase fluid 101 flows generally upward across the first bend and flows generally downward across the second bend. For example, the multiphase fluid 101 flows generally downward across the first bend and flows generally upward across the second bend. Examples are provided with respect to apparatuses 100E, 100F, 100H, 100I, and 100J shown in FIGS. 1E, 1F, 1H, 1I, and 1J, respectively).

At block 303f, a third differential pressure ($\Delta P_3$) and a fourth differential pressure ($\Delta P_4$) of the flowing multiphase fluid 101 is measured. The third differential pressure ($\Delta P_1$) is measured in a first direction across a specified differential pressure height (h). The second differential pressure ($\Delta P_2$) is measured in a second direction (different from the first direction) across the specified differential pressure height (h). The first and second directions are such that the multiphase fluid 101 flows generally upward across the specified differential pressure height (h) in one of the first or second directions and flows generally downward across the specified differential pressure height (h) in the other direction. For example, the multiphase fluid 101 flows generally upward across the specified differential pressure height (h) in the first direction and flows generally downward across the specified differential pressure height (h) in the second direction. For example, the multiphase fluid 101 flows generally downward across the specified differential pressure height (h) in the first direction and flows generally upward across the specified differential pressure height (h) in the second direction.

At block 305f, a frictional pressure loss ($\Delta P_f$) of the flowing multiphase fluid 101 is calculated based on the third and fourth differential pressures ($\Delta P_3$, $\Delta P_4$) measured at block 303f. The frictional pressure loss ($\Delta P_f$) can be calculated at block 305f, for example, by Equation 2h. At block 307f, an apparent mixture density ($\rho_{app}$) of the multiphase fluid 101 is estimated based on the third and fourth differential pressures ($\Delta P_3$, $\Delta P_4$) measured at block 303f. The apparent mixture density ($\rho_{app}$) can be estimated at block 307f, for example, by Equation 2d. At block 309f, a void fraction ($\lambda_g$) of the multiphase fluid 101 is calculated based on the apparent mixture density ($\rho_{app}$) estimated at block 307f. The void fraction ($\lambda_g$) can be calculated at block 309f, for example, by Equation 6b.

At block 311f, various operating conditions and/or properties (such as pressure, temperature, and salinity) about the flowing multiphase fluid 101 are determined. The conditions and/or properties determined at block 311f can be measured, for example, by external sensors (such as pressure sensors, temperature sensors, and brine samplers). At block 313f, a water-liquid ratio ($R_{WL}$) of the flowing multiphase fluid 101 is determined. The water-liquid ratio ($R_{WL}$) can be determined at block 313f can be measured, for example, by external sensors (such as dynamic pressure sensors, as in apparatus 100G shown in FIG. 1G). At block 315f, densities of the various phases (such as density of the gas phase ($\rho_g$), density of the aqueous phase ($\rho_a$), and density of the oil phase ($\rho_o$)) of the flowing multiphase fluid 101 are determined. The densities of the various phases of the flowing multiphase fluid 101 can be determined at block 315f, for example, based on the operating conditions (pressure and temperature) of the flowing multiphase fluid 101 determined at block 311f. At block 315f, a density of the liquid phase ($\rho_l$, including the aqueous phase and the oil phase) is determined. The density of the liquid phase ($\rho_l$) can be determined at block 315f based on the densities of the various phases of the flowing multiphase fluid 101 and the water-liquid ratio ($R_{WL}$) determined at block 313f. The density of the liquid phase ($\rho_l$) can be determined at block 315f by Equation 6c. In some implementations, the void fraction ($\lambda_g$) can be calculated at block 309f based on the density of the liquid phase ($\rho_l$) and the density of the gas phase ($\rho_g$) determined at block 315f.

At block 317f, a gas phase volume fraction ($\alpha_g$) of the multiphase fluid 101 is calculated based on the void fraction ($\lambda_g$) determined at block 309f and slip ratio (S) of the flowing multiphase fluid 101. The slip ratio (S) used at block 317f to determine the gas phase volume fraction ($\alpha_g$) can, for example, be measured by an external sensor or assumed to be substantially equal to 1 as an initial guess. At block 319f, a mixture density ($\rho$) of the multiphase fluid 101 is calculated based on the gas phase volume fraction ($\alpha_g$) determined at block 317f, the density of the gas phase ($\rho_g$)

determined at block 315f, and the density of the liquid phase ($\rho_l$) determined at block 315f. The mixture density ($\rho$) can be determined at block 319f by Equation 6d.

At block 321f, a friction factor ($f_d$) of the flowing multiphase fluid 101 is determined based on the frictional pressure loss ($\Delta P_f$) determined at block 305f. At block 323f, a horizontal flow dynamic pressure ($q_h$) and a vertical flow dynamic pressure ($q_v$) are determined. The horizontal flow dynamic pressure ($q_h$) and the vertical flow dynamic pressure ($q_v$) determined at block 323f can be, for example, measured by external sensors (such as dynamic pressure sensors). In some implementations, the horizontal flow dynamic pressure ($q_h$) is determined by Equation 6f$_h$. In some implementations, the vertical flow dynamic pressure ($q_v$) is determined by Equation 6f$_v$. In some implementations, the friction factor ($f_d$) is determined at block 321f by Equation 6g, which depends on the horizontal flow dynamic pressure ($q_h$) and the vertical flow dynamic pressure ($q_v$) determined at block 323f (for example, by sensors or by Equations 6f$_h$ and 6f$_v$.

$$q_h = \frac{\rho\left(\frac{m_T}{\rho A_h}\right)^2}{2} \quad (6f_h)$$

$$q_v = \frac{\rho\left(\frac{m_T}{\rho A_v}\right)^2}{2} \quad (6f_v)$$

$$f_d = \frac{\Delta P_f}{q_v\left(\frac{h}{D_v}\right)} \quad (6g)$$

In Equation 6f$_h$, $A_h$ is a cross-sectional flow area for the horizontal flow of the multiphase fluid 101. In Equation 6f$_v$, $A_v$ is a cross-sectional flow area for the vertical flow of the multiphase fluid 101. In Equation 6g, h is the specified differential pressure height, and $D_v$ is the inner diameter of the conduit in which the direction of flow of the multiphase fluid 101 is generally upward or generally downward.

At block 325f, a total mass flow rate ($m_T$) of the multiphase fluid 101 is determined. The total mass flow rate ($m_T$) can be determined at block 325f, for example, by a mass flowmeter and/or by any of Equations 4a or 4b. The total mass flow rate ($m_T$) can be determined at block 325f based on the first and second differential pressures ($\Delta P_1$, $\Delta P_2$) measured at block 301f, the mixture density ($\rho$) determined at block 319f, the friction factor ($f_d$) determined at block 321f, and the horizontal and vertical flow dynamic pressures ($q_h$, $q_v$) determined at block 323f. In some implementations, the total mass flow rate ($m_T$) is determined at block 325f by Equation 6h.

$$m_T = C_d \varepsilon K \sqrt{2\rho\left(\Delta P_L \pm \rho g y - \frac{f_d q_v y}{D'_v} - \frac{f_d q_h x}{D'_h}\right)} \quad (6h)$$

where $C_d$ is an empirically characterized discharge coefficient, $\varepsilon$ is an expansion factor, K is a fixed geometry factor (K=A/$\sqrt{1-\beta^4}$, where A is the cross-sectional flow area of the throat of the bend and $\beta$ is the beta ratio (d/D, where d is the inner diameter downstream of the bend and D is the inner diameter upstream of the bend)), $\Delta P_L$ is the differential pressure across the bend (selected from one of the first or second differential pressures ($\Delta P_1$ or $\Delta P_2$)), g is the acceleration due to gravity, y is the vertical height difference between the pressure ports for the differential pressure sensor, x is the horizontal distance between the pressure ports for the differential pressure sensor, $D'_h$ is the equivalent (effective) inner diameter of the cross-sectional flow area for the horizontal flow of the multiphase fluid 101, and $D'_v$ is the equivalent (effective) inner diameter of the cross-sectional flow area for the vertical flow of the multiphase fluid 101.

In some implementations, the blocks in the dotted box of the multiphase fluid flow model 300F (blocks 317f, 319f, 321f, 323f, 325f, and determining the slip ratio (S)) are performed simultaneously (for example, in parallel). In some implementations, the blocks in the dotted box of the multiphase fluid flow model 300F (blocks 317f, 319f, 321f, 323f, 325f, and determining the slip ratio (S)) are performed iteratively (for example, in series) until the calculated values converge to final values. At block 327f, various volumetric flow rates of the multiphase fluid 101 are determined. The various volumetric flow rates determined at block 327f can include a total volumetric flow rate ($Q_T$) of the multiphase fluid 101, a gas phase volumetric flow rate ($Q_g$) of the multiphase fluid 101, a liquid phase volumetric flow rate ($Q_l$, including the aqueous phase and the oil phase) of the multiphase fluid 101, an oil phase volumetric flow rate ($Q_o$) of the multiphase fluid 101, and an aqueous phase volumetric flow rate ($Q_a$) of the multiphase fluid 101. The various volumetric flow rates determined at block 327f can be calculated by Equations 6j$_t$, 6j$_g$, 6j$_l$, 6j$_o$, and 6j$_a$.

$$Q_T = \frac{m_T}{\rho} \quad (6j_t)$$

$$Q_g = Q_T \alpha_g \quad (6j_g)$$

$$Q_l = Q_T(1 - \alpha_g) \quad (6j_l)$$

$$Q_o = Q_T(1 - R_{WL}) \quad (6j_o)$$

$$Q_a = Q_T R_{WL} \quad (6j_a)$$

Figure 3G:
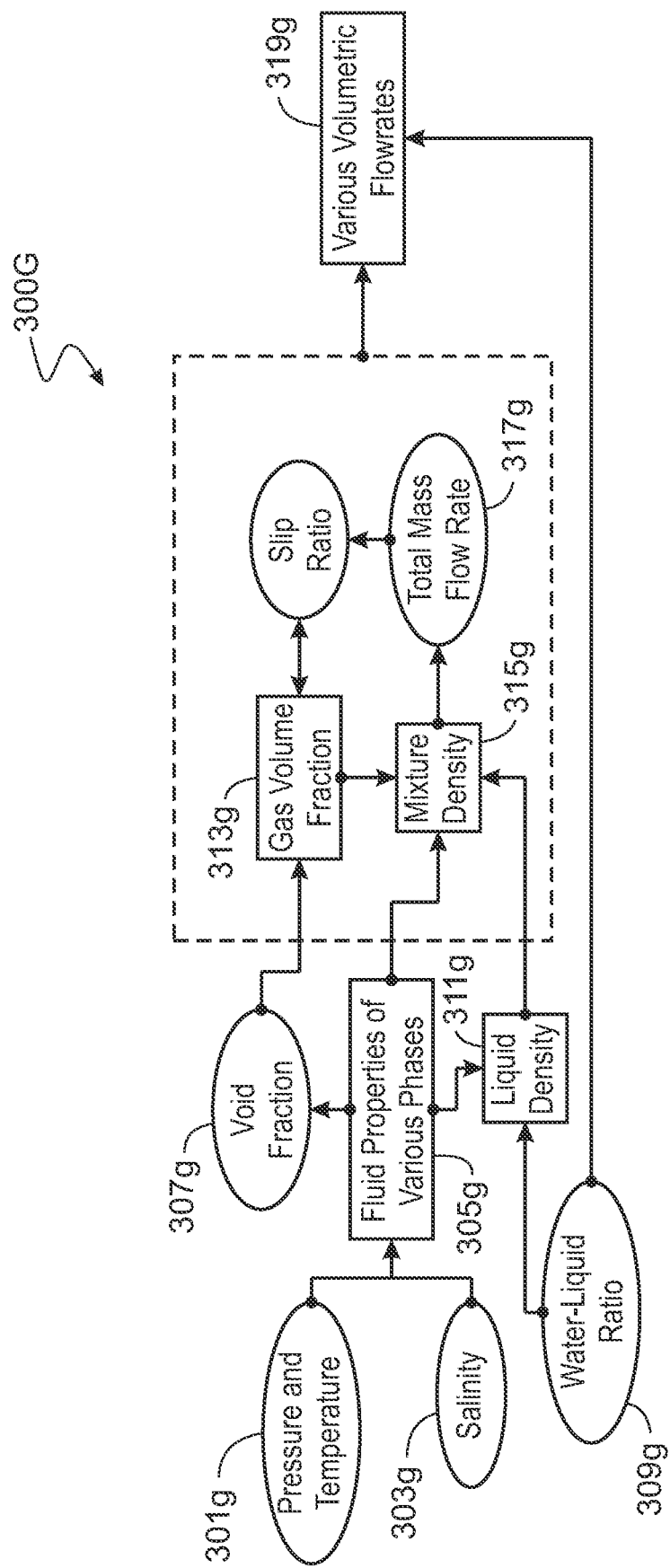
FIG. 3G is a flowchart depicting an example multiphase fluid flow model.

FIG. 3G is a flowchart depicting an example multiphase fluid flow model 300G. Any one of the apparatuses 100H, 100I, or 100J can, for example, be used to implement the model 300G to characterize a multiphase fluid, such as the multiphase fluid 101. At block 301g, various operating conditions (such as pressure and temperature) about the flowing multiphase fluid 101 are determined. The various operating conditions determined at block 301g can be measured, for example, by external sensors, such as pressure sensors and temperature sensors. The various operating conditions determined at block 301g can include, for example, differential pressure measurements. At block 303g, a salinity of the aqueous phase of the multiphase fluid 101 is measured. The salinity of the aqueous phase of the multiphase fluid 101 can be measured at block 303g, for example, using a salinity sensor. In some implementations, the salinity sensor includes electrodes for generating a current to measure conductivity of the aqueous phase of the multiphase fluid 101. At block 305g, fluid properties (such as density) of the various phases (such as the gas phase, the aqueous phase, and the oil phase) of the multiphase fluid 101 are determined. The fluid properties of the various phases can be determined at block 305g based on the operating conditions measured at block 301g and the salinity of the aqueous phase measured at block 303g. At block 307g, a void fraction ($\lambda_g$) of the multiphase fluid 101 is determined. The void fraction ($\lambda_g$) can be determined at block 307g, for example, using an external sensor (such as an ultrasonic sensor) and/or by Equation 6b. At block 309g, a water-liquid ratio ($R_{WL}$) of the multiphase fluid 101 is determined. The water-liquid ratio ($R_{WL}$) can be determined at block 309g, for example, using an external sensor (such as a dynamic pressure sensor). At block 311g, a density of the liquid phase ($\rho_l$, including the aqueous phase and the oil phase) is determined. The density of the liquid phase ($\rho_l$) can be determined at block 311g based on the densities of the various phases of the flowing multiphase fluid 101 and the water-liquid ratio ($R_{WL}$) determined at block 309g. The density of the liquid phase ($\rho_l$) can be determined at block 311g, for example, by Equation 6c.

At block 313g, a gas phase volume fraction ($\alpha_g$) of the multiphase fluid 101 is calculated based on the void fraction ($\lambda_g$) determined at block 307g and slip ratio (S) of the flowing multiphase fluid 101. The slip ratio (S) used at block 313g to determine the gas phase volume fraction ($\alpha_g$) can, for example, be measured by an external sensor or assumed to be substantially equal to 1 as an initial guess. At block 315g, a mixture density ($\rho$) of the multiphase fluid 101 is calculated based on the gas phase volume fraction ($\alpha_g$) determined at block 313g, the density of the gas phase ($\rho_g$) determined at block 305g, and the density of the liquid phase ($\rho_l$) determined at block 311g. The mixture density ($\rho$) can be determined at block 315g, for example, by Equation 6d. At block 317g, a total mass flow rate ($m_T$) of the multiphase fluid 101 is determined. The total mass flow rate ($m_T$) can be determined at block 317g, for example, by a mass flowmeter and/or by any of Equations 4a or 4b. In some implementations, the blocks in the dotted box of the multiphase fluid flow model 300G (blocks 313g, 315g, 317g, and determining the slip ratio (S)) are performed simultaneously (for example, in parallel). In some implementations, the blocks in the dotted box of the multiphase fluid flow model 300G (blocks 313g, 315g, 317g, and determining the slip ratio (S)) are performed iteratively (for example, in series) until the calculated values converge to final values.

At block 319g, various volumetric flow rates of the multiphase fluid 101 are determined. The various volumetric flow rates determined at block 319g can include a total volumetric flow rate ($Q_T$) of the multiphase fluid 101, a gas phase volumetric flow rate ($Q_g$) of the multiphase fluid 101, a liquid phase volumetric flow rate ($Q_l$, including the aqueous phase and the oil phase) of the multiphase fluid 101, an oil phase volumetric flow rate ($Q_o$) of the multiphase fluid 101, and an aqueous phase volumetric flow rate ($Q_a$) of the multiphase fluid 101. The various volumetric flow rates determined at block 319g can be calculated by Equations $6j_t$, $6j_g$, $6j_l$, $6j_o$, and $6j_a$.

Figure 4:
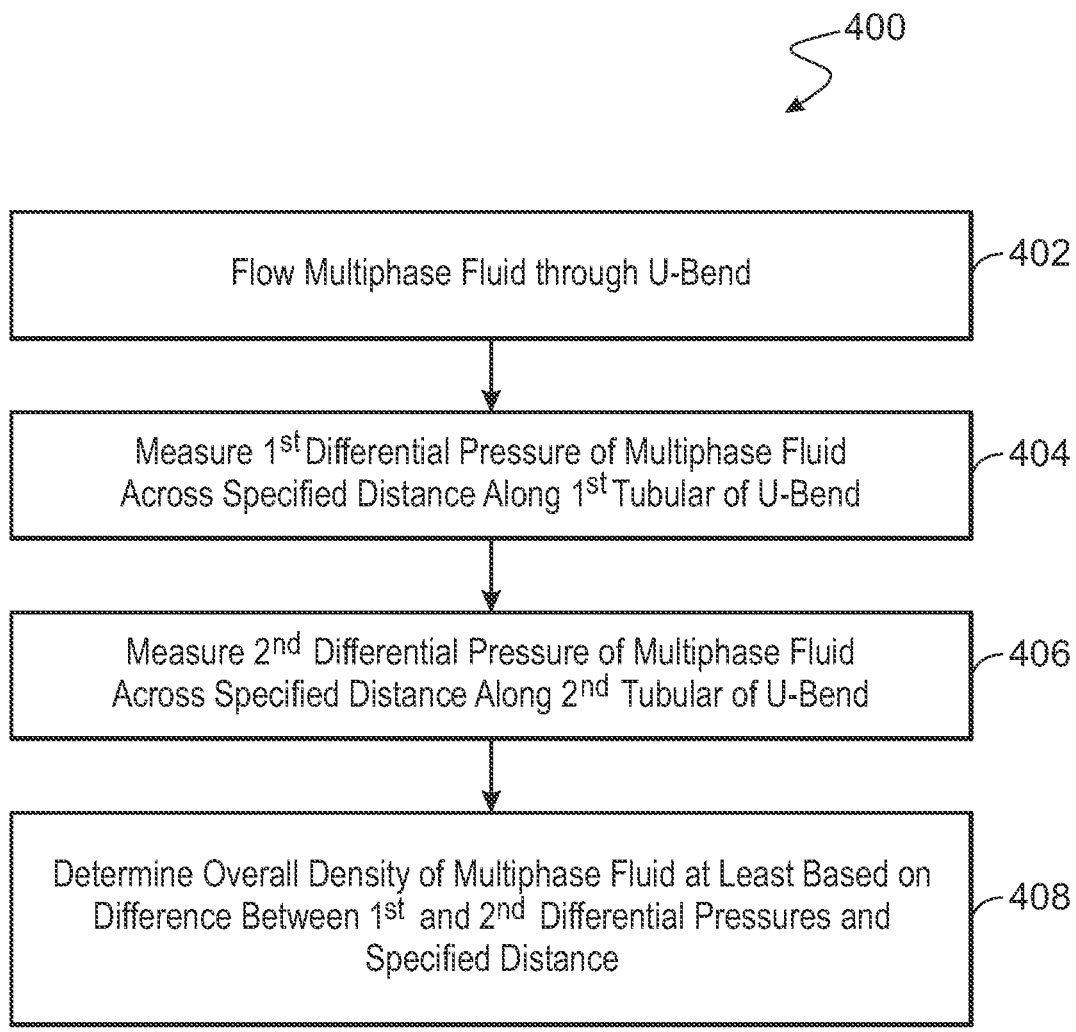
FIG. 4 is a flowchart of an example method for measuring a density of a multiphase fluid.

FIG. 4 is a flowchart of an example method 400 for measuring a density of a multiphase fluid 101. Any one of the apparatuses 100A, 100B, 100C, 100D, 100H, 100I, or 100J can be used, for example, to implement the method 400. At block 402, a multiphase fluid (such as the multiphase fluid 101) is flowed through a U-bend (such as the U-bend 102). The multiphase fluid 101 can include a gas phase 101a, an aqueous phase 101b', and an oil phase 101b". As described previously, the U-bend 102 includes a first conduit 102a, a second conduit 102b, and a connecting conduit 102c. The first conduit 102a is parallel to the second conduit 102b. The connecting conduit 102c connects the second conduit 102b to the first conduit 102a. Each of the first conduit 102a, the second conduit 102b, and the connecting conduit 102c have substantially the same cross-sectional flow area for the multiphase fluid 101 flowing through the U-bend 102. The multiphase fluid 101 flowing through the U-bend 102 flows into the first conduit 102a, through the connecting conduit 102c, and out of the second conduit 102b. At block 404, a first differential pressure ($\Delta P_1$) of the multiphase fluid 101 is measured across a specified differential pressure height (h) along the first conduit 102a. The first differential pressure ($\Delta P_1$) of the multiphase fluid 101 can be measured at block 404, for example, by the first pair of pressure sensors 104a, 104b. At block 406, a second differential pressure ($\Delta P_2$) of the multiphase fluid 101 is measured across the specified differential pressure height (h) along the second conduit 102b. The second differential pressure ($\Delta P_2$) of the multiphase fluid 101 can be measured at block 406, for example, by the second pair of pressure sensors 104c, 104d. At block 408, a mixture density ($\rho$) of the multiphase fluid 101 is determined at least based on a difference between the first differential pressure ($\Delta P_1$) and the second differential pressure ($\Delta P_2$) of the multiphase fluid 101 (measured at blocks 404 and 406, respectively) and the specified differential pressure height (h). For example, the mixture density ($\rho$) of the multiphase fluid 101 can be determined at block 406 using Equation 2d.

In some implementations, the method 400 includes determining an aqueous phase volume fraction ($\alpha_a$) of the multiphase fluid 101 at least based on the gas phase volume fraction ($\alpha_g$) of the multiphase fluid 101, the gas density ($\rho_g$) of the gas phase 101a of the multiphase fluid 101, the aqueous phase density ($\rho_a$) of the aqueous phase 101b' of the multiphase fluid 101, the oil phase density ($\rho_o$) of the oil phase 101b" of the multiphase fluid 101, and the mixture density ($\rho$) of the multiphase fluid 101. For example, the gas phase volume fraction ($\alpha_g$), the gas density ($\rho_g$), the aqueous phase density ($\rho_a$), the oil phase density ($\rho_o$), and the mixture density ($\rho$) of the multiphase fluid 101 can be input to Equation 3b and re-arranged to calculate the aqueous phase volume fraction ($\alpha_a$) of the multiphase fluid 101.

In some implementations, the method 400 includes determining a gas phase volume fraction ($\alpha_g$) of the multiphase fluid 101 at least based on the aqueous phase volume fraction ($\alpha_a$) of the multiphase fluid 101, the gas density ($\rho_g$) of the gas phase 101a of the multiphase fluid 101, the aqueous phase density ($\rho_a$) of the aqueous phase 101b' of the multiphase fluid 101, the oil phase density ($\rho_o$) of the oil phase 101b" of the multiphase fluid 101, and the mixture density ($\rho$) of the multiphase fluid 101. For example, the aqueous phase volume fraction ($\alpha_a$), the gas density ($\rho_g$), the aqueous phase density ($\rho_a$), the oil phase density ($\rho_o$), and the mixture density ($\rho$) of the multiphase fluid 101 can be input to Equation 3b and re-arranged to calculate the gas phase volume fraction ($\alpha_g$) of the multiphase fluid 101.

Figure 5:
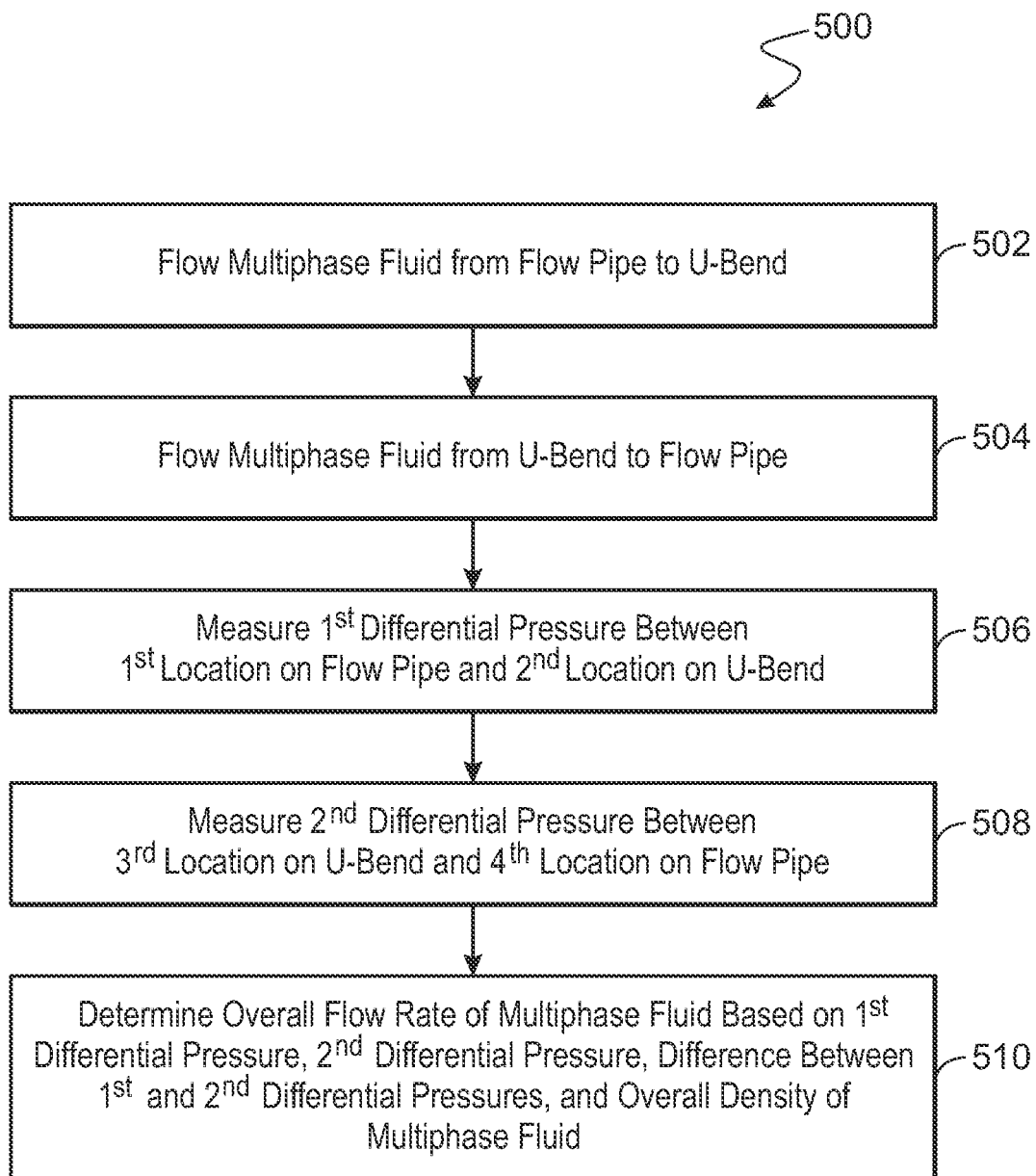
FIG. 5 is a flowchart of an example method for measuring a flow rate of a multiphase fluid.

FIG. 5 is a flowchart of an example method 500 for measuring a total flow rate of a multiphase fluid 101. Any one of the apparatuses 100E, 100H, 100I, or 100J can be used, for example, to implement the method 500. At block 502, a multiphase fluid (such as the multiphase fluid 101) is flowed from a flow pipe (such as the flow pipe 150) to a U-bend (such as the U-bend 102). The multiphase fluid 101 can include a gas phase 101a, an aqueous phase 101b', and an oil phase 101b". As described previously, the U-bend 102 includes a first conduit 102a, a second conduit 102b, and a connecting conduit 102c. The connecting conduit 102c connects the first conduit 102a to the second conduit 102b. The multiphase fluid 101 flowing through the U-bend 102 flows into the first conduit 102a, through the connecting conduit 102c, and out of the second conduit 102b. The flow pipe 150 includes the first pipe 150a (third conduit) and the second pipe 150b (fourth conduit). The first pipe 150a is connected to the first conduit 102a of the U-bend 102 by a first bend (such as the first angled bend 153a). The second pipe 150b is connected to the second conduit 102b of the U-bend 102 by a second bend (such as the second angled bend 153b). Flowing the multiphase fluid 101 from the flow pipe 150 to the U-bend 102 at block 502 includes flowing the multiphase fluid 101 from the first pipe 150a of the flow pipe 150 through the first angled bend 153a to the first conduit 102a of the U-bend 102. At block 504, the multiphase fluid 101 is flowed from the U-bend 102 to the flow pipe 150. Flowing the multiphase fluid 101 from the U-bend 102 to the flow pipe 150 at block 504 includes flowing the multiphase fluid 101 from the second conduit 102b of the U-bend 102 through the second angled bend 153b to the second pipe 150b of the flow pipe 150. At block 506, a first differential pressure of the multiphase fluid 101 is measured between a first location on the first pipe 150a of the flow pipe 150 and a second location on the first conduit 102a of the U-bend 102. For example, the first differential pressure of the multiphase fluid 101 can be measured at block 506 cooperatively by the first pressure sensor 104a coupled to the first pipe 150a of the flow pipe 150 at the first location and by the second pressure sensor 104b coupled to the first conduit 102a of the U-bend at the second location. At block 508, a second differential pressure of the multiphase fluid 101 is measured between a third location on the second conduit 102b of the U-bend 102 and a fourth location on the second pipe 150b of the flow pipe 150. The second differential pressure of the multiphase fluid 101 can be measured at block 508 cooperatively by the third pressure sensor 104c coupled to the second conduit 102b of the U-bend 102 at the third location and by the fourth pressure sensor 104d coupled to the second pipe 150b of the flow pipe 150 at the fourth location. At block 510, an overall flow rate of the multiphase fluid 101 is determined at least based on the first differential pressure (measured at block 506), the second differential pressure (measured at block 508), a difference between the first differential pressure and the second differential pressure, and an overall density of the multiphase fluid 101. For example, the total mass flow rate ($m_{T1}$) of the multiphase fluid 101 can be determined at block 510 using Equation 4a. For example, the total mass flow rate ($m_{T2}$) of the multiphase fluid 101 can be determined at block 510 using Equation 4b. In some implementations, the method 500 includes comparing the total flow rates ($m_{T1}$, $m_{T2}$) of the multiphase fluid 101 determined at block 510 (for example, determined by Equations 4a and 4b) to determine an adjustment of the discharge coefficients (for example, $C_{d1}$, $C_{d2}$).

Figure 6:
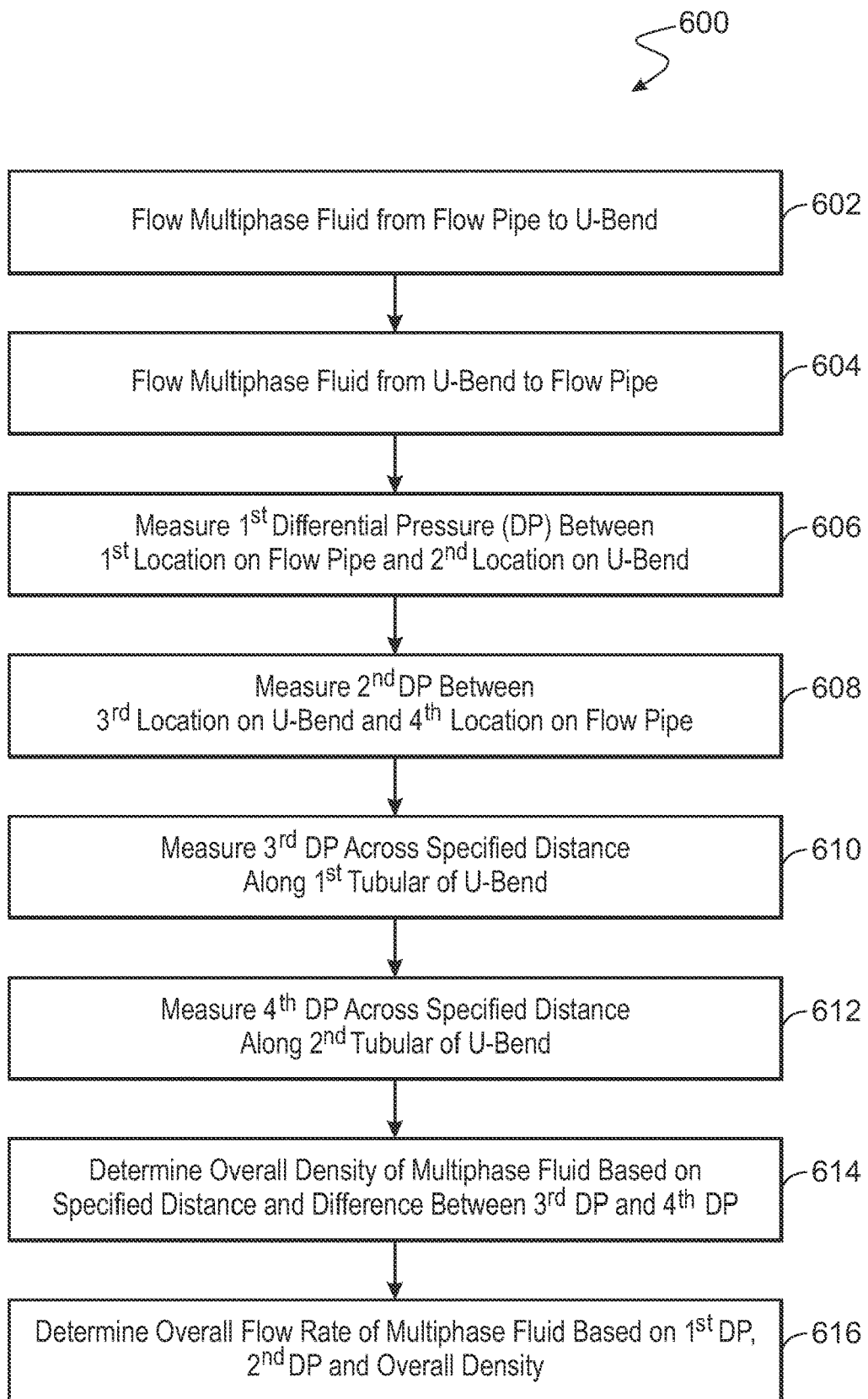
FIG. 6 is a flowchart of an example method for measuring a density and a flow rate of a multiphase fluid.

FIG. 6 is a flowchart of an example method 600 for measuring a mixture density, a total flow rate, and phase flow rates of a multiphase fluid 101. Any of the apparatuses 100H, 100I, or 100J can be used, for example, to implement the method 600. At block 602, a multiphase fluid (such as the multiphase fluid 101) is flowed from a flow pipe (such as the flow pipe 150) to a U-bend (such as the U-bend 102). The multiphase fluid 101 can include a gas phase 101a, an aqueous phase 101b', and an oil phase 101b''. As described previously, the U-bend 102 includes a first conduit 102a, a second conduit 102b, and a connecting conduit 102c. The connecting conduit 102c connects the first conduit 102a to the second conduit 102b. The multiphase fluid 101 flowing through the U-bend 102 flows into the first conduit 102a, through the connecting conduit 102c, and out of the second conduit 102b. The flow pipe 150 includes the first pipe 150a (third conduit) and the second pipe 150b (fourth conduit). The first pipe 150a is connected to the first conduit 102a of the U-bend 102 by a first bend (such as the first angled bend 153a). The second pipe 150b is connected to the second conduit 102b of the U-bend 102 by a second bend (such as the second angled bend 153b). Flowing the multiphase fluid 101 from the flow pipe 150 to the U-bend 102 at block 602 includes flowing the multiphase fluid 101 from the first pipe 150a of the flow pipe 150 through the first angled bend 153a to the first conduit 102a of the U-bend 102. At block 604, the multiphase fluid 101 is flowed from the U-bend 102 to the flow pipe 150. Flowing the multiphase fluid 101 from the U-bend 102 to the flow pipe 150 at block 604 includes flowing the multiphase fluid 101 from the second conduit 102b of the U-bend 102 through the second angled bend 153b to the second pipe 150b of the flow pipe 150. At block 606, a first differential pressure of the multiphase fluid 101 is measured between a first location on the first pipe 150a of the flow pipe 150 and a second location on the first conduit 102a of the U-bend 102. For example, the first differential pressure of the multiphase fluid 101 can be measured at block 606 cooperatively by the first pressure sensor 104a coupled to the first pipe 150a of the flow pipe 150 at the first location and by the second pressure sensor 104b coupled to the first conduit 102a of the U-bend at the second location. At block 608, a second differential pressure of the multiphase fluid 101 is measured between a third location on the second conduit 102b of the U-bend 102 and a fourth location on the second pipe 150b of the flow pipe 150. The second differential pressure of the multiphase fluid 101 can be measured at block 608 cooperatively by the third pressure sensor 104c coupled to the second conduit 102b of the U-bend 102 at the third location and by the fourth pressure sensor 104d coupled to the second pipe 150b of the flow pipe 150 at the fourth location. At block 610, a third differential pressure of the multiphase fluid 101 is measured across a specified height (such as the specified height, h) along the longitudinal length of the first conduit 102a of the U-bend 102. The third differential pressure of the multiphase fluid 101 can be measured at block 610 by the third pair of pressure sensors 104e, 104f coupled to the first conduit 102a. At block 612, a fourth differential pressure of the multiphase fluid 101 is measured across the specified height (h) along the longitudinal length of the second conduit 102b of the U-bend 102. The fourth differential pressure of the multiphase fluid 101 can be measured at block 612 by the fourth pair of pressure sensors 104g, 104h coupled to the second conduit 102b. At block 614, a mixture density ($\rho$) of the multiphase fluid 101 is determined at least based on a difference between the third differential pressure ($\Delta P_3$) and the fourth differential pressure ($\Delta P_4$) of the multiphase fluid 101 (measured at blocks 610 and 612, respectively) and the specified height (h). For example, the mixture density ($\rho$) of the multiphase fluid 101 can be determined at block 614 using Equation 2d, where $\Delta P_1$ is substituted for the third differential pressure ($\Delta P_3$) measured by the third pair of pressure sensors 104e, 104f at block 610, $\Delta P_2$ is substituted for the fourth differential pressure ($\Delta P_4$) measured by the fourth pair of pressure sensors 104g, 104h at block 612, and $h_2$ is substituted for the specified height (h). At block 616, a total flow rate of the multiphase fluid 101 is determined at least based on the first differential pressure (measured at block 606), the second differential pressure (measured at block 608), and a mixture density of the multiphase fluid 101 (determined at block 614). For example, the total mass flow rate ($m_{T1}$) of the multiphase fluid 101 can be determined at block 616 using Equation 4a. For example, the total mass flow rate ($m_{T2}$) of the multiphase fluid 101 can be determined at block 616 using Equation 4b.

In some implementations, the method 600 includes comparing the total flow rates ($m_{T1}$, $m_{T2}$) of the multiphase fluid 101 determined at block 616 (for example, determined by Equations 4a and 4b) to determine an adjustment of the discharge coefficients ($C_{d1}$, $C_{d2}$). In implementation in which the method 600 is performed by the apparatus 100G, the method 600 can include measuring various dynamic pressures of the multiphase fluid 101 flowing through the U-bend 102. The dynamic pressures of the multiphase fluid 101 can be measured, for example, by the dynamic pressure sensors 106a, 106b, 106c. The dynamic pressure measurements taken by the dynamic pressure sensors 106a, 106b, 106c can be cross-correlated (for example, by the processor 705) to determine a speed of sound of the multiphase fluid 101 flowing through the U-bend 102. The speed of sound of the multiphase fluid 101 and the mixture density ($\rho$) of the multiphase fluid 101 can then be used to determine the water-liquid ratio of the multiphase fluid 101. For example, the speed of sound of the multiphase fluid 101 and the mixture density ($\rho$) of the multiphase fluid 101 can be compared to a plotted graph of various phase curves (gas/oil, gas/aqueous, oil/aqueous) to determine the water-liquid ratio.

FIG. 7 is a block diagram of an example computer 700 used to provide computational functionalities associated with described algorithms, methods, functions, processes, flows, and procedures, as described in this specification, according to an implementation. The illustrated computer 700 is intended to encompass any computing device such as a server, desktop computer, laptop/notebook computer, one or more processors within these devices, or any other processing device, including physical or virtual instances (or both) of the computing device. Additionally, the computer 700 can include a computer that includes an input device, such as a keypad, keyboard, touch screen, or other device that can accept user information, and an output device that conveys information associated with the operation of the computer 700, including digital data, visual, audio information, or a combination of information.

The computer 700 includes an interface 704. Although illustrated as a single interface 704 in FIG. 7, two or more interfaces 704 may be used according to particular needs, desires, or particular implementations of the computer 700. Although not shown in FIG. 7, the computer 700 can be communicably coupled with a network. The interface 704 is used by the computer 700 for communicating with other systems that are connected to the network in a distributed environment. Generally, the interface 704 comprises logic encoded in software or hardware (or a combination of software and hardware) and is operable to communicate with the network. More specifically, the interface 704 may comprise software supporting one or more communication protocols associated with communications such that the network or interface's hardware is operable to communicate physical signals within and outside of the illustrated computer 700. The interface 704 can include a control interface, which can be used to couple the computer 700 to controls. In some implementations, the control interface is a bank of relays, a bank of MOSFET power controllers, a serial peripheral interface (SPI), or a Fieldbus, and the like. The interface 704 can include a sensor interface, which can be used to couple the computer 700 to sensors. In some implementations, the sensor interface is a bank of analog-to-digital converters (ADCs), and I2C bus, a serial peripheral interface (SPI) bus, or a Fieldbus, and the like. The interface 704 can include a human machine interface, which can be used by a user to interact with the computer 700. In some implementations, the human machine interface includes a monitor or a touch screen that is configured to display information, for example, to a user.

The computer 700 includes a processor 705. The processor 705 may be a microprocessor, a multi-core processor, a multithreaded processor, an ultra-low-voltage processor, an embedded processor, or a virtual processor. In some embodiments, the processor 705 may be part of a system-on-a-chip (SoC) in which the processor 705 and the other components of the computer 700 are formed into a single integrated electronics package. In some implementations, the processor 705 may include processors from Intel® Corporation of Santa Clara, California, from Advanced Micro Devices, Inc. (AMD) of Sunnyvale, California, or from ARM Holdings, LTD., Of Cambridge, England. Any number of other processors from other suppliers may also be used. Although illustrated as a single processor 705 in FIG. 7, two or more processors may be used according to particular needs, desires, or particular implementations of the computer 700. Generally, the processor 705 executes instructions and manipulates data to perform the operations of the computer 700 and any algorithms, methods, functions, processes, flows, and procedures as described in this specification. The processor 705 may communicate with other components of the computer 700 over a bus. The bus may include any number of technologies, such as industry standard architecture (ISA), extended ISA (EISA), peripheral component interconnect (PCI), peripheral component interconnect extended (PCIx), PCI express (PCIe), or any number of other technologies. The bus may be a proprietary bus, for example, used in an SoC based system. Other bus technologies may be used, in addition to, or instead of, the technologies above.

The computer 700 can also include a database 706 that can hold data for the computer 700 or other components (or a combination of both) that can be connected to the network. Although illustrated as a single database 706 in FIG. 7, two or more databases (of the same or combination of types) can be used according to particular needs, desires, or particular implementations of the computer 700 and the described functionality. While database 706 is illustrated as an integral component of the computer 700, database 706 can be external to the computer 700. The database 706 can be used for the persistent storage of information, such as data, applications, operating systems, and so forth. The database 706 may be a nonvolatile RAM, a solid-state disk drive, or a flash drive, among others. In some implementations, the database 306 will include a hard disk drive, such as a micro hard disk drive, a regular hard disk drive, or an array of hard disk drives, for example, associated with a DCS or a cloud server.

The computer 700 also includes a memory 707 that can hold data for the computer 700 or other components (or a combination of both) that can be connected to the network. Although illustrated as a single memory 707 in FIG. 7, two or more memories 707 (of the same or combination of types) can be used according to particular needs, desires, or particular implementations of the computer 700 and the described functionality. While memory 707 is illustrated as an integral component of the computer 700, memory 707 can be external to the computer 700. The memory 707 can be a transitory or non-transitory storage medium. In some implementations, such as in PLCs and other process control units, the memory 707 is integrated with the database 706 used for long-term storage of programs and data. The memory 707 can include any number of volatile and non-volatile memory devices, such as volatile random-access memory (RAM), static random-access memory (SRAM), flash memory, and the like. In smaller devices, such as PLCs, the memory 707 may include registers associated with the processor 705 itself.

The memory 707 stores computer-readable instructions executable by the processor 705 that, when executed, cause the processor 705 to perform operations, such as receiving a first differential pressure signal from the first pair of pressure sensors 104a, 104b; receiving a second differential pressure signal from the second pair of pressure sensors 104c, 104d; and determining an overall density of the multiphase fluid 101 at least based on a difference between the first differential pressure and the second differential pressure of the multiphase fluid 101 and the specified differential pressure height, h. The computer 700 can also include a power supply 714. The power supply 714 can include a rechargeable or non-rechargeable battery that can be configured to be either user- or non-user-replaceable. The power supply 714 can be hard-wired. There may be any number of computers 700 associated with, or external to, a computer system containing computer 700, each computer 700 communicating over the network. Further, the term "client," "user," "operator," and other appropriate terminology may be used interchangeably, as appropriate, without departing from this specification. Moreover, this specification contemplates that many users may use one computer 700, or that one user may use multiple computers 700.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any subcombination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described components and systems can generally be integrated together or packaged into multiple products.

Accordingly, the previously described example implementations do not define or constrain the present disclosure. Other changes, substitutions, and alterations are also possible without departing from the spirit and scope of the present disclosure.

What is claimed is:

1. A system comprising:
    a U-bend configured to flow a multiphase fluid, the multiphase fluid comprising a gas phase, an aqueous phase, and an oil phase, and the U-bend comprising:
        a first conduit;
        a second conduit, wherein a cross-sectional flow area of the first conduit is substantially the same as a cross-sectional flow area of the second conduit; and
        a connecting conduit connecting the first conduit to the second conduit;
    a third conduit configured to flow the multiphase fluid, the third conduit having a cross-sectional flow area that is different from the cross-sectional flow area of the first conduit;
    a first bend connecting the third conduit to the first conduit;
    a fourth conduit configured to flow the multiphase fluid, the fourth conduit having a cross-sectional flow area that is substantially the same as the cross-sectional flow area of the third conduit;
    a second bend connecting the fourth conduit to the second conduit;
    a first differential pressure sensor configured to measure a first differential pressure of the multiphase fluid between a first location on the third conduit of the flow pipe and a second location on the first conduit of the U-bend;
    a second differential pressure sensor configured to measure a second differential pressure of the multiphase fluid between a third location on the second conduit of the U-bend and a fourth location on the fourth conduit of the flow pipe;
a third differential pressure sensor configured to measure a third differential pressure of the multiphase fluid across a specified height along the first conduit of the U-bend;
a fourth differential pressure sensor configured to measure a fourth differential pressure of the multiphase fluid across the specified height along the second conduit of the U-bend; and
a computer, comprising:
  a processor communicatively coupled to the first differential pressure sensor, the second differential pressure sensor, the third differential pressure sensor, and the fourth differential pressure sensor; and
  a computer-readable storage medium coupled to the processor and storing programming instructions for execution by the processor, the programming instructions instructing the processor to perform operations comprising:
    receiving a first differential pressure signal from the first differential pressure sensor, the first differential pressure signal representing the first differential pressure of the multiphase fluid;
    receiving a second differential pressure signal from the second differential pressure sensor, the second differential pressure signal representing the second differential pressure of the multiphase fluid;
    receiving a third differential pressure signal from the third differential pressure sensor, the third differential pressure signal representing the third differential pressure of the multiphase fluid;
    receiving a fourth differential pressure signal from the fourth differential pressure sensor, the fourth differential pressure signal representing the fourth differential pressure of the multiphase fluid;
    determining a mixture density of the multiphase fluid at least based on the specified distance and a difference between the third differential pressure and the fourth differential pressure; and
    determining a total flow rate of the multiphase fluid at least based on the first differential pressure, the second differential pressure, and the mixture density of the multiphase fluid.

2. The system of claim 1, wherein the mixture density of the multiphase fluid is determined by:

$$\rho = \frac{\Delta P_3 - \Delta P_4}{2 \times g \times h},$$

wherein $\rho$ is the mixture density of the multiphase fluid, $\Delta P_3$ is the third differential pressure of the multiphase fluid, $\Delta P_4$ is the fourth differential pressure of the multiphase fluid, g is an acceleration due to gravity, and h is the specified height.

3. The system of claim 2, wherein the total flow rate of the multiphase fluid is determined as a first total mass flow rate of the multiphase fluid at least based on a first differential pressure equation:

$$m_{T1} = C_{d1} \times \varepsilon_1 \times K_1 \times \sqrt{2 \times \rho \times (\Delta P_1 - \rho \times g \times h)},$$

wherein $m_{T1}$ is the first total mass flow rate of the multiphase fluid, $C_{d1}$ is a first discharge coefficient, $\varepsilon_1$ is a first expansion factor, $K_1$ is a first fixed geometry factor proportional to the cross-sectional flow area of the first conduit, $\Delta P_1$ is the first differential pressure, $\rho$ is the mixture density of the multiphase fluid, g is the acceleration due to gravity, and h is the specified height, wherein the total flow rate is equal to the first total mass flow rate.

4. The system of claim 3, wherein the total flow rate of the multiphase fluid is determined as a second total mass flow rate of the multiphase fluid at least based on a second differential pressure equation:

$$m_{T2} = C_{d2} \times \varepsilon_2 \times K_2 \times \sqrt{2 \times \rho \times (\Delta P_2 + \rho \times g \times h)},$$

wherein $m_{T2}$ is the second total mass flow rate of the multiphase fluid, $C_{d2}$ is a second discharge coefficient, $\varepsilon_2$ is a second expansion factor, $K_2$ is a second fixed geometry factor proportional to a cross-sectional flow area of the fourth conduit, $\Delta P_2$ is the second differential pressure, $\rho$ is the mixture density of the multiphase fluid, g is the acceleration due to gravity, and h is the specified height, wherein the total flow rate is equal to the second total mass flow rate.

5. The system of claim 4, wherein the operations performed by the processor comprise comparing the first total mass flow rate of the multiphase fluid and the second total mass flow rate of the multiphase fluid to determine an adjustment of the first discharge coefficient ($C_{d1}$) or an adjustment of the second discharge coefficient ($C_{d2}$).

6. The system of claim 4, wherein the first total mass flow rate ($m_{T1}$) is equal to the second total mass flow rate ($m_{T2}$), the mixture density of the multiphase fluid is a first mixture density of the multiphase fluid, and the operations performed by the processor comprise determining a second mixture density of the multiphase fluid at least based on a combined differential pressure equation:

$$\rho_2 = \frac{Z \times \Delta P_1 - \Delta P_2}{g \times (1 + Z)},$$

wherein $\rho_2$ is the second mixture density of the multiphase fluid, $\Delta P_1$ is the first differential pressure, $\Delta P_2$ is the second differential pressure, g is the acceleration due to gravity, and Z is defined by:

$$Z = \left(\frac{C_{d1} \times \varepsilon_1 \times K_1}{C_{d2} \times \varepsilon_2 \times K_2}\right)^2,$$

wherein $C_{d1}$ is the first discharge coefficient, $\varepsilon_1$ is the first expansion factor, $K_1$ is the first fixed geometry factor, $C_{d2}$ is the second discharge coefficient, $\varepsilon_2$ is the second expansion factor, and $K_2$ is the second fixed geometry factor.

7. The system of claim 6, wherein the operations performed by the processor comprise comparing the first mixture density of the multiphase fluid and the second mixture density of the multiphase fluid.

8. The system of claim 6, comprising a plurality of dynamic pressure sensors coupled to the U-bend, wherein each dynamic pressure sensor of the plurality of dynamic pressure sensors is configured to measure a dynamic pressure of the multiphase fluid flowing through the U-bend, and the operations performed by the processor comprise:
  cross-correlating the dynamic pressures measured by the plurality of dynamic pressure sensors to determine a speed of sound of the multiphase fluid flowing through the U-bend; and determining a water-liquid ratio at least based on the speed of sound of the multiphase fluid and the mixture density of the multiphase fluid, wherein the water-liquid ratio is a ratio of a volume of the aqueous phase to a sum of the volume of the aqueous phase and a volume of the oil phase.

9. The system of claim 8, wherein the third differential pressure sensor is a first circumferential pressure sensor that spans an entire circumference of the first conduit, and the fourth differential pressure sensor is a second circumferential pressure sensor that spans an entire circumference of the second conduit.

10. A method comprising:

flowing a multiphase fluid from a flow pipe to a U-bend, wherein the multiphase fluid comprises a gas phase, an aqueous phase, and an oil phase, and the U-bend comprises:

a first conduit;

a second conduit; and a connecting conduit connecting the first conduit to the second conduit, wherein the multiphase fluid flowing through the U-bend flows into the first conduit, through the connecting conduit, and out of the second conduit;

flowing the multiphase fluid from the U-bend to the flow pipe, wherein:

the flow pipe comprises a third conduit and a fourth conduit;

the third conduit of the flow pipe is connected to the first conduit of the U-bend by a first bend;

the fourth conduit of the flow pipe is connected to the second conduit of the U-bend by a second bend;

flowing the multiphase fluid from the flow pipe to the U-bend comprises flowing the multiphase fluid from the third conduit of the flow pipe through the first bend to the first conduit of the U-bend; and flowing the multiphase fluid from the U-bend to the flow pipe comprises flowing the multiphase fluid from the second conduit of the U-bend through the second bend to the fourth conduit of the flow pipe;

measuring a first differential pressure of the multiphase fluid between a first location on the third conduit of the flow pipe and a second location on the first conduit of the U-bend;

measuring a second differential pressure of the multiphase fluid between a third location on the second conduit of the U-bend and a fourth location on the fourth conduit of the flow pipe;

measuring a third differential pressure of the multiphase fluid across a specified height along the first conduit of the U-bend;

measuring a fourth differential pressure of the multiphase fluid across the specified distance along a longitudinal length of the second conduit of the U-bend;

determining a mixture density of the multiphase fluid at least based on the specified height and a difference between the third differential pressure and the fourth differential pressure; and determining a total flow rate of the multiphase fluid at least based on the first differential pressure, the second differential pressure, and the mixture density of the multiphase fluid.

11. The method of claim 10, wherein the mixture density of the multiphase fluid is determined by:

$$\rho = \frac{\Delta P_3 - \Delta P_4}{2 \times g \times h},$$

wherein $\rho$ is the mixture density of the multiphase fluid, $\Delta P_3$ is the third differential pressure of the multiphase fluid, $\Delta P_4$ is the fourth differential pressure of the multiphase fluid, g is an acceleration due to gravity, and h is the specified height.

12. The method of claim 11, wherein the total flow rate of the multiphase fluid is determined as a first total mass flow rate of the multiphase fluid at least based on a first differential pressure equation:

$$m_{T1} = C_{d1} \times \varepsilon_1 \times K_1 \times \sqrt{2 \times \rho \times (\Delta P_1 - \rho \times g \times h)},$$

wherein $m_{T1}$ is the first total mass flow rate of the multiphase fluid, $C_{d1}$ is a first discharge coefficient, $\varepsilon_1$ is a first expansion factor, $K_1$ is a first fixed geometry factor proportional to the cross-sectional flow area of the first conduit, $\Delta P_1$ is the first differential pressure, $\rho$ is the mixture density of the multiphase fluid, g is the acceleration due to gravity, and h is the specified height, wherein the total flow rate is equal to the first total mass flow rate.

13. The method of claim 12, wherein the total flow rate of the multiphase fluid is determined as a second total mass flow rate of the multiphase fluid at least based on a second differential pressure equation:

$$m_{T2} = C_{d2} \times \varepsilon_2 \times K_2 \times \sqrt{2 \times \rho \times (\Delta P_2 + \rho \times g \times h)},$$

wherein $m_{T2}$ is the second total mass flow rate of the multiphase fluid, $C_{d2}$ is a second discharge coefficient, $\varepsilon_2$ is a second expansion factor, $K_2$ is a second fixed geometry factor proportional to the cross-sectional flow area of the fourth conduit, $\Delta P_2$ is the second differential pressure, $\rho$ is the mixture density of the multiphase fluid, g is the acceleration due to gravity, and h is the specified height, wherein the total flow rate is equal to the second total mass flow rate.

14. The method of claim 13, comprising comparing the first total mass flow rate of the multiphase fluid and the second v flow rate of the multiphase fluid to determine an adjustment of the first discharge coefficient ($C_{d1}$) or an adjustment of the second discharge coefficient ($C_{d2}$).

15. The method of claim 14, wherein the first total mass flow rate ($m_{T1}$) is equal to the second total mass flow rate ($m_{T2}$), the mixture density of the multiphase fluid is a first mixture density of the multiphase fluid, and the method comprises determining a second mixture density of the multiphase fluid at least based on a combined differential pressure equation:

$$\rho_2 = \frac{Z \times \Delta P_1 - \Delta P_2}{g \times (1 + Z)},$$

wherein $\rho_2$ is the second mixture density of the multiphase fluid, $\Delta P_1$ is the first differential pressure, $\Delta P_2$ is the second differential pressure, g is the acceleration due to gravity, and Z is defined by:

$$Z = \left(\frac{C_{d1} \times \varepsilon_1 \times K_1}{C_{d2} \times \varepsilon_2 \times K_2}\right)^2,$$

wherein $C_{d1}$ is the first discharge coefficient, $\varepsilon_1$ is the first expansion factor, $K_1$ is the first fixed geometry factor, $C_{d2}$ is the second discharge coefficient, $\varepsilon_2$ is the second expansion factor, and $K_2$ is the second fixed geometry factor.

16. The method of claim 15, comprising comparing the first mixture density of the multiphase fluid and the second mixture density of the multiphase fluid to determine an accuracy of the first mixture density.

17. The method of claim 16, comprising:
measuring a plurality of dynamic pressures of the multiphase fluid flowing through the U-bend;
cross-correlating the plurality of dynamic pressures to determine a speed of sound of the multiphase fluid flowing through the U-bend; and
determining a water-liquid ratio at least based on the speed of sound of the multiphase fluid and the mixture density of the multiphase fluid, wherein the water-liquid ratio is a ratio of a volume of the aqueous phase to a sum of the volume of the aqueous phase and a volume of the oil phase.

18. The method of claim 17, wherein:
the first differential pressure is measured by a first differential pressure sensor, wherein the first differential pressure sensor is coupled to the third conduit of the flow pipe at the first location and coupled to the first conduit of the U-bend at the second location;
the second differential pressure is measured by a second differential pressure sensor, wherein the second differential pressure sensor is coupled to the second conduit of the U-bend at the third location and coupled to the fourth conduit of the flow pipe at the fourth location;
the third differential pressure is measured by a third differential pressure sensor, wherein the third differential pressure sensor is coupled to the first conduit of the U-bend at a fifth location and coupled to the first conduit of the U-bend at a sixth location, the fifth location and the sixth location separated by the specified height along the first conduit; and
the fourth differential pressure is measured by a fourth differential pressure sensor, wherein the fourth differential pressure sensor is coupled to the second conduit of the U-bend at a seventh location and coupled to the second conduit of the U-bend at an eighth location, the seventh location and the eighth location separated by the specified height along the second conduit.

19. The method of claim 18, wherein the third differential pressure sensor is a first circumferential pressure sensor that spans an entire circumference of the first conduit, and the fourth differential pressure sensor is a second circumferential pressure sensor that spans an entire circumference of the second conduit.

* * * * *